US012239321B2

(12) United States Patent
Augelli et al.

(10) Patent No.: US 12,239,321 B2
(45) Date of Patent: Mar. 4, 2025

(54) SYSTEMS AND METHODS FOR INTRODUCING AND MONITORING A NEGATIVE PRESSURE DEVICE FOR PROTECTING AN INTESTINAL ANASTOMOSIS

(71) Applicant: SafeHeal SAS, Paris (FR)

(72) Inventors: Michael J. Augelli, Avon, CT (US); Daniel Congdon, Somerville, MA (US); Ralph Allen Hulseman, Greenville, SC (US); Cameron L. McPherson, Greenville, SC (US)

(73) Assignee: SafeHeal SAS, Paris (FR)

( * ) Notice: Subject to any disclaimer, the term of this patent is extended or adjusted under 35 U.S.C. 154(b) by 0 days.

(21) Appl. No.: 18/607,076

(22) Filed: Mar. 15, 2024

(65) Prior Publication Data

US 2024/0307063 A1    Sep. 19, 2024

Related U.S. Application Data

(60) Provisional application No. 63/589,973, filed on Oct. 12, 2023, provisional application No. 63/589,965, (Continued)

(30) Foreign Application Priority Data

Mar. 17, 2023 (EP) .................................. 23305367

(51) Int. Cl.
*A61B 17/11* (2006.01)
*A61M 1/00* (2006.01)
*A61B 17/00* (2006.01)

(52) U.S. Cl.
CPC .......... *A61B 17/1114* (2013.01); *A61M 1/98* (2021.05); *A61B 2017/00022* (2013.01); (Continued)

(58) Field of Classification Search
CPC ...... A61B 17/1114; A61B 2017/00022; A61B 2017/00119; A61B 2017/00544; (Continued)

(56) References Cited

U.S. PATENT DOCUMENTS

| | | |
|---|---|---|
| 3,799,172 A | 3/1974 | Szpur |
| 3,885,567 A | 5/1975 | Ross |

(Continued)

FOREIGN PATENT DOCUMENTS

| | | |
|---|---|---|
| CN | 102387759 A | 3/2012 |
| CN | 103370016 A | 10/2013 |

(Continued)

OTHER PUBLICATIONS

Buhl S., et al., "Humidity Influence on the Adhesion of Biomimetic Fibrillar Surfaces", International Journal of Materials Research, 2009, vol. 100, No. 8, pp. 1119-1126.

(Continued)

*Primary Examiner* — Jing Rui Ou
(74) *Attorney, Agent, or Firm* — Greenberg Traurig, LLP; Christopher C. Bolten; Albert K. Heng

(57) ABSTRACT

Systems and methods for monitoring a bypass device for protecting an intestinal anastomosis are provided. The system includes a pump, one or more fluid inlet lines fluidicly coupled to the pump and to a negative pressure chamber of the bypass device, and one or more sensors configured to measure data indicative of pressure within the negative pressure chamber. A controller operatively coupled to the pump and the one or more sensors may be programmed to actuate the pump to generate a vacuum within the negative pressure chamber to thereby pull intestinal tissue towards the bypass device to anchor the bypass device at a target location upstream of the intestinal anastomosis. The controller further may compare the pressure within the negative (Continued)

pressure chamber with a predetermined pressure range and, if the pressure falls outside the predetermined pressure range, adjust the pump to maintain the vacuum within the predetermined pressure range.

30 Claims, 24 Drawing Sheets

Related U.S. Application Data filed on Oct. 12, 2023, provisional application No. 63/490,847, filed on Mar. 17, 2023.

(52) U.S. Cl.
CPC ............... *A61B 2017/00119* (2013.01); *A61B 2017/00544* (2013.01); *A61B 2017/00566* (2013.01); *A61B 2017/00818* (2013.01); *A61B 2017/00955* (2013.01); *A61M 2205/3351* (2013.01)

(58) Field of Classification Search
CPC ........... A61B 2017/00566; A61B 2017/00818; A61B 2017/00955; A61M 1/98; A61M 2205/3351
See application file for complete search history.

(56) References Cited

U.S. PATENT DOCUMENTS

| | | |
|---|---|---|
| 4,627,837 A | 12/1986 | Gonzalo |
| 4,716,900 A | 1/1988 | Ravo et al. |
| 4,721,109 A | 1/1988 | Healey |
| 5,425,739 A | 6/1995 | Jessen |
| 5,534,007 A | 7/1996 | St. Germain et al. |
| 5,558,642 A | 9/1996 | Schweich, Jr. et al. |
| 5,594,038 A | 1/1997 | Kobayashi et al. |
| 5,876,448 A | 3/1999 | Thompson et al. |
| 6,068,636 A | 5/2000 | Chen |
| 6,103,255 A | 8/2000 | Levene et al. |
| 6,254,642 B1 | 7/2001 | Taylor |
| 6,325,798 B1 | 12/2001 | Edwards et al. |
| 6,379,379 B1 | 4/2002 | Wang |
| 6,398,758 B1 | 6/2002 | Jacobsen et al. |
| 6,514,282 B1 | 2/2003 | Inoue |
| 6,585,926 B1 | 7/2003 | Mirzaee |
| 6,733,519 B2 | 5/2004 | Lashinski et al. |
| 6,808,492 B2 | 10/2004 | Snyder |
| 6,926,724 B1 | 8/2005 | Chu |
| 7,025,791 B2 | 4/2006 | Levine et al. |
| 7,147,627 B2 | 12/2006 | Kim et al. |
| 7,267,694 B2 | 9/2007 | Levine et al. |
| 7,267,794 B2 | 9/2007 | Amick |
| 7,316,716 B2 | 1/2008 | Egan |
| 7,347,875 B2 | 3/2008 | Levine et al. |
| 7,509,175 B2 | 3/2009 | Sparks et al. |
| 7,547,312 B2 | 6/2009 | Bauman et al. |
| 7,643,887 B2 | 1/2010 | Imran |
| 7,678,090 B2 | 3/2010 | Risk, Jr. et al. |
| 7,744,914 B2 | 6/2010 | Li et al. |
| 7,766,973 B2 | 8/2010 | Levine et al. |
| 7,776,081 B2 | 8/2010 | Zuidema et al. |
| 7,815,591 B2 | 10/2010 | Levine et al. |
| 8,083,758 B2 | 12/2011 | Hsu et al. |
| 8,114,045 B2 | 2/2012 | Surti |
| 8,118,774 B2 | 2/2012 | Dann et al. |
| 8,167,859 B2 | 5/2012 | Shah et al. |
| 8,182,527 B2 | 5/2012 | Llanos et al. |
| 8,187,254 B2 | 5/2012 | Hissink et al. |
| 8,211,186 B2 | 7/2012 | Belhe et al. |
| 8,221,783 B2 | 7/2012 | Helmus et al. |
| 8,282,598 B2 | 10/2012 | Belhe et al. |
| 8,323,229 B2 | 12/2012 | Shin et al. |
| 8,376,981 B2 | 2/2013 | Laufer |
| 8,398,669 B2 | 3/2013 | Kim |
| 8,435,283 B2 | 5/2013 | Jordan et al. |
| 8,491,612 B2 | 7/2013 | Stopek et al. |
| 8,597,224 B2 | 12/2013 | Vargas |
| 8,636,810 B2 | 1/2014 | Rousseau |
| 8,690,817 B2 | 4/2014 | Assaf et al. |
| 8,702,641 B2 | 4/2014 | Belhe et al. |
| 8,702,642 B2 | 4/2014 | Belhe et al. |
| 8,709,093 B2 | 4/2014 | Robida et al. |
| 8,753,407 B2 | 6/2014 | Nguyen |
| 8,801,647 B2 | 8/2014 | Melanson et al. |
| 8,821,429 B2 | 9/2014 | Vargas |
| 8,828,090 B2 | 9/2014 | Terliuc |
| 8,894,699 B2 | 11/2014 | Kelley |
| 8,900,268 B2 | 12/2014 | Weidenhagen et al. |
| 8,906,046 B2 | 12/2014 | Anderson |
| 8,926,593 B2 | 1/2015 | Croizat et al. |
| 9,044,300 B2 | 6/2015 | Belhe et al. |
| 9,173,734 B2 | 11/2015 | Vargas |
| 9,265,640 B2 | 2/2016 | Harris et al. |
| 9,339,272 B2 | 5/2016 | Khosrovaninejad |
| 9,398,982 B2 | 7/2016 | Kleiner |
| 9,402,630 B2 | 8/2016 | Stopek et al. |
| 9,415,567 B2 | 8/2016 | Sogard et al. |
| 9,439,790 B2 | 9/2016 | Clerc et al. |
| 9,511,208 B2 | 12/2016 | Assaf et al. |
| 9,517,122 B2 | 12/2016 | Firstenberg et al. |
| 9,526,640 B2 | 12/2016 | Bertolino et al. |
| 9,597,206 B2 | 3/2017 | Seddon et al. |
| 9,675,360 B2 | 6/2017 | Baker |
| 9,687,334 B2 | 6/2017 | Williams et al. |
| 9,750,596 B2 | 9/2017 | Levine et al. |
| 9,764,067 B2 | 9/2017 | Fleury et al. |
| 9,789,291 B2 | 10/2017 | Assaf et al. |
| 9,827,135 B2 | 11/2017 | Fong et al. |
| 9,848,981 B2 | 12/2017 | Suri et al. |
| 9,980,727 B2 | 5/2018 | Khosrovaninejad |
| 10,172,622 B2 | 1/2019 | Kelley |
| 10,271,972 B2 | 4/2019 | Guler et al. |
| 10,441,406 B2 | 10/2019 | Firstenberg et al. |
| 10,456,138 B2 | 10/2019 | Khosrovaninejad |
| 10,531,941 B2 | 1/2020 | Hynes et al. |
| 10,758,380 B2 | 9/2020 | Bluecher et al. |
| 10,835,248 B2 | 11/2020 | Khosrovaninejad |
| 11,589,869 B2 | 2/2023 | Khosrovaninejad et al. |
| 11,857,191 B2 | 1/2024 | Khosrovaninejad |
| 11,871,929 B2 | 1/2024 | Khosrovaninejad et al. |
| 12,042,148 B2 * | 7/2024 | Khosrovaninejad ...... A61F 2/04 |
| 12,048,433 B2 | 7/2024 | Khosrovaninejad |
| 2001/0037808 A1 | 11/2001 | Deem et al. |
| 2004/0044358 A1 | 3/2004 | Khosravi et al. |
| 2004/0107004 A1 | 6/2004 | Levine et al. |
| 2004/0122527 A1 | 6/2004 | Imran |
| 2005/0004663 A1 | 1/2005 | Llanos et al. |
| 2005/0033226 A1 | 2/2005 | Kim |
| 2005/0062610 A1 | 3/2005 | Johnson |
| 2005/0228409 A1 | 10/2005 | Coppi |
| 2005/0255230 A1 | 11/2005 | Clerc et al. |
| 2005/0256587 A1 | 11/2005 | Egan |
| 2005/0273075 A1 | 12/2005 | Krulevitch et al. |
| 2006/0064120 A1 | 3/2006 | Levine et al. |
| 2006/0095124 A1 | 5/2006 | Benz et al. |
| 2006/0112536 A1 | 6/2006 | Herweck et al. |
| 2006/0141012 A1 | 6/2006 | Gingras |
| 2006/0151568 A1 | 7/2006 | Weller et al. |
| 2007/0032879 A1 | 2/2007 | Levine et al. |
| 2007/0045229 A1 | 3/2007 | Keenan et al. |
| 2007/0179590 A1 | 8/2007 | Lu et al. |
| 2007/0262161 A1 | 11/2007 | Davies |
| 2007/0282247 A1 | 12/2007 | Desai et al. |
| 2007/0282452 A1 | 12/2007 | Weitzner et al. |
| 2008/0004566 A1 | 1/2008 | Sloan |
| 2008/0033244 A1 | 2/2008 | Matsui et al. |
| 2008/0039878 A1 | 2/2008 | Williams et al. |
| 2008/0147554 A1 | 6/2008 | Stevens et al. |
| 2008/0161717 A1 | 7/2008 | Gertner |
| 2008/0167606 A1 | 7/2008 | Dann et al. |
| 2008/0195226 A1 | 8/2008 | Williams et al. |
| 2008/0208325 A1 | 8/2008 | Helmus et al. |

(56) References Cited

U.S. PATENT DOCUMENTS

| | | |
|---|---|---|
| 2008/0208357 A1 | 8/2008 | Melanson et al. |
| 2008/0255592 A1 | 10/2008 | Hsu et al. |
| 2009/0018606 A1 | 1/2009 | Sparks et al. |
| 2009/0069904 A1 | 3/2009 | Picha |
| 2009/0143722 A1 | 6/2009 | Kim |
| 2009/0220677 A1 | 9/2009 | Clerc et al. |
| 2009/0276055 A1 | 11/2009 | Harris et al. |
| 2010/0010519 A1 | 1/2010 | Stopek et al. |
| 2010/0174381 A1* | 7/2010 | Benz .................... A61F 2/945 623/23.7 |
| 2010/0179633 A1 | 7/2010 | Solem |
| 2010/0282813 A1 | 11/2010 | Milliman |
| 2011/0172760 A1 | 7/2011 | Anderson |
| 2011/0202084 A1 | 8/2011 | Hoem et al. |
| 2011/0295288 A1 | 12/2011 | Khosrovaninejad |
| 2012/0072190 A1 | 3/2012 | Sharma et al. |
| 2012/0095541 A1 | 4/2012 | Kramann |
| 2013/0006382 A1 | 1/2013 | Behan |
| 2013/0087579 A1 | 4/2013 | Knighton |
| 2013/0087597 A1 | 4/2013 | Shelton, IV et al. |
| 2013/0132054 A1 | 5/2013 | Sharma et al. |
| 2013/0178879 A1 | 7/2013 | Laufer |
| 2013/0218262 A1 | 8/2013 | Ishii et al. |
| 2013/0231753 A1 | 9/2013 | Liddy et al. |
| 2013/0261742 A1 | 10/2013 | Gaschino et al. |
| 2013/0274717 A1 | 10/2013 | Dunn |
| 2013/0304101 A1 | 11/2013 | Stopek et al. |
| 2014/0025069 A1 | 1/2014 | Willard et al. |
| 2014/0081654 A1 | 3/2014 | Bechtel et al. |
| 2014/0088622 A1 | 3/2014 | Rousseau |
| 2014/0118029 A1 | 5/2014 | Tseng et al. |
| 2014/0155997 A1 | 6/2014 | Braido |
| 2014/0163664 A1 | 6/2014 | Goldsmith |
| 2014/0222039 A1 | 8/2014 | Khosrovaninejad |
| 2014/0350694 A1 | 11/2014 | Behan |
| 2014/0371870 A1 | 12/2014 | Terliuc |
| 2015/0045715 A1 | 2/2015 | Assaf et al. |
| 2015/0119641 A1 | 4/2015 | Yamada |
| 2015/0342760 A1 | 12/2015 | Christakis et al. |
| 2016/0128819 A1 | 5/2016 | Giordano et al. |
| 2016/0220256 A1 | 8/2016 | Khosrovaninejad |
| 2016/0303381 A1 | 10/2016 | Pierce et al. |
| 2016/0331525 A1 | 11/2016 | Straubinger et al. |
| 2016/0367352 A1 | 12/2016 | Heiss |
| 2017/0027729 A1 | 2/2017 | Abu Dayyeh |
| 2017/0071780 A1 | 3/2017 | Fong et al. |
| 2017/0087343 A1 | 3/2017 | Assaf et al. |
| 2017/0189217 A1 | 7/2017 | Folan et al. |
| 2017/0265849 A1 | 9/2017 | Assaf et al. |
| 2017/0333042 A1 | 11/2017 | Sato |
| 2018/0114591 A1 | 4/2018 | Pribanic et al. |
| 2018/0235631 A1 | 8/2018 | Khosrovaninejad |
| 2019/0224005 A1 | 7/2019 | McDonald |
| 2019/0224484 A1 | 7/2019 | Pierce et al. |
| 2020/0146550 A1 | 5/2020 | Tunnell et al. |
| 2020/0338808 A1 | 10/2020 | Hulseman et al. |
| 2020/0342979 A1 | 10/2020 | Sadowsky et al. |
| 2021/0001019 A1 | 1/2021 | Elder et al. |
| 2021/0008336 A1 | 1/2021 | Rajagopalan et al. |
| 2021/0020294 A1 | 1/2021 | Bharmi et al. |
| 2021/0038224 A1 | 2/2021 | Khosrovaninejad |
| 2021/0145624 A1 | 5/2021 | Fong et al. |
| 2021/0315578 A1 | 10/2021 | Khosrovaninejad et al. |
| 2022/0105320 A1 | 4/2022 | Göbel |
| 2022/0250254 A1 | 8/2022 | Hulseman et al. |
| 2022/0355017 A1 | 11/2022 | DePierro |
| 2022/0361880 A2 | 11/2022 | Khosrovaninejad et al. |
| 2024/0058008 A1 | 2/2024 | Morris et al. |

FOREIGN PATENT DOCUMENTS

| | | |
|---|---|---|
| CN | 103764069 A | 4/2014 |
| CN | 204169953 U | 2/2015 |
| CN | 108261577 A | 7/2018 |
| EP | 1405612 A1 | 4/2004 |
| EP | 2143389 A1 | 1/2010 |
| EP | 2165665 A1 | 3/2010 |
| EP | 2143388 B1 | 6/2011 |
| EP | 1556097 B1 | 8/2011 |
| EP | 1746941 B1 | 11/2011 |
| EP | 2395942 A1 | 12/2011 |
| EP | 2347723 B1 | 12/2012 |
| EP | 2286739 B1 | 1/2013 |
| EP | 2604195 A1 | 6/2013 |
| EP | 1492585 B1 | 6/2016 |
| EP | 2143387 B1 | 12/2016 |
| EP | 1647231 B1 | 11/2017 |
| FR | 2846868 A1 | 5/2004 |
| FR | 2941858 A1 | 8/2010 |
| JP | 2000316979 A | 11/2000 |
| JP | 2005519709 A | 7/2005 |
| JP | 2005524485 A | 8/2005 |
| JP | 2007069003 A | 3/2007 |
| JP | 2007513685 A | 5/2007 |
| JP | 2010502289 A | 1/2010 |
| JP | 2012517255 A | 8/2012 |
| WO | WO-03094785 A1 | 11/2003 |
| WO | WO-2007045229 A1 | 4/2007 |
| WO | WO-2008030403 A1 | 3/2008 |
| WO | WO-2008039223 A1 | 4/2008 |
| WO | WO-2010002291 A1 | 1/2010 |
| WO | WO-2010009291 A1 | 1/2010 |
| WO | WO-2010092291 A1 | 8/2010 |
| WO | WO-2011085234 A1 | 7/2011 |
| WO | WO-2011120047 A1 | 9/2011 |
| WO | WO-2013014353 A1 | 1/2013 |
| WO | WO-2013014355 A1 | 1/2013 |
| WO | WO-2013026474 A1 | 2/2013 |
| WO | WO-2014193949 A2 | 12/2014 |
| WO | WO-2015089505 A2 | 6/2015 |
| WO | WO-2017156039 A1 | 9/2017 |
| WO | WO-2017191500 A1 | 11/2017 |
| WO | WO-2017201504 A1 | 11/2017 |
| WO | WO-2018089773 A1 | 5/2018 |
| WO | WO-2019077218 A1 | 4/2019 |
| WO | WO-2020039442 A1 | 2/2020 |
| WO | WO-2020152640 A1 | 7/2020 |
| WO | WO-2024194771 A2 | 9/2024 |

OTHER PUBLICATIONS

Extended European Search Report for European Application No. 22170158.4, mailed Oct. 11, 2022, 8 pages.

International Search Report and Written Opinion dated Aug. 19, 2022 in Int'l PCT Patent Application Serial No. PCT/US2022/026558, 10 pages.

International Search Report and Written Opinion dated Mar. 20, 2019 in Int'l PCT Appl. Serial No. PCT/FR2018/052388, 06 pages.

International Search Report and Written Opinion dated May 7, 2010 in Int'l PCT Patent Application Serial No. PCT/FR2010/050210, 6 pages.

International Search Report and Written Opinion dated Sep. 4, 2012 in Int'l PCT Patent Appl. Serial No. PCT/FR2012/051576, 7 pages.

International Search Report and Written Opinion from corresponding PCT Application No. PCT/FR2020/050889, Sep. 10, 2020, 6 pages.

Moon CM., et al., "Comparison of a Newly Designed Double-Layered Combination Covered Stent and D-Weave Uncovered Stent for Decompression of Obstructive Colorectal Cancer: A Prospective Multicenter Study", Dis Colon Rectum, 2010, vol. 53, pp. 1190-1196.

Mukai, et al., The economic burdens of anastomotic leakage for patients undergoing colorectal surgery in Japan, Asian Journal of Surgery, 46:4323-4329 (2023).

Shim CS., et al., "Through-the-Scope Double Colonic Stenting in the Management of Inoperable Proximal Malignant Colonic Obstruction: a Pilot Study", Endoscopy, 36(05):426-431 (May 2004).

Shomura Y., et al., "Composite Material Stent Comprising Metallic Wire and Polylactic Acid Fibers, and Its Mechanical Strength and Retrievability", Acta Radiol., May 2009, vol. 50, No. 4, pp. 355-359.

(56) References Cited

OTHER PUBLICATIONS

International Search Report and Written Opinion dated Oct. 2, 2024 in Int'l PCT Patent Appl. Serial No. PCT/IB2024/052550.
Invitation to Pay Additional Fees and Partial Search Report dated Jun. 28, 2024 in Int'l PCT Patent Appl. Serial No. PCT/IB2024/052550.

* cited by examiner

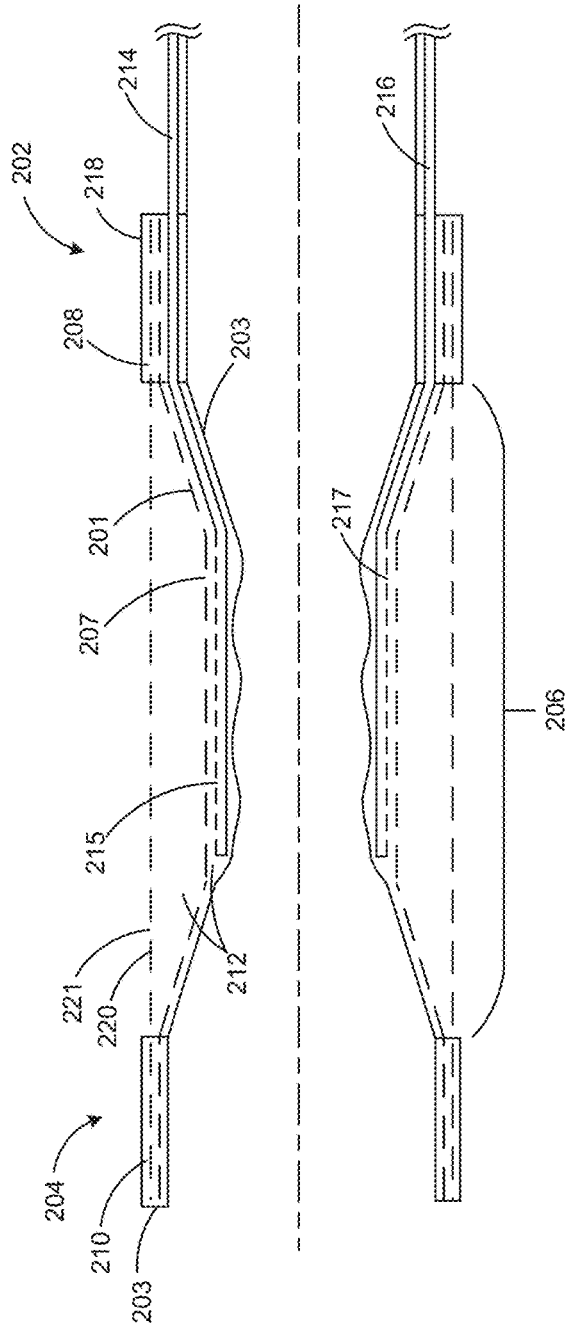
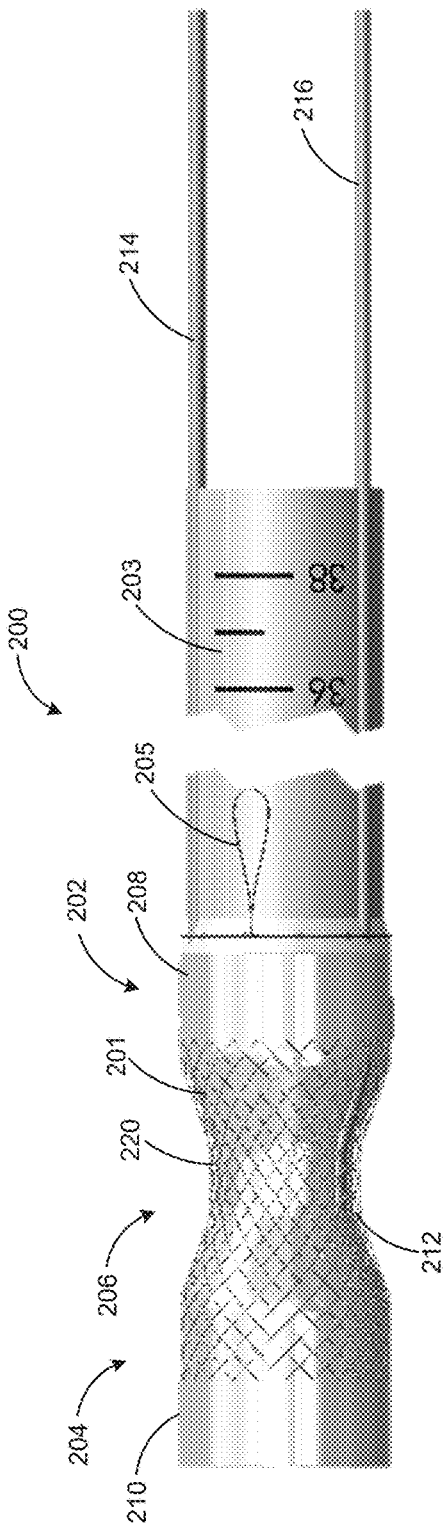
FIG. 2B
FIG. 2C

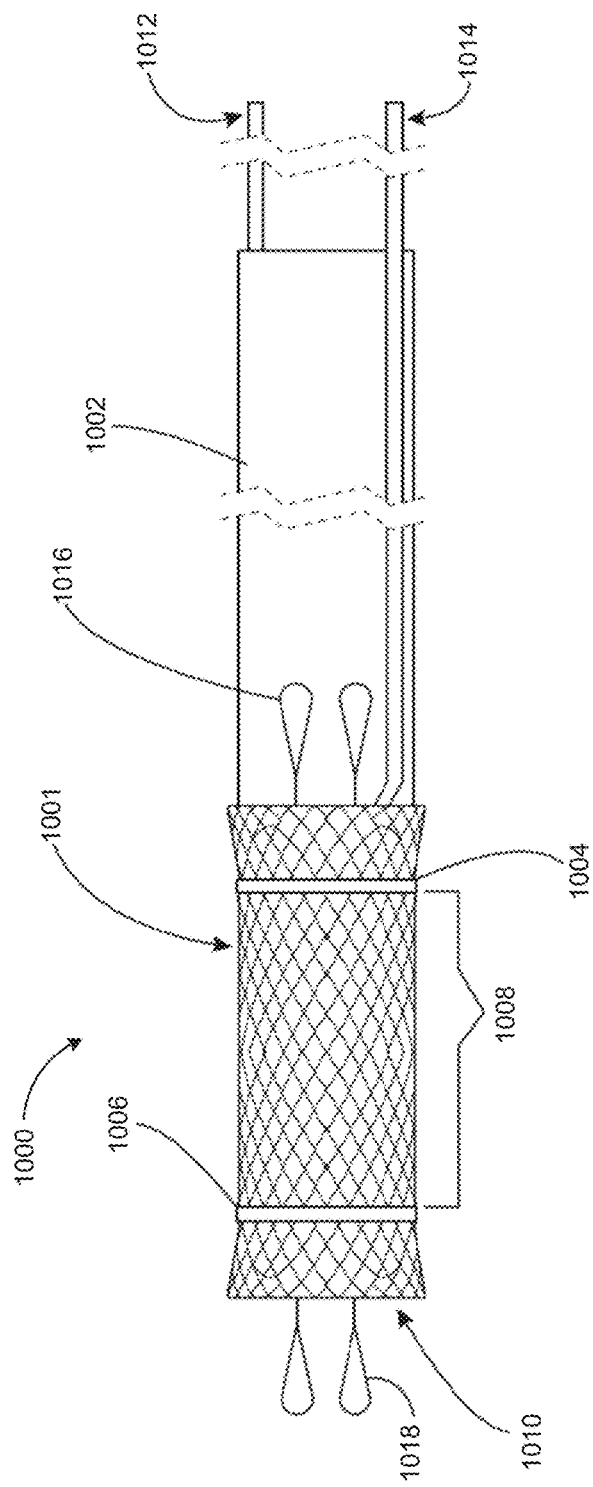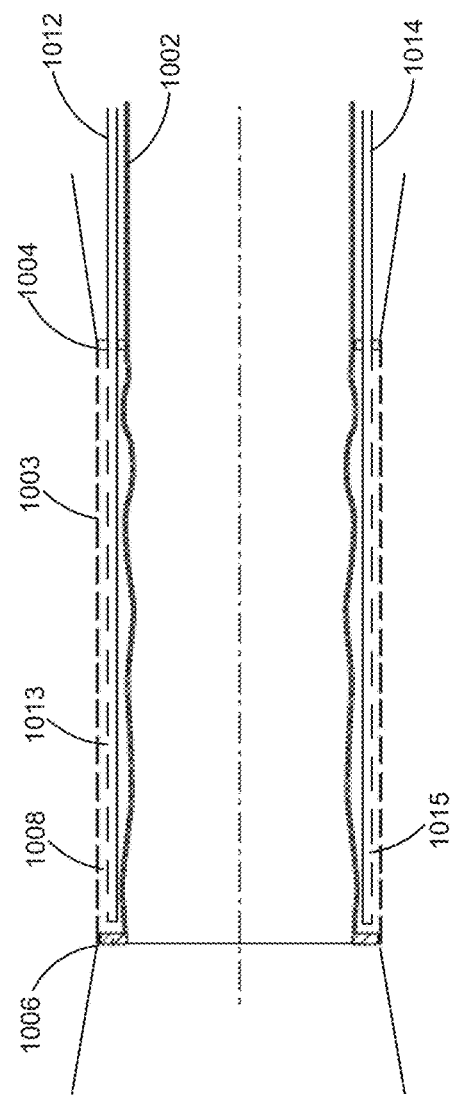
FIG. 10A
FIG. 10B

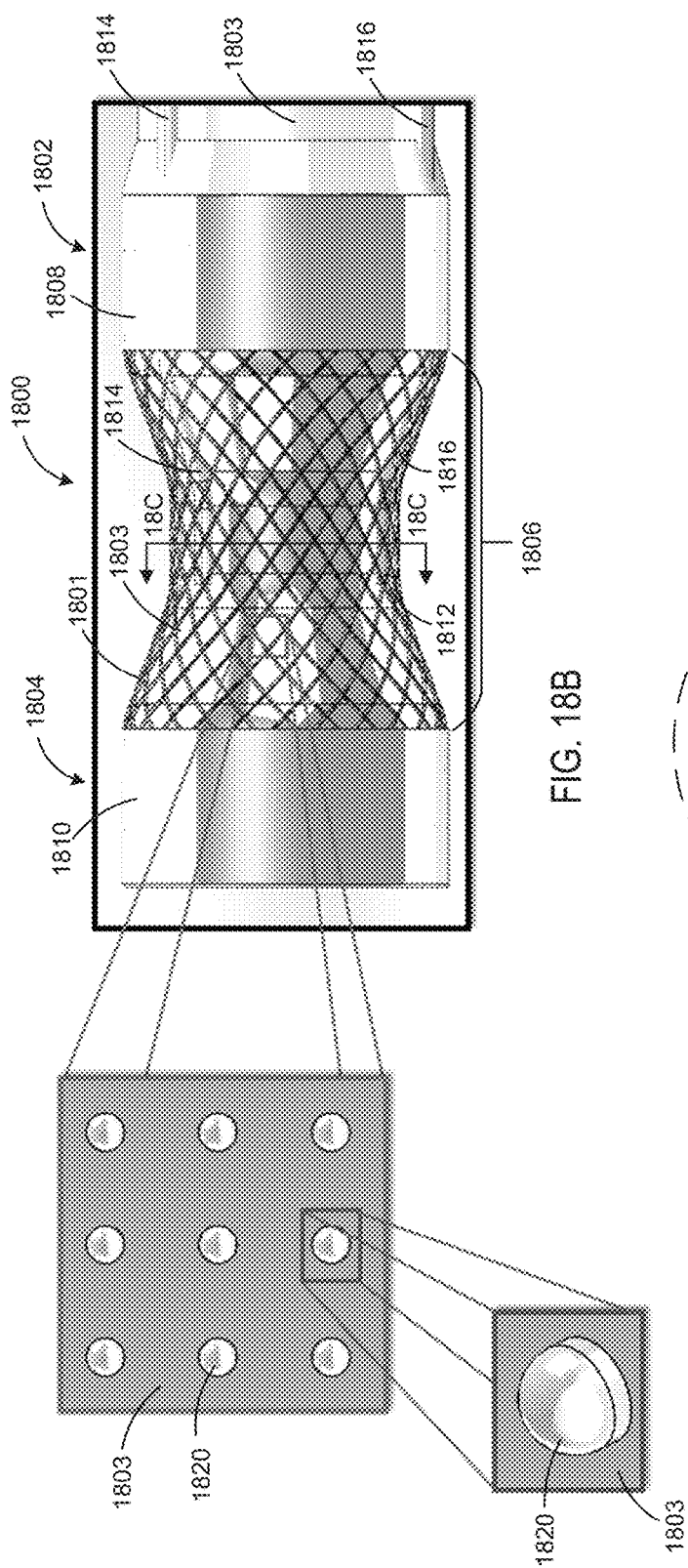
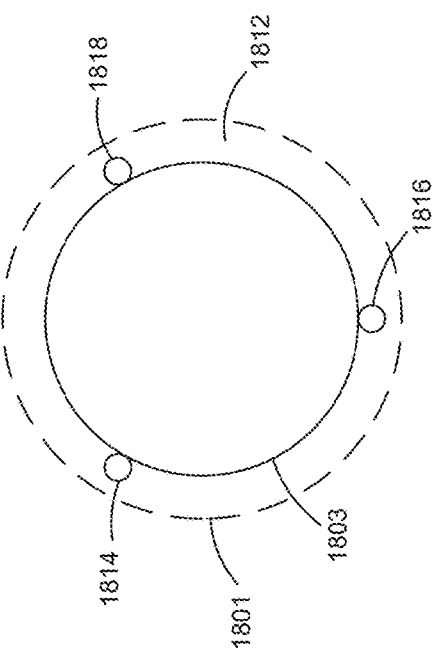
FIG. 18B
FIG. 18C

SYSTEMS AND METHODS FOR INTRODUCING AND MONITORING A NEGATIVE PRESSURE DEVICE FOR PROTECTING AN INTESTINAL ANASTOMOSIS

CROSS-REFERENCE TO RELATED APPLICATIONS

This application claims priority to U.S. Provisional Patent Application No. 63/589,965, filed Oct. 12, 2023, U.S. Provisional Patent Application No. 63/589,973, filed Oct. 12, 2023, U.S. Provisional Patent Application No. 63/490,847, filed Mar. 17, 2023, and European Patent Application No. 23305367.7, filed Mar. 17, 2023, the entire contents of each of which are incorporated herein by reference.

FIELD OF USE

This technology relates to systems and methods for introducing and monitoring an internal bypass device having a negative pressure system to protect against leakage in an anastomosis site following a bowel resection procedure.

BACKGROUND

In some instances, a segment of a patient's bowel must be removed to treat certain blockages and diseases, such as colorectal cancer, diverticulitis, severe bleeding, obstructions, and the like. In these bowel resection procedures, a physician dissects and removes a diseased or obstructed portion of the large intestine and then reconnects the healthy ends of the intestine with tiny staples or sutures, often referred to as a bowel anastomosis. The most serious complication occurring with bowel resection procedures is anastomotic leakage, which can occur when the healing process is delayed or incomplete. Anastomotic leakage allows feces and other waste matter to leak into the abdominal cavity, which can lead to a dangerous infection or sepsis. To prevent this from occurring, the anastomosis site must be protected immediately after surgery.

Traditionally, to prevent anastomotic leakage, surgeons create an external bypass of the anastomosis site, referred to as a diverting ostomy. In this procedure, the surgeon creates a temporary opening or stoma, (e.g., an artificial anus) to divert the intestines to this opening. The surgeon then attaches an ostomy bag to the opening in the abdomen to collect the patient's feces and other waste matter during the healing period. Unfortunately, ostomies are debilitating for patients, prone to complications, and costly and inefficient in terms of patient management. In addition, ostomies require a second surgery to reverse.

To overcome the limitations of diverting ostomy procedures, internal temporary bypass devices have been created. These bypass devices typically include a flexible sheath that is introduced into the colon and placed against the internal walls of the colon at the anastomosis site. The bypass device eliminates any contact between the tissue and feces or other waste matter traveling through the intestines, thereby ensuring the cleanliness of the anastomosis. After healing is complete, the sheath can be removed from the patient through a routine endoscopic procedure without requiring a second surgery.

One of the challenges with internal bypass devices is ensuring that they remain in secure contact with the bowel tissue around the anastomosis to prevent migration of the sheath or any leakage of bowel contents around the sheath and into the patient's abdomen. To overcome this challenge, bypass devices may include a negative suction or vacuum pressure system that provides a continuous negative pressure to the external walls of the sheath such that the sheath remains in close contact with the internal walls of the bowel around the anastomosis site. This negative suction pressure is typically supplied to the peripheral walls of the sheath with one or more fluid lines or catheters. The fluid lines are coupled to an external source of negative pressure, such as a suction canister or the like.

While these new bypass devices have been extremely effective, they suffer from certain drawbacks. For example, continuous suction pressure must be applied to the bypass sheath throughout the entire healing period. If any part of the pressure system suffers a loss in negative pressure, the outer walls of the sheath may lose contact with the intestines and allow migration of the sheath and/or leakage of feces or waste matter through the anastomosis. Accordingly, the pressure of the suction system must be constantly monitored. In the event of a loss of negative pressure, a health care practitioner must be immediately alerted so that the system can be replaced before the sheath ceases to function as intended.

Another drawback with existing negative pressure systems designed for use with internal bypass devices is that the suction canisters are typically supplied with negative pressure by a separate vacuum device. Therefore, to provide patient mobility during the healing period in the hospital, the storage canisters must either be disconnected from the vacuum device altogether or the patient must move around with the entire system. This not only subjects the patient to traveling with more devices but also with extra tubing, which must be clipped and secured to prevent falls. These troublesome systems are inconvenient to the patient, or to the therapists who assist them in movement.

To further enhance patient mobility, suction canisters have been designed that can be previously supplied with negative pressure prior to use by the patient. Since these suction canisters already have a negative or vacuum pressure, they do not require attachment to a separate tube for connection to the vacuum source. Although this provides some improvement in patient mobility, a suction canister alone is typically difficult for the patient to easily grip and carry. An improved system for monitoring negative pressure devices is described in U.S. Patent Application Pub. No. 2022/0355017 to DePierro, the entire contents of which are incorporated herein by reference.

In view of the foregoing drawbacks of previously known systems and methods, there exists a need for improved systems and methods for protecting an anastomosis site after bowel resection surgery, and monitoring the system. It would be further desirable to provide systems that are portable to allow the patient to be mobile during the recovery period to enhance GI motility and improve the patient's overall quality of life during this period.

SUMMARY

The present disclosure overcomes the drawbacks of previously-known systems and methods by providing a system for monitoring a bypass device for protecting an intestinal anastomosis, the bypass device comprising a negative pressure chamber and configured to be implanted at a target location upstream of the intestinal anastomosis. For example, the system may include a pump, one or more fluid inlet tubes each having a downstream end coupled to the pump and an upstream end having one or more pores in fluid communication with the negative pressure chamber of the bypass device, one or more sensors configured to measure data indicative of pressure within the negative pressure chamber, and a controller operatively coupled to the pump and the one or more sensors. The controller may be programmed with instructions configured to: actuate the pump at pump parameters to evacuate fluid from the negative pressure chamber via the one or more fluid inlet tubes to generate a vacuum within the negative pressure chamber having a pressure within a predetermined pressure range, the vacuum sufficient to pull intestinal tissue toward to bypass device to anchor the bypass device at the target location upstream of the intestinal anastomosis; compare the data indicative of the pressure within the negative pressure chamber received from the one or more sensors over time with the predetermined pressure range; and adjust, if the pressure within the negative pressure chamber falls outside the predetermined pressure range, the pump parameters of the pump, such that the pump applies and maintains the vacuum within the predetermined pressure range within the negative pressure chamber.

For example, the controller may be programmed to generate an alert if the pressure within the negative pressure chamber falls outside the predetermined pressure range. Additionally, or alternatively, the controller may be programmed to generate an alert if the pressure within the negative pressure chamber does not fall within the predetermined pressure range within a predetermined time period. The alert may be, for example, at least one of an audible or visual alert. The controller further may be programmed to adjust the predetermined pressure range of the vacuum over time. In addition, the controller further may be programmed to stop actuation of the pump when the pressure within the negative pressure chamber is within the predetermined pressure range. For example, the system further may include one or more check valves in fluid communication with the pump, the one or more check valves configured to transition between a closed state and an open state to bring the pump to ambient pressure.

The controller further may be configured to calculate an actual pump run time of the pump to achieve a predetermined total volume of the system, and determine a presence of an occlusion in the system if the actual pump run time deviates from an expected pump run time. Moreover, the controller may be configured to calculate a volume of the system in real time based on the data measured by the one or more sensors, such that the controller may be configured to calculate the expected pump run time of the pump based on the volume of the system in real time. The controller may be configured to generate an alert upon determination of the presence of the occlusion in the system. The system further may include a fluid reservoir chamber in fluid communication with the one or more fluid inlet tubes. The fluid reservoir chamber may be sized and shaped to collect at least one of liquid or solid waste from the fluid evacuated from the negative pressure chamber. For example, the one or more sensors may comprise a pressure transducer operatively coupled to the fluid reservoir chamber.

In some embodiments, the system may include a sensor configured to measure data indicative of a level of the at least one of liquid or solid waste within the fluid reservoir chamber, such that the controller may be programmed to generate an alert if the level of the at least one of liquid or solid waste exceeds a predetermined threshold. The one or more fluid inlet tubes may be operatively coupled to a pressure transducer operatively coupled to the controller, the pressure transducer configured to measure data indicative of pressure within the fluid reservoir chamber. Accordingly, the controller may be configured to compare the data indicative of the pressure within the negative pressure chamber received from the one or more sensors and the data indicative of the pressure within the fluid reservoir chamber received from the pressure transducer, and determine a presence of an occlusion in the one or more fluid inlet tubes if a pressure differential between the pressure within the negative pressure chamber and the fluid reservoir chamber falls below a predetermined pressure threshold. The controller further may be programmed to generate an alert upon determination of the presence of the occlusion in the one or more fluid inlet tubes.

The one or more fluid inlet tubes may be operatively coupled to a pressure transducer operatively coupled to the controller, the pressure transducer configured to measure data indicative of pressure within the fluid reservoir chamber. Accordingly, the controller may be configured to compare the data indicative of the pressure within the negative pressure chamber received from the one or more sensors and the data indicative of the pressure within the fluid reservoir chamber received from the pressure transducer, and determine a presence of an occlusion in the one or more fluid inlet tubes if a pressure differential between the pressure within the negative pressure chamber and the pressure within fluid reservoir chamber falls below a predetermined pressure threshold. The controller further may be programmed to generate an alert upon determination of the presence of the occlusion in the one or more fluid inlet tubes.

Moreover, the system may include a pressure normalization chamber fluidly coupled to the pump, and a valve fluidly coupled to the fluid reservoir chamber and pressure normalization chamber, wherein the valve may be operatively coupled to the controller and transitionable between a closed state and an open state. Additionally, the system may include a check valve fluidicly coupled to the pressure normalization chamber, wherein the check valve may be operatively coupled to the controller and transitionable between a closed configuration and an open configuration to bring the pressure normalization chamber to atmospheric pressure. Accordingly, the one or more sensors may be fluidly coupled to at least one of the fluid reservoir chamber or the pressure normalization chamber. Additionally, or alternatively, the one or more sensors may be disposed on the bypass device.

The system further may include a housing configured to contain at least the pump and the controller therein. For example, the housing may be sized and shaped to be worn by a patient, and/or the housing may be configured to be mounted bedside or on an IV pole. The housing may include a user interface operatively coupled to the controller. For example, the user interface may be configured to permit a user to select the pump parameters from a plurality of pump parameters. In addition, the user interface may include a display for displaying information associated with the bypass device. Moreover, the negative pressure chamber may be defined by a mesh anchor sealed to an inner sheath via a downstream seal and an upstream seal. The mesh anchor may be configured to engage with the intestinal tissue in an expanded deployed state, and the one or more fluid inlet tubes may extend across the downstream seal such that the one or more pores are disposed within the negative pressure chamber. In addition, the inner sheath may have a length such that the inner sheath extends from the mesh anchor at the target location across the intestinal anastomosis and out of an anal orifice, and may have a lumen sized and shaped to permit feces to pass therethrough without contacting the intestinal anastomosis.

In some embodiments, the mesh anchor may comprise a downstream region, an upstream region, and a middle region extending between the downstream and upstream regions, wherein the middle region has an outer diameter less than outer diameters of the downstream and upstream regions. Moreover, the system further may include a middle seal configured to seal the inner sheath to the middle region of the mesh anchor to thereby define a first negative pressure chamber between the inner sheath, the downstream seal, the middle seal, and a portion of the mesh anchor between the downstream seal and the middle seal, and a second negative pressure chamber between the inner sheath, the upstream seal, the middle seal, and a portion of the mesh anchor between the upstream seal and the middle seal. Accordingly, a first set of the one or more fluid inlet tubes may extend across the downstream seal such that one or more pores of the first set of the one or more fluid inlet tubes are disposed within the first negative pressure chamber, and a second set of the one or more fluid inlet tubes may extend across the downstream seal and the middle seal such that one or more pores of the second set of the one or more fluid inlet tubes are disposed within the second negative pressure chamber.

The middle seal may comprise a sealing ring having a plurality of inlet ports configured to be fluidicly coupled to the pump via one or more suction tubes. Moreover, the downstream seal may comprise a scaling ring having a plurality of inlet ports configured to be fluidicly coupled to the pump via one or more suction tubes. In some embodiments, the upstream seal may extend along an upstream region of the mesh anchor and may cover an upstream end of the mesh anchor. Accordingly, the upstream seal may be configured to inhibit mucosal ingrowth on the bypass device and inhibit damage to the intestinal tissue. Similarly, the downstream seal may extend along a downstream region of the mesh anchor and may cover a downstream end of the mesh anchor. Accordingly, the downstream seal may be configured to inhibit mucosal ingrowth on the bypass device and inhibit damage to the intestinal tissue.

The mesh may comprise an inner mesh anchor comprising a downstream region, an upstream region, and a middle region extending between the downstream and upstream regions, the middle region having an outer diameter less than outer diameters of the downstream and upstream regions, and an outer mesh anchor disposed over the inner mesh anchor. The outer mesh anchor may be configured to transition from a cylindrical configuration towards a shape corresponding to a geometry of the inner mesh anchor when the vacuum is generated within the negative pressure chamber. The system further may include one or more additional sensors configured to measure data indicative of a presence of at least one of blood, feces, or predefined gases between the bypass device and intestinal tissue surrounding the bypass device. Accordingly, the controller may be programmed to generate an alert if the level of the at least one of blood, feces, or predefined gases exceeds a predetermined threshold. Additionally, the system may include one or more additional sensors configured to measure data indicative of a position of the bypass device relative to the intestinal anastomosis. Accordingly, the controller may be programmed to generate an alert if the position of the bypass device relative to the intestinal anastomosis indicates that the bypass device is slipping from the target location.

Moreover, the one or more fluid inlet tubes may include a first fluid inlet tube having a first downstream end coupled to the pump and a first upstream end having a first set of one or more pores in fluid communication with the negative pressure chamber of the bypass device, and a second fluid inlet tube having a second downstream end coupled to the pump and a second upstream end having a second set of one or more pores in fluid communication with the negative pressure chamber of the bypass device. The first and second upstream ends of the first fluid and second fluid inlet tubes may be equally and circumferentially spaced apart within the negative pressure chamber. Additionally, the one or more sensors may include a sensing tube having a third downstream end coupled a vacuum transducer and a third upstream end in fluid communication with the negative pressure chamber of the bypass device. The first, second, and third upstream ends of the first fluid inlet tube, second fluid inlet tube, and sensing tube, respectively, may be equally and circumferentially spaced apart within the negative pressure chamber.

The system further may include a manifold configured to fluidicly couple the first and second fluid inlet tubes and the sensing tube to the pump and the vacuum transducer, respectively. The manifold may include a first inlet port and a first outlet port configured to receive the first fluid inlet tube therethrough, a second inlet port and a second outlet port configured to receive the second fluid inlet tube therethrough, a third inlet port configured to receive a downstream end of a distal portion of the sensing tube, a third outlet port configured to receive an upstream end of a proximal portion of the sensing tube therethrough, and a flushing port in fluid communication with the downstream end of the distal portion of the sensing tube and with the upstream end of the proximal portion of the sensing tube. The flushing port may be configured to receive fluid for flushing the tubes. In addition, the manifold may include a clamp disposed on the proximal portion of the sensing tube. The clamp may be configured to transition between an open state where fluid flow is permitted through an entire length of the sensing tube, and a closed state where fluid flow is inhibited within the sensing tube downstream of the clamp.

In accordance with another aspect of the present disclosure, a method for protecting an intestinal anastomosis is provided. The method may include: introducing a bypass device through an anal orifice into an intestine, and positioning the bypass device at a target location upstream of the intestinal anastomosis; deploying the bypass device at the target location; coupling a downstream end of one or more fluid inlet lines extending from a negative pressure chamber of the bypass device to a pump external to the anal orifice; actuating the pump at pump parameters to evacuate fluid from the negative pressure chamber via the one or more fluid inlet tubes to generate a vacuum having a pressure within a predetermined pressure range within the negative pressure chamber, the vacuum sufficient to pull intestinal tissue within the negative pressure chamber to anchor the bypass device at the target location; measuring pressure within the negative pressure chamber over time via one or more pressure sensors; and adjusting, if the pressure within the negative pressure chamber falls outside the predetermined pressure range, the pump parameters of the pump, such that the pump applies and maintains the vacuum within the predetermined pressure range within the negative pressure chamber.

For example, introducing the bypass device through the anal orifice into the intestine may include introducing a first tubular portion of a guide tube of an introducer device through the anal orifice. The first tubular portion may have the bypass device disposed therein in a collapsed delivery state. Moreover, deploying the bypass device at the target location may include rotating an actuator of a handle operatively coupled to a second tubular portion of the guide tube downstream to the first tubular portion, such that a slidable engagement between one or more notches of the handle and one or more grooves extending along an outer surface of the second tubular portion causes axial translation of the guide tube relative to the handle to thereby expose the bypass device beyond an upstream tip of the first tubular portion.

The method further may include generating, via a controller operatively coupled to the one or more sensors, an alert if the pressure within the negative pressure chamber falls outside the predetermined pressure range. Additionally, or alternatively, the method may include generating, via a controller operatively coupled to the one or more sensors, an alert if the pressure within the negative pressure chamber does not fall within the predetermined pressure range within a predetermined time period. In addition, the method may include stopping actuation of the pump when the pressure within the negative pressure chamber is within the predetermined pressure range. Moreover, the method may include collecting at least one of liquid or solid waste from the fluid evacuated from the negative pressure chamber within a reservoir in fluid communication with the one or more fluid inlet lines, monitoring a level of the at least one of liquid or solid waste within the reservoir, and generating an alert when the level of the at least one of liquid or solid waste within the reservoir exceeds a predetermined threshold.

In addition, the negative pressure chamber may be defined by a mesh anchor sealed to an inner sheath via a downstream seal and an upstream seal, the downstream seal extending along a downstream region of the mesh anchor and covering a downstream end of the mesh anchor, and the upstream seal extending along an upstream region of the mesh anchor and covering an upstream end of the mesh anchor. Accordingly, deploying the bypass device at the target location may include expanding the mesh anchor to an expanded deployed state, such that the upstream and downstream seals form a seal against the intestinal tissue. The upstream and downstream seals may inhibit mucosal ingrowth on the bypass device and inhibit damage to the intestinal tissue.

The mesh anchor may comprise an inner mesh anchor comprising a downstream region, an upstream region, and a middle region extending between the downstream and upstream regions, the middle region having an outer diameter less than outer diameters of the downstream and upstream regions, and an outer mesh anchor disposed over the inner mesh anchor. The outer mesh anchor may be configured to transition from a cylindrical configuration towards a shape corresponding to a geometry of the inner mesh anchor when the vacuum is generated within the negative pressure chamber, such that, upon actuation of the pump to generate the vacuum within the negative pressure chamber, the outer mesh anchor may transition from the cylindrical configuration towards the shape corresponding to the geometry of the inner mesh anchor. The method further may include calculating an actual pump run time of the pump to achieve a predetermined total volume of the system, and determining a presence of an occlusion in the system if the actual pump run time deviates from an expected pump run time. Adjusting, if the pressure within the negative pressure chamber falls outside the predetermined pressure range, the pump parameters of the pump may include automatically adjusting, via a controller operatively coupled to the one or more sensors and the pump, the pump parameters of the pump if the pressure within the negative pressure chamber falls outside the predetermined pressure range.

The method further may include measuring, via a pressure transducer, pressure within a fluid reservoir chamber in fluid communication with the one or more fluid inlet tubes, comparing the pressure within the negative pressure chamber and the pressure within the fluid reservoir chamber, and determining a presence of an occlusion in the one or more fluid inlet tubes if a pressure differential between the pressure within the negative pressure chamber and the pressure within fluid reservoir chamber falls below a predetermined pressure threshold. Accordingly, the method may include generating, via the controller, an alert upon determination of the presence of the occlusion in the one or more fluid inlet tubes. In addition, the method may include flushing, via a manifold fluidicly coupling the one or more fluid inlet tubes to the negative pressure chamber and the pump, the one or more fluid inlet tubes to remove the occlusion. In some embodiments, the one or more fluid inlet tubes may include first and second fluid inlet tubes extending from the negative pressure chamber of the bypass device to the pump. Moreover, measuring pressure within the negative pressure chamber over time via one or more pressure sensors may include measuring, via a vacuum transducer, pressure within the negative pressure chamber over time via a sensing tube extending from the negative pressure chamber to the vacuum transducer.

In accordance with yet another aspect of the present disclosure, a bypass device configured to be implanted at a target location upstream of an intestinal anastomosis for protecting the intestinal anastomosis is provided. The bypass device may include an inner mesh anchor comprising a downstream region, an upstream region, and a middle region extending between the downstream and upstream regions, the middle region having an outer diameter less than outer diameters of the downstream and upstream regions, an outer mesh anchor disposed over the inner mesh anchor, the outer mesh anchor configured to transition between a cylindrical configuration configured to engage an inner wall of an intestine and a shape corresponding to a geometry of the inner mesh anchor, a sheath at least partially disposed within the inner mesh anchor and coupled to the inner and outer mesh anchors to define a negative pressure chamber between an outer surface of the sheath and the inner wall of the intestine. The sheath may have a lumen sized and shaped to permit feces to pass therethrough without contacting the intestinal anastomosis. Accordingly, upon application of negative pressure within the negative pressure chamber, the outer mesh anchor may be configured to transition from the cylindrical configuration towards the shape corresponding to the geometry of the inner mesh anchor. The geometry of the inner mesh anchor may comprise an hourglass shape.

In addition, the sheath may comprise a length such that the sheath extends from the inner and outer mesh anchors at the target location across the intestinal anastomosis and out of an anal orifice. Moreover, the sheath may be sealed to upstream and downstream regions of the inner and outer mesh anchors via an upstream seal and a downstream seal, respectively, to thereby define the negative pressure chamber between the outer surface of the sheath, the upstream and downstream seals, and the inner wall of the intestine. In some embodiments, an upstream region of the sheath may extend through a lumen of the inner mesh anchor and wrap around upstream ends of the inner and outer mesh anchor, such that the upstream region of the sheath sandwiches the upstream regions of the inner and outer mesh anchors. Accordingly, the upstream seal may thermally bond upstream regions of the sheath, the inner mesh anchor, and the outer mesh anchor. Further, the upstream seal may be configured to inhibit mucosal ingrowth at the upstream regions of the inner and outer mesh anchors and inhibit damage to intestinal tissue surrounding the bypass device.

The bypass device further may include a sheath material disposed over the downstream region of the outer mesh anchor, such that the downstream seal may thermally bond the sheath material and downstream regions of the sheath, the inner mesh anchor, and the outer mesh anchor. Additionally, the downstream seal may be configured to inhibit mucosal ingrowth at the downstream regions of the inner and outer mesh anchors and inhibit damage to intestinal tissue surrounding the bypass device.

In addition, the bypass device may include one or more fluid inlet tubes each having a downstream end coupled to a pump and an upstream end having one or more pores in fluid communication with the negative pressure chamber. For example, the one or more fluid inlet tubes may extend across the downstream seal such that the one or more pores are disposed within the negative pressure chamber. The bypass device further may include one or more check valves in fluid communication with the pump. The one or more check valves may be configured to transition between a closed state and an open state to bring the pump to ambient pressure. Moreover, a first set of the one or more fluid inlet tubes may extend across the downstream seal such that one or more pores of the first set of the one or more fluid inlet tubes are disposed within the first negative pressure chamber, and a second set of the one or more fluid inlet tubes may extend across the downstream seal and the middle seal such that one or more pores of the second set of the one or more fluid inlet tubes are disposed within the second negative pressure chamber. Upstream ends of the one or more fluid inlet tubes may be equally and circumferentially spaced apart within the negative pressure chamber.

The bypass device further may include a housing configured to contain at least the pump therein. For example, the housing may be sized and shaped to be worn by a patient. The housing may comprise a user interface configured to permit a user to select pump parameters of the pump from a plurality of predetermined pump parameters. Moreover, the user interface may comprise a display for displaying information associated with the bypass device. The bypass device further may include one or more sensors configured to measure data indicative of pressure within the negative pressure chamber. Moreover, the bypass device may include a controller operatively coupled to the pump and the one or more sensors. The controller may be programmed with instructions configured to: actuate the pump at predetermined pump parameters to evacuate fluid from the negative pressure chamber via the one or more fluid inlet tubes to generate a vacuum within the negative pressure chamber having a pressure within a predetermined pressure range, the vacuum sufficient to pull intestinal tissue toward the bypass device to anchor the bypass device at the target location upstream of the intestinal anastomosis; compare the data indicative of the pressure within the negative pressure chamber received from the one or more sensors over time with the predetermined pressure range; and adjust, if the pressure within the negative pressure chamber falls outside the predetermined pressure range, the predetermined pump parameters of the pump, such that the pump applies and maintains the vacuum within the predetermined pressure range within the negative pressure chamber.

In addition, the controller may be configured to: calculate an actual pump run time of the pump to achieve a predetermined total volume of the system; and determine a presence of an occlusion in the system if the actual pump run time deviates from an expected pump run time. For example, the controller may be configured to calculate a volume of the system in real time based on the data measured by the one or more sensors, such that the controller may be configured to calculate the expected pump run time of the pump based on the volume of the system in real time. Alternatively, the expected pump run time may be predetermined. The controller may be configured to generate an alert upon determination of the presence of the occlusion in the system. Additionally, the controller may be configured to generate an alert if the pressure within the negative pressure chamber falls outside the predetermined pressure range.

The bypass device further may include one or more additional sensors configured to measure data indicative of a presence of at least one of blood, feces, or predefined gases between the bypass device and intestinal tissue surrounding the bypass device. Accordingly, the controller may be configured to generate an alert if the level of the at least one of blood, feces, or predefined gases exceeds a predetermined threshold. Additionally, the bypass device further may include one or more additional sensors configured to measure data indicative of a position of the bypass device relative to the intestinal anastomosis. Accordingly, the controller may be configured to generate an alert if the position of the bypass device relative to the intestinal anastomosis indicates that the bypass device is slipping from the target location. Moreover, prior to application of the negative pressure within the negative pressure chamber, the inner mesh anchor may exhibit an hourglass configuration and the outer may exhibit the cylindrical configuration, and upon application of the negative pressure within the negative pressure chamber while at the target location within the intestine, the outer mesh anchor and the inner mesh anchor may both exhibit the hourglass configuration.

In accordance with another aspect of the present disclosure, a method for protecting an intestinal anastomosis is provided. The method may comprise: positioning a bypass device at a target location upstream of the intestinal anastomosis of a patient, the bypass device comprising an inner mesh anchor, an outer mesh anchor disposed over the inner mesh anchor, and a sheath at least partially disposed within the inner mesh anchor and coupled to the inner and outer mesh anchors to define a negative pressure chamber between an outer surface of the sheath and the inner wall of the intestine, the inner mesh anchor comprising a downstream region, an upstream region, and a middle region extending between the downstream and upstream regions, the middle region having an outer diameter less than outer diameters of the downstream and upstream regions; and applying negative pressure within the negative pressure chamber, wherein, upon application of negative pressure within the negative pressure chamber, the outer mesh anchor transitions from a cylindrical configuration towards a shape corresponding to a geometry of the inner mesh anchor.

Prior to applying the negative pressure within the negative pressure chamber, the inner mesh anchor may exhibit an hourglass configuration and the outer may exhibit the cylindrical configuration, and, upon application of the negative pressure within the negative pressure chamber while at the target location within the intestine, the outer mesh anchor and the inner mesh anchor may both exhibit the hourglass configuration. Moreover, the method may comprise coupling a downstream end of one or more fluid inlet tubes extending from the negative pressure chamber of the bypass device to a pump external to an anal orifice of the patient. Accordingly, applying negative pressure within the negative pressure chamber may comprise actuating the pump at pump parameters to evacuate fluid from the negative pressure chamber via the one or more fluid inlet tubes to generate a vacuum having a pressure within a predetermined pressure range within the negative pressure chamber, the vacuum sufficient to pull intestinal tissue within the negative pressure chamber to anchor the bypass device at the target location. In addition, the method may comprise: measuring pressure within the negative pressure chamber over time via one or more pressure sensors; and adjusting, if the pressure within the negative pressure chamber falls outside the predetermined pressure range, the pump parameters of the pump, such that the pump applies and maintains the vacuum within the predetermined pressure range within the negative pressure chamber.

In accordance with yet another aspect of the present disclosure, a system for protecting an anastomosis in an intestine is provided. The system may include an anchor (e.g., a mesh stent) configured to be implanted at a target location in the intestine upstream of the anastomosis. The anchor may be configured to transition from a compressed state to an expanded state wherein an outer surface of the anchor contacts an inner wall of the intestine at the target location. The system further may include a sheath disposed within the anchor and coupled to the anchor to define a negative pressure chamber between an outer surface of the sheath and the inner wall of the intestine. The outer surface of the sheath may comprise a micropattern of microstructures configured to maintain a vacuum throughout the negative pressure chamber such that the anchor remains anchored at the target location when negative pressure is applied in the negative pressure chamber.

The anchor may comprise an inner mesh anchor comprising a downstream region, an upstream region, and a middle region extending between the downstream and upstream regions, the middle region having an outer diameter less than outer diameters of the downstream and upstream regions, and an outer mesh anchor disposed over the inner mesh anchor. The outer mesh anchor may be configured to transition from a cylindrical configuration towards a shape corresponding to a geometry of the inner mesh anchor when negative pressure is applied in the negative pressure chamber. For example, the sheath may be sealed to upstream and downstream regions of the inner and outer mesh anchors via an upstream seal and a downstream seal, respectively, to thereby define the negative pressure chamber between the outer surface of the sheath, the upstream and downstream seals, and the inner wall of the intestine. Prior to applying the negative pressure within the negative pressure chamber, the inner mesh anchor may exhibit an hourglass configuration and the outer may exhibit the cylindrical configuration, and, upon application of the negative pressure within the negative pressure chamber while at the target location within the intestine, the outer mesh anchor and the inner mesh anchor may both exhibit the hourglass configuration.

Moreover, each microstructure of the micropattern of microstructures may have a shape comprising a circular pillar, rectangle, triangle, square, sinusoid, or semi-spherical shape. The micropattern of microstructures may extend radially around a full circumference of the outer surface of the sheath and longitudinally along an entire length of the outer surface of the sheath within the negative pressure chamber. In addition, the sheath may extend downstream from the anchor, across the anastomosis, and out an anus. In some embodiments, the micropattern of microstructures is only on the outer surface of the sheath within the negative pressure chamber. Moreover, the micropattern of microstructures may be configured to inhibit the inner wall of the intestine from sealing against the outer surface of the sheath responsive to the vacuum to thereby encourage 360° fluidic communication within the negative pressure chamber.

The micropattern of microstructures may comprise a plurality of rows and a plurality of columns of microstructures throughout the negative pressure chamber. In some embodiments, the micropattern of microstructures may be arranged in a triangular or rectangular shape on the outer surface of the sheath within the negative pressure chamber. In addition, the outer surface of the sheath may comprises at least one of ribs or channels configured to guide fluid flow within the negative pressure chamber. Additionally, each microstructure of the micropattern of microstructures may have a cross-sectional width of between 50 and 500 microns, and a height of between 50 to 1000 microns. For example, each microstructure of the micropattern of microstructures may have a cross-sectional width of about 300 microns and a height of about 600 microns. Moreover, each microstructure of the micropattern of microstructures may be a protrusion configured to extend outwardly from the outer surface of the sheath towards the inner wall of the intestine.

The system further may comprise one or more fluid inlet tubes each having a downstream end coupled to a pump and an upstream end having one or more pores in fluid communication with the negative pressure chamber. For example, upstream ends of the one or more fluid inlet tubes may be equally and circumferentially spaced apart within the negative pressure chamber. Additionally, the system may comprise one or more sensors configured to measure data indicative of pressure within the negative pressure chamber. Further, the system may comprise a controller operatively coupled to the pump and the one or more sensors. The controller may be programmed with instructions configured to: actuate the pump at predetermined pump parameters to evacuate fluid from the negative pressure chamber via the one or more fluid inlet tubes to generate a vacuum within the negative pressure chamber having a pressure within a predetermined pressure range, the vacuum sufficient to pull intestinal tissue toward the anchor to maintain the anchor at the target location; compare the data indicative of the pressure within the negative pressure chamber received from the one or more sensors over time with the predetermined pressure range; and adjust, if the pressure within the negative pressure chamber falls outside the predetermined pressure range, the predetermined pump parameters of the pump, such that the pump applies and maintains the vacuum within the predetermined pressure range within the negative pressure chamber.

Moreover, the controller may be configured to generate an alert if the pressure within the negative pressure chamber falls outside the predetermined pressure range. The controller further may be configured to: calculate an actual pump run time of the pump to achieve a predetermined total volume of the system; and determine a presence of an occlusion in the system if the actual pump run time deviates from an expected pump run time. Accordingly, the controller may be configured to generate an alert upon determination of the presence of the occlusion in the system.

In accordance with another aspect of the present disclosure, a method for protecting an intestinal anastomosis. The method may comprise: positioning an anchor at a target location in the intestine upstream of the anastomosis, the anchor coupled to a sheath disposed within the anchor to define a negative pressure chamber between an outer surface of the sheath and an inner wall of the intestine; transitioning the anchor from a compressed state to an expanded state wherein an outer surface of the anchor contacts the inner wall of the intestine at the target location; and applying negative pressure in the negative pressure chamber, wherein the outer surface of the sheath comprises a micropattern of microstructures configured to maintain a vacuum throughout the negative pressure chamber when negative pressure is applied in the negative pressure chamber, such that the anchor remains anchored at the target location.

For example, the anchor may comprise an inner mesh anchor and an outer mesh anchor disposed over the inner mesh anchor, the inner mesh anchor comprising a downstream region, an upstream region, and a middle region extending between the downstream and upstream regions, the middle region having an outer diameter less than outer diameters of the downstream and upstream regions. Moreover, upon application of negative pressure in the negative pressure chamber, the outer mesh anchor may transition from a cylindrical configuration towards a shape corresponding to a geometry of the inner mesh anchor. Additionally, the sheath may be sealed to upstream and downstream regions of the inner and outer mesh anchors via an upstream seal and a downstream seal, respectively, to thereby define the negative pressure chamber between the outer surface of the sheath, the upstream and downstream seals, and the inner wall of the intestine. In some embodiments, the micropattern of microstructures may only be on the outer surface of the sheath between the upstream and downstream seals within the negative pressure chamber.

In accordance with another aspect of the present disclosure, an introducer device for delivering a bypass device into an intestine for protecting an intestinal anastomosis is provided. The introducer device may include a guide tube having a lumen, such that the guide tube comprises a first tubular portion configured to hold the bypass device therein in a collapsed delivery state, and a second tubular portion downstream to the first tubular portion. The first tubular portion may include an upstream tip configured to be introduced through an anal orifice into the intestine, and a length such that the upstream tip is positionable at a target position upstream of the intestinal anastomosis. Moreover, an outer surface of the second tubular portion may include one or more grooves. The introducer device further may include a handle operatively coupled to the second tubular portion via one or more features configured to slidably engage with the one or more grooves. In addition, the handle may include an actuator configured to be rotated to cause axial translation of the guide tube relative to the handle via the slidable engagement between the one or more features and the one or more grooves.

For example, the upstream tip of the first tubular portion may include a plurality of flexible cut-out tabs configured to transition between a closed tulip configuration and an open configuration. Moreover, the one or more grooves may extend in a circumferential and axial pattern along the outer surface of the second tubular portion, such that rotation of the actuator causes rotation of the one or more features relative to the second tubular portion such that movement of the one or more features along the one or more grooves causes axial translation of the guide tube relative to the handle. The outer surface of the second tubular portion further may include a linear track, and the handle further may include an engager configured to slidably engage with the linear track, such that engagement between the engager and the linear track prevents rotation of the guide tube relative to the handle as the guide tube axially translates relative to the handle.

The handle further may include one or more flexible tabs extending circumferentially along at least a portion of an outer surface of the handle. The one or more flexible tabs may be configured to transition between a radially compressed state and a radially expanded state. The one or more flexible tabs may be biased toward the radially expanded state. Moreover, an inner surface of the actuator may include one or more grooves configured to slidably engage with the one or more flexible tabs. The one or more grooves may have a profile comprising a stop feature such that rotation of the actuator in a first direction relative to the handle is permitted, while rotation of the actuator in a second direction opposite to the first direction relative to the handle is prevented upon engagement of the one or more flexible tabs and the stop feature in the radially expanded state.

The introducer device further may include a stop positioned between the first tubular portion and the second tubular portion. For example, the stop may have an outer diameter larger than an outer diameter of the first tubular portion. In addition, the introducer device may include a pusher having a downstream end coupled to the handle and an upstream end slidably disposed within the lumen of the guide tube at a position downstream to the bypass device in the collapsed delivery state, such that axial translation of the guide tube downstream relative to the handle causes the upstream end of the pusher to engage with and maintain the bypass device at the target position upstream of the intestinal anastomosis until the bypass device is exposed beyond the upstream tip of the guide tube and transitions to an expanded deployed state.

BRIEF DESCRIPTION OF THE DRAWINGS

FIG. 2B is a cross-sectional view of the implantable portion of the negative pressure bypass system of FIG. 2A.

FIG. 2C illustrates the implantable portion of the negative pressure bypass system of FIG. 2A under vacuum in accordance with the principles of the present disclosure.

FIGS. 10 to 15A illustrate alternative exemplary implantable portions of the negative pressure bypass system, constructed in accordance with the principles of the present disclosure.

FIGS. 18A and 18B illustrate an alternative exemplary implantable portion of the negative pressure bypass system having a micropattern of microstructures, constructed in accordance with the principles of the present disclosure.

FIG. 18C is a cross-sectional view of the middle region of the implantable portion of the negative pressure bypass system of FIG. 18B.

DETAILED DESCRIPTION

The present disclosure provides systems and devices for creating an internal bypass within a target area of the gastrointestinal (GI) tract of a patient to allow feces and other waste matter to pass through the target area without contacting the walls of the GI tract at the target area. The target area may be, for example, an anastomosis site in the colon, rectum, or anal passage created after bowel resection surgery to treat certain blockages and diseases, such as colorectal cancer, diverticulitis, severe bleeding, obstructions, and the like. The bypass device may be secured to a target site upstream of the anastomosis site via a negative pressure system including, for example, an external pump fluidicly coupled to a negative pressure chamber of the bypass device via suitable medical tubing, or the like. The external pump further may include a "smart" vacuum monitoring system that monitors the pressure within the negative pressure chamber, and automatically responds when the pressure within the negative pressure chamber falls outside of a predetermined range. For example, the smart vacuum monitoring system may automatically adjust the pump parameters and/or turn the pump on to maintain the pressure within the negative pressure chamber within the predetermined range. In addition, the smart vacuum monitoring system may generate an alert to inform a user when the pressure within the negative pressure chamber falls outside of the predetermined range. Accordingly, the systems described herein provide constant sensing and the ability to more rapidly and continuously maintain a specific vacuum threshold. The present disclosure further provides a delivery system for introducing the bypass device at the target area of the GI tract.

Figure 1:
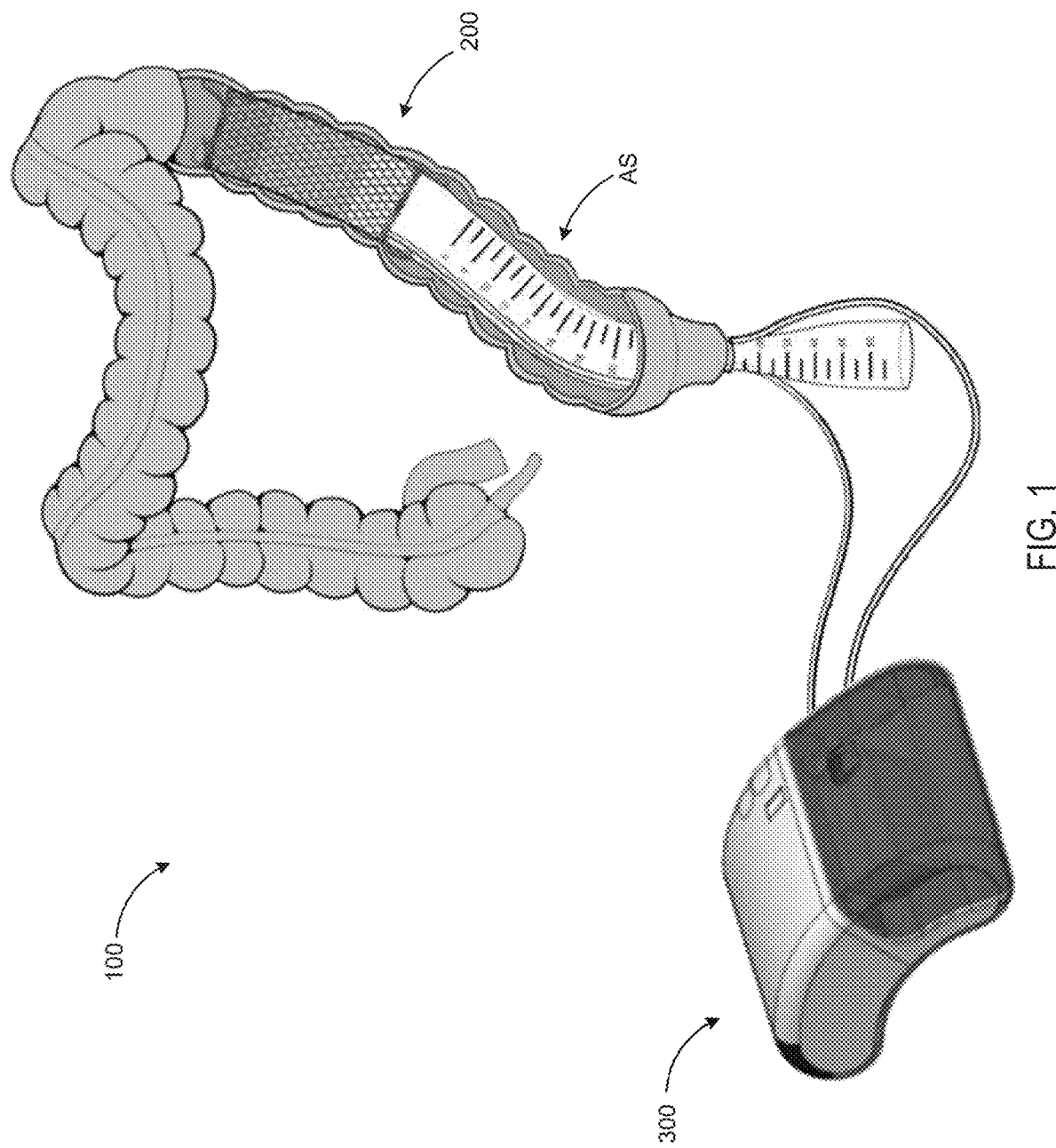
FIG. 1 illustrates an exemplary negative pressure bypass system implanted within a patient anatomy, constructed in accordance with the principles of the present disclosure.

Referring now to FIG. 1, system 100 for monitoring a bypass device for protecting an intestinal anastomosis is provided. As shown in FIG. 1, system 100 may include bypass device 200 configured to be anchored within a patient's GI tract, e.g., upstream of intestinal anastomosis AS, for allowing feces and other waste matter to pass through anastomosis AS without contacting the walls of the GI tract at anastomosis AS. For example, as described in further detail below, bypass device 200 may include an anchor for securing bypass device 200 at the location upstream of anastomosis AS via a negative pressure system, e.g., negative pressure system 300, fluidicly coupled to bypass device 200 external to the patient, as well as a sheath coupled to the anchor and extending through the GI tract across anastomosis AS and extending through the patient's anus, as shown in FIG. 1. The sheath may have a lumen sized and shaped to permit feces and other waste matter to pass therethrough.

Figure 2A:
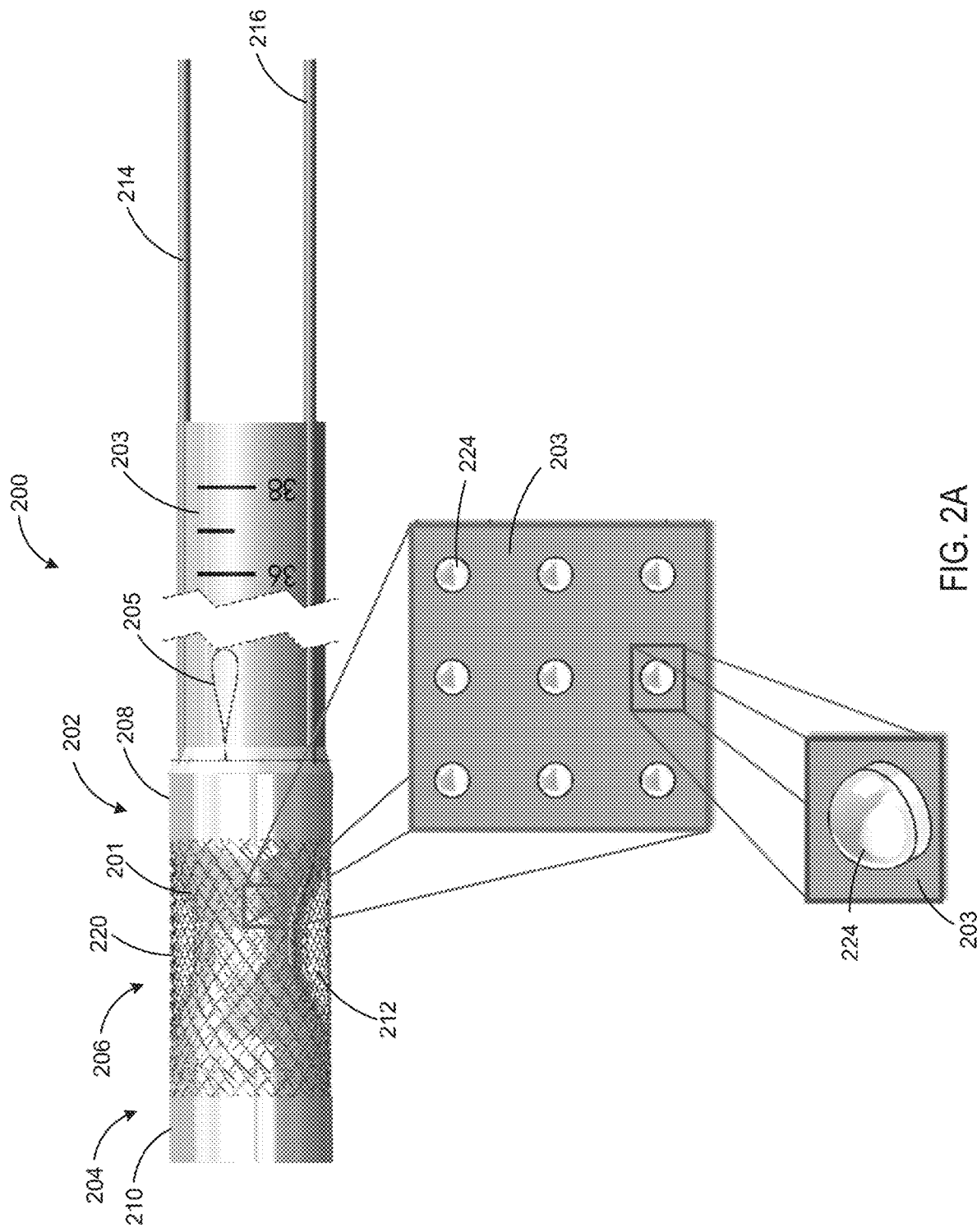
FIG. 2A illustrates the implantable portion of the negative pressure bypass system of FIG. 1 having a micropattern of microstructures.

Referring now to FIGS. 2A to 2C, bypass device 200 for providing an internal bypass at a target site within the GI tract of the patient is provided. As shown in FIG. 2A, bypass device 200 having flared downstream region 202, flared upstream region 204, and recessed middle region 206 extending between downstream region 202 and upstream region 204, may include inner anchor 201, outer anchor 220 disposed circumferentially around inner anchor 201, and elongated flexible sheath 203 coupled to inner and outer anchors 201, 220 and extending therefrom in a downstream direction. Inner and outer anchors 201, 220 may each be formed by a stent/scaffold, e.g., a self-expandable braided wire mesh. As shown in FIG. 2B, inner anchor 201 may have a pre-formed shape, e.g., an hourglass/bone shape, defining recessed middle region 206 of bypass device 200. For example, middle region 206 defined by inner anchor 201 may have an outer diameter that is less than the outer diameters of downstream region 202 and upstream region 204, thereby providing a larger volume between the outer surface of middle region 206 and the wall of the intestine to improve negative pressure chamber engagement with the intestinal tissue during application of the vacuum. Preferably, inner anchor 201 may be symmetric such that downstream region 202 may have an outer diameter that is equal to the outer diameter of upstream region 204. Outer anchor 220 may be configured to transition between a natural cylindrical configuration to a shape corresponding with inner anchor 201 when system 100 is under vacuum, as shown in FIG. 2C.

Inner and outer anchors 201, 220 may be coupled together at their respective upstream and downstream ends, as well as to a distal region of sheath 203. For example, as shown in FIG. 2B, an upstream region of sheath 203 may extend through the lumen of anchor 201 and wrap around the upstream ends of inner and outer anchors 201, 220, such that the upstream region of sheath 203 contacts the outer surface of an upstream region of outer anchor 220 and the inner surface of an upstream region of inner stent 201. Moreover, the upstream region of sheath 203 may be coupled to the upstream regions of inner and outer anchors 201, 220 via upstream sealing ring 210, which may extend along the periphery of the upstream ends of inner and outer anchors 201, 220, to thereby securely fasten sheath 203 to the upstream regions of inner and outer anchors 201, 220. In addition, sheath material 218 may be disposed circumferentially over a downstream region of outer anchor 220, such that a portion of sheath 203 may be coupled to sheath material 218 and the downstream regions of inner and outer anchors 201 via downstream sealing ring 204, which may extend along the periphery of the downstream ends of inner and outer anchors 201, 220, to thereby securely fasten sheath 203 to the downstream regions of inner and outer anchors 201, 220.

For example, upstream sealing ring 210 and downstream sealing ring 208 may be thermally bonded or solvent bonded to the upstream and downstream regions of inner and outer anchors 201, 220, sheath 203, and sheath material 218, e.g., via a reflow process. Alternatively, upstream sealing ring 210 and downstream sealing ring 208 may be compression molded onto or overmolded directly over the upstream and downstream regions of inner and outer anchors 201, 220. For example, upstream sealing ring 210 and downstream sealing ring 208 may be formed of a moldable thermoplastic material such as, thermoplastic urethane (TPU), thermoplastic elastomer (TPE), and/or thermoplastic vulcanizate (TPV). Accordingly, negative pressure chamber 212 may be defined by an outer surface of sheath 203, upstream sealing ring 210, downstream sealing ring 208, and the portion of outer anchor 220 between upstream sealing ring 210 and downstream sealing ring 208. Together, inner and outer anchors 201, 220 may be configured to provide an outward radial force against the walls of the intestine at the target site. Accordingly, inner and outer anchors 201, 220 function to secure bypass device 200 at the target site in conjunction with the negative pressure system, and to hold open the target area within the GI tract such that feces and other waste matter may pass through sheath 203 without contacting the walls surrounding the anastomosis site. As described above, under vacuum, intestinal tissue may be pulled into negative pressure chamber 212, thereby applying a radially inward force to outer anchor 220 and causing outer anchor 220 to transition from itself natural cylindrical configuration and conform to the pre-formed shape of inner anchor 201, as shown in FIG. 2C.

As described above, upstream sealing ring 210 and downstream scaling ring 208 may extend along the periphery of the upstream and downstream ends of inner and outer anchors 201, 220, respectively, thereby forming a soft, flexible upstream leading edge of inner and outer anchors 201, 220, and a soft, flexible downstream edge of inner and outer anchors 201, 220. Accordingly, upstream scaling ring 210 and downstream sealing ring 208 may prevent damage to the intestinal tissue adjacent to the upstream and downstream ends of inner and outer anchors 201, 220. In addition, upstream sealing ring 210 and downstream sealing ring 208 may provide longer sealing surfaces along upstream region 204 and downstream region 202, respectively, and flexibility to aid in retrieval of bypass device 200. Moreover, upstream sealing ring 210 and downstream sealing ring 208 may inhibit mucosal ingrowth on at least upstream region 204 and downstream region 202 of bypass device 200, e.g., the areas covered by the scaling rings.

Sheath 203 has an outer surface and an internal channel for allowing passage of feces and other waste matter therethrough. Sheath 203 has a length selected to extend from the target site in the GI tract through the patient's intestines and anus to a location external to the patient, as shown in FIG. 1. In some embodiments, the downstream end of sheath 203 may be coupled to a collection vessel (not shown) external to the patient's body for collecting feces and other waste matter therein. Sheath 203 may be formed of a biocompatible elastomer material such as, e.g., silicone or polyurethane.

As shown in FIG. 2B, one or more suction/fluid inlet tubes, e.g., suction tubes 214, 216 may extend along the outer surface of sheath 203 from out of the patient towards negative pressure chamber 212. The upstream regions of suction tubes 214, 216 may include a plurality of inlet ports 215, 217, respectively, sized and shaped to evacuate fluid therethrough, sufficient to create the vacuum within negative pressure chamber 212. For example, the upstream regions of suction tubes 214, 216 may be disposed across downstream sealing ring 208, such that one or more inlet ports 215 of suction tube 214 and one or more inlet ports 217 of suction tube 216 may be disposed within and in fluid communication with negative pressure chamber 212. Inlet ports 215, 217 may be distributed spatially evenly along the length of the upstream regions of suction tubes 214, 216. Alternatively, the spatial distribution of inlet ports 215, 217 may be selected to create a desired vacuum within negative pressure chamber 212. Preferably, the upstream regions of suction tubes 214, 216 may be equally spaced apart within negative pressure chamber 212 along the circumference of the outer surface of sheath 203 to thereby provide a symmetric application of vacuum within negative pressure chamber 212. Suction tubes 214, 216 may extend from within negative pressure chamber 212, through downstream sealing ring 208, and along the outer surface of sheath 203 and out the patient's anus, such that the downstream ends of suction tubes 214, 216 may be fluidicly coupled to the external pump of negative pressure system 300 for creating the vacuum within negative pressure chamber 212. In some embodiments, at least a portion of suction tubes 214, 216 may extend within the wall of sheath 203, e.g., within the membrane forming sheath 203.

As described in further detail below, inner and outer anchors 201, 220 may be used in conjunction with a negative pressure system, e.g., an external pump fluidicly coupled to the one or more suction/fluid inlet tubes, e.g., suction tubes 214, 216, to evacuate fluid from negative pressure chamber 212 via the one or more suction/fluid inlet tubes, to thereby create a vacuum within negative pressure chamber 212. Although FIGS. 2A to 2C illustrate two suction tubes, as will be understood by a person having ordinary skill in the art, system 100 may include more or less than two suction tubes for generating the desired vacuum within negative pressure chamber 212, and/or the suction tubes may not be equally spaced circumferentially along the outer perimeter of sheath 203.

Bypass device 200 may include one or more downstream retrieval loops 205 extending from a downstream end of inner and outer anchors 201, 220 for facilitating removal of bypass device 200, e.g., after the anastomosis has fully healed. For example, a retrieval device, e.g., an endoscopic grasper, may be introduced along the outer surface of sheath 203 toward downstream retrieval loop 205, to thereby engage with downstream retrieval loop 205, such that a force may be applied to the downstream portion of the retrieval device to pull on downstream retrieval loop 205 in the downstream direction, to thereby cause downstream retrieval loop 205 to contract radially inward and detach at least the downstream region of inner and outer anchors 201, 220, e.g., downstream sealing ring 208, from the intestinal tissue surrounding inner and outer anchors 201, 220, e.g., mucosal ingrowth that may have formed on inner and outer anchors 201, 220. The retrieval device may then be further retracted to apply a pulling force to downstream retrieval loop 205 in the downstream direction and remove bypass device 200 from the patient's body.

As shown in FIG. 2A, at least a portion of the outer surface of sheath 203 within negative pressure chamber 212 includes a plurality of microstructures, e.g., a micropattern of microstructures 224, disposed thereon. For example, the micropattern of microstructures 224 may comprise a micropattern of protrusions extending outwardly from the outer surface of sheath 203. Preferably, the micropattern of microstructures 224 is only disposed on the outer surface of sheath 203 that is disposed within negative pressure chamber 212. In addition, microstructures 224 preferably are integrally formed with the portion of sheath 203 within negative pressure chamber 212. Alternatively, microstructures 224 may be affixed to the portion of sheath 203 within negative pressure chamber 212 during manufacture. As shown in FIG. 2A, each microstructure of the micropattern of microstructures 224 may have a semi-spherical shape. For example, each microstructure of the micropattern of microstructures 224 may have a cross-sectional width of between 50 and 500 microns, e.g., about 300 microns, and a height of between 50 to 1000 microns, e.g., about 600 microns. In some embodiments, each microstructure of the micropattern of microstructures 224 may have a pitch of between 800-1200 microns, e.g., about 1000 microns. As will be understood by a person having ordinary skill in the art, the microstructures may have other shapes, e.g., columns, cubes, cones, pyramidal, circular pillars, rectangles, triangles, squares, sinusoids, etc.

The micropattern of microstructures 224 may include a plurality of rows and a plurality of columns of microstructures throughout negative pressure chamber 212. For example, the micropattern of microstructures 224 may extend radially around a full circumference of the outer surface of sheath 203 and longitudinally along an entire length of the outer surface of sheath 203 within negative pressure chamber 212. In some embodiments, the micropattern of microstructures 224 may be arranged in a triangular or rectangular shape on the outer surface of sheath 203 within negative pressure chamber 212. Moreover, the outer surface of sheath 203 further may include one or more ribs and/or one or more channels sized and shaped to guide fluid flow within negative pressure chamber 212, e.g., towards fluid inlet tubes 214, 216.

Upon actuation of the negative pressure system, a vacuum having a predetermined pressure may be created within negative pressure chamber 212 to thereby pull intestinal tissue toward inner and outer anchors 201, 220 and secure bypass device 200 at the target site. At least some intestinal tissue may be pulled through at least some openings 221 of outer anchor 220 and at least some openings 207 of inner anchor 201 at middle region 206, and further may contact the micropattern of microstructures 224. The micropattern of microstructures 224 is configured to inhibit the inner wall of the intestine from sealing against the outer surface of sheath 203 responsive to the vacuum to thereby encourage 360° fluidic communication within negative pressure chamber 212. Thus, the micropattern of microstructures 224 prevents the intestinal tissue from shutting off on the outer surface of sheath 203 and creating a sub-chamber of vacuum within negative pressure chamber 212. Accordingly, the micropattern of microstructures 224 maintains a vacuum throughout negative pressure chamber 212 such that bypass device 200 remains anchored at the target location when negative pressure is applied in negative pressure chamber 212. As will be understood by a person having ordinary skill in the art, the micropattern of microstructures may be incorporated with any of the bypass devices described herein, e.g., bypass devices 1000, 1100, 1200, 1300, 1400, 1500, 1700, to thereby encourage 360° fluidic communication within the respective negative pressure chamber such that a vacuum is maintained throughout the negative pressure chamber and the respective anchor remains anchored at the target location when negative pressure is applied in the negative pressure chamber. By implementing a micropattern of microstructures on the outer surface of a sheath within the negative pressure chamber to encourage 360° fluidic communication within the negative pressure chamber, as well as double anchor having a recessed middle region, e.g., dog bone shape resembling an hourglass, under vacuum to improve mechanical anchoring, and automated pump parameters adjustment to improve vacuum maintenance, the overall length of the stent/scaffold of inner and outer anchors 201, 220 may be reduced, e.g., 80-90 mm, or 70 mm.

Figure 3A:
FIGS. 3A and 3B illustrates an exemplary pump device of the negative pressure bypass system constructed in accordance with the principles of the present disclosure.
Figure 3B:
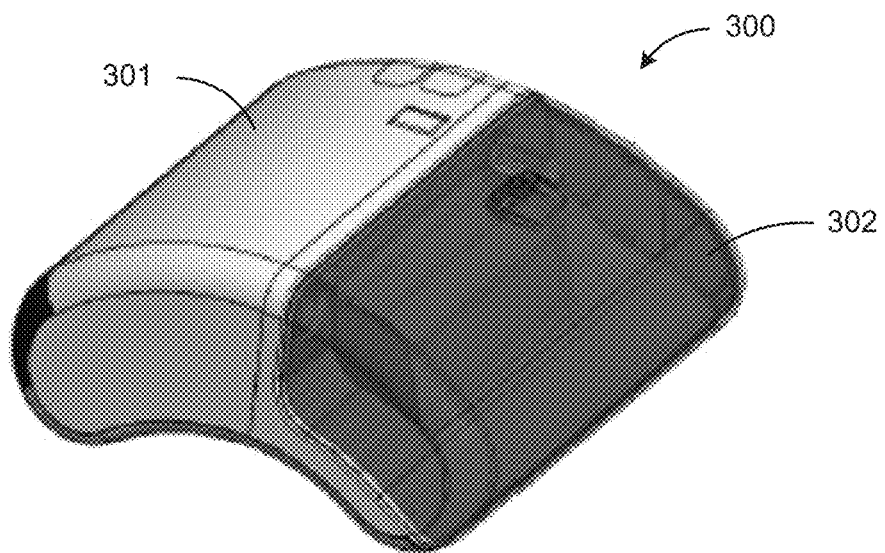

Referring now to FIGS. 3A and 3B, an exemplary negative pressure system for generating the vacuum within negative pressure chamber 212 of bypass device 200, and monitoring the pressure therein is provided. System 300 may include an external pump, for example, disposed within housing 301 and fluidicly coupled to negative pressure chamber 212 via, e.g., suction tubes 214, 216. For example, the external pump may be fluidicly coupled to the downstream ends of suction/fluid inlet tubes 214, 216. Accordingly, the pump may be actuated to evacuate fluid from negative pressure chamber 212 via suction tubes 214, 216, to thereby create the vacuum within negative pressure chamber 212. As shown in FIGS. 3A and 3B, housing 301 may have handle 303 sized and shaped to facilitate carrying and handling of system 300 by a user. Housing 301 may be sized and shaped to be worn by the patient, e.g., via a satchel or a belt wearable by the patient. Additionally, or alternatively, housing 301 may be sized and shaped to be mounted, e.g., bedside, on an IV pole, etc. Moreover, system 300 further may include detachable fluid reservoir chamber 302 configured to be removably coupled to housing 301 to facilitate removal of waste matter from fluid reservoir chamber 302 and/or cleaning of fluid reservoir chamber 302. Accordingly, fluid reservoir chamber 302 may be fluidicly coupled to the negative pressure chamber of the respective anchor via the fluid inlet tubes coupled thereto, and sized and shaped to collect waste matter within fluid evacuated from the negative pressure chamber when negative pressure is applied.

As shown in FIG. 3B, fluid reservoir chamber 302 may be made of a transparent material to facilitate manual inspection of the contents within fluid reservoir chamber 302 by a user, to thereby inform a user of when fluid reservoir chamber 302 needs to be emptied, cleaned, and/or replaced. System 300 may include one or more sensors fluidicly coupled to fluid reservoir chamber 302, such that a controller of system 300, e.g., controller 400 described in further detail below with regard to FIG. 4, may generate an alert to inform a user when the waste matter within fluid reservoir chamber 302 exceeds a predetermined threshold. For example, the alert may be an audible or visual alert emitted/displayed on a user interface on housing 301, e.g., a graphical user interface. Additionally, or alternatively, the alert may be emitted/displayed via a remote computer operatively coupled to system 300. The user interface of system 300 may include one or more actuators, e.g., buttons, switches, etc., configured for actuation by a user to turn on/off and/or adjust/control one or more operating parameters of system 300. The user interface may display information associated with system 300, e.g., pressure measurements within negative pressure chamber 212.

Figure 3C:
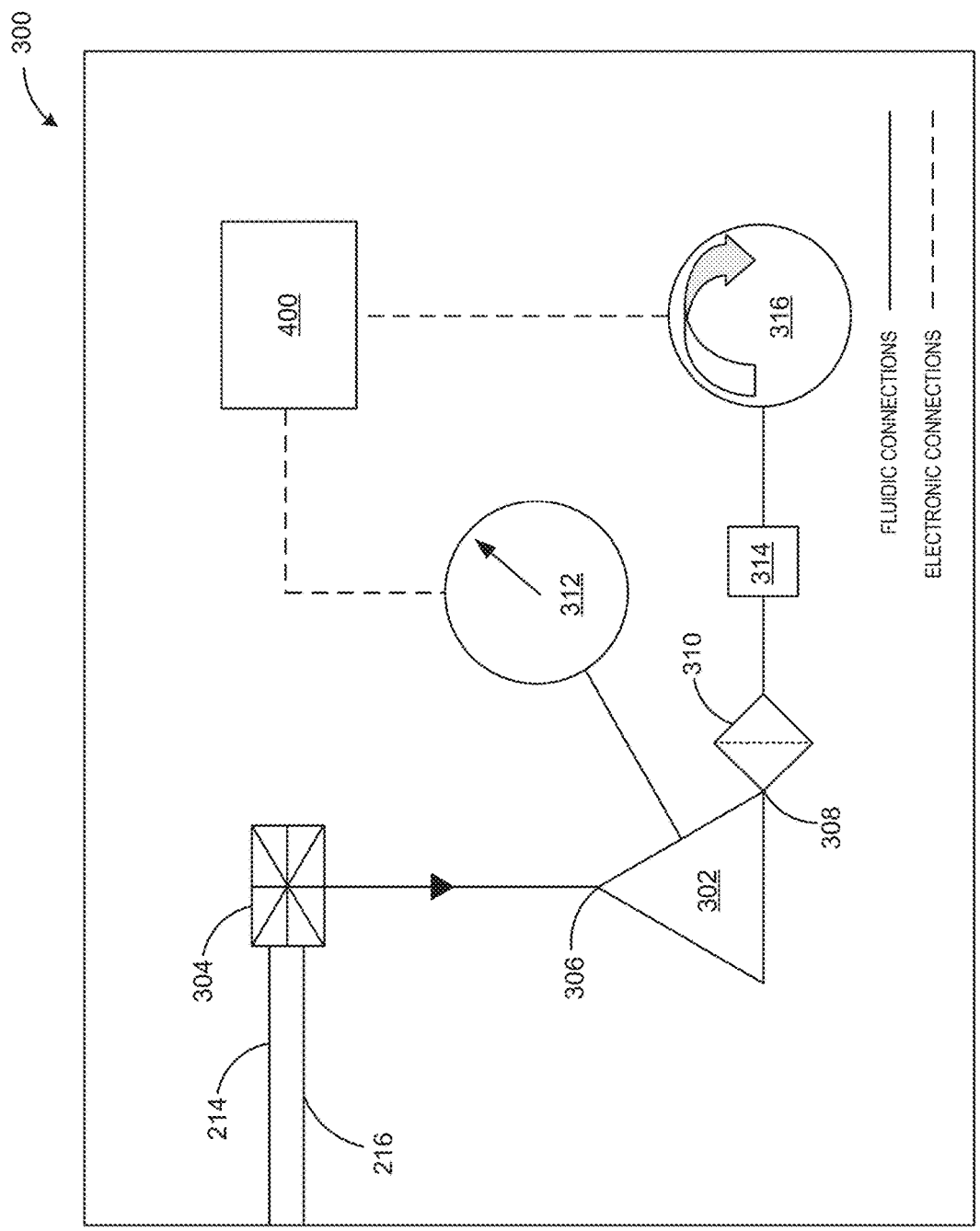
FIG. 3C is a schematic illustrating various components of the pump device in accordance with the principles of the present disclosure.

FIG. 3C is a schematic illustrating the internal components of an exemplary negative pressure system for generating the vacuum within the negative pressure chamber. System 300 may be used with any of the bypass devices described herein, e.g., bypass devices 200, 1000, 1100, 1200, 1300, 1400, 1500, 1700. As described above, fluid reservoir chamber 302 may be sized and shaped for collecting fluid and waste matter within the fluid evacuated from the negative pressure chamber of the anchor, e.g., via suction tubes 214, 216, and may be fluidicly coupled to pump 316. For example, fluid evacuated from negative pressure chamber 212 may travel through suction tubes 214, 216, and enter fluid reservoir chamber 302 via inlet 306. As shown FIG. 3C, system 300 may include a controller, e.g., controller 400, in electrical communication with the electrical components of system 300, e.g., pump 316 and pressure transducers 312, described in further detail below.

As shown in FIG. 3C, system 300 may include vacuum/pressure transducer 312 fluidly coupled to negative pressure chamber 212 via fluid reservoir chamber 302 and the suction/fluid inlet tubes coupled thereto, e.g., suction tubes 214, 216. Pressure transducer 312 may be configured to measure pressure within fluid reservoir chamber 302, which is indicative of the pressure within negative pressure chamber 212, and generate one or more signals indicative of the measured pressure for transmission to controller 400. Controller 400 may be operatively coupled to pump 316, to thereby cause pump 316 to generate a vacuum having a predetermined pressure within negative pressure chamber 212 via suction tubes 214, 216. In some embodiments, each suction tube may be fluidically coupled to a dedicated pressure transducer for measuring pressure within the respective fluid inlet tube. Moreover, suction tubes 214, 216 may be fluidically coupled together via coupler 304, such that a single fluid inlet line in fluid communication with both suction tubes 214, 216 is fluidically coupled to fluid reservoir chamber 302 via inlet 306 of fluid reservoir chamber 302. In addition, system 300 may include filter 310 disposed between fluid reservoir chamber 302 and pump 316 to prevent waste matter from entering pump 316. For example, waste matter within the fluid evacuated from negative pressure chamber 212 and other fluids may be collected within fluid reservoir chamber 302, such that the remaining fluid, e.g., gas, may exit fluid reservoir chamber 302 via outlet 308 and travel across filter 310 and exit system 300 via pump 316.

System 300 further may include one or more check valves 314 fluidically coupled to suction tubes 214, 216, e.g., between filter 310 and pump 316, configured to allow pump 316 to return to ambient pressure, e.g., atmospheric pressure, without impacting pressure of system 300. For example, prior to turning on pump 316, check valve 314 may be actuated to an open state until the pressure within pump 316 reaches atmospheric pressure. Check valve 314 may then be may be actuated to a closed state during operation of pump 316, such that pump 316 may generate a vacuum having a predetermined pressure within negative pressure chamber 212. In some embodiments, instead of check valve 314, system 300 may include a small controlled leak configured to allow pump 316 to reach atmospheric pressure, e.g., when system 300 is in steady state conditions. In some embodiments, system 300 may include one or more sensors fluidicly coupled to fluid reservoir chamber 302 and configured to measure an amount of waste matter within fluid reservoir chamber 302. The one or more additional sensors may generate one or more signals indicative of the level of waste matter within fluid reservoir chamber 302 for transmission to controller 400.

Figure 4:
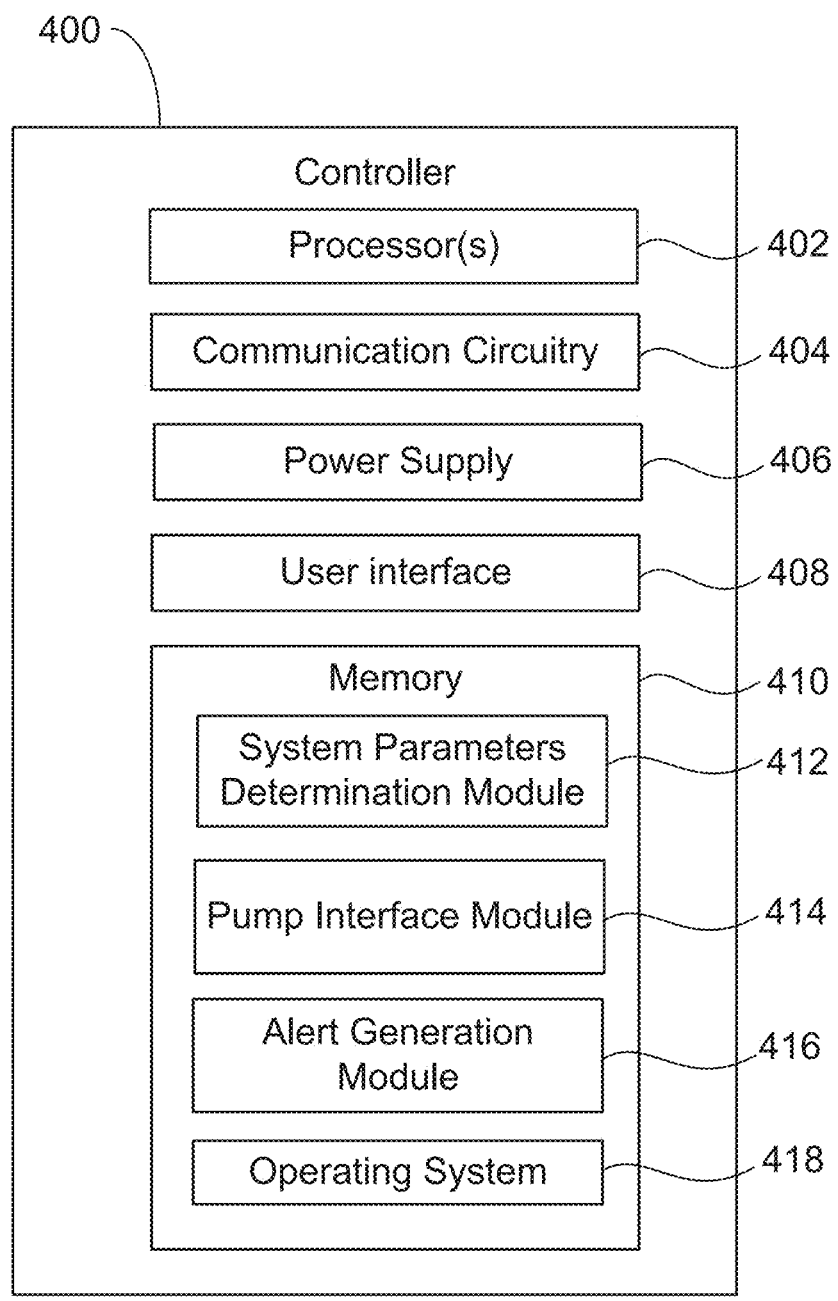
FIG. 4 illustrates exemplary components of a controller of the pump device in accordance with the principles of the present disclosure.

Referring now to FIG. 4, components that may be included in controller 400 for controlling the negative pressure systems described herein are provided. Controller 400 may include one or more processors 402, communication circuitry 404, power supply 406, user interface 408, and/or memory 410. One or more electrical components and/or circuits may perform some of or all the roles of the various components described herein. Although described separately, it is to be appreciated that electrical components need not be separate structural elements. For example, controller 400 and communication circuitry 404 may be embodied in a single chip. In addition, while controller 400 is described as having memory 410, a memory chip(s) may be separately provided.

Controller 400 may contain memory and/or be coupled, via one or more buses, to read information from, or write information to, memory. Memory 410 may include processor cache, including a multi-level hierarchical cache in which different levels have different capacities and access speeds. The memory also may include random access memory (RAM), other volatile storage devices, or non-volatile storage devices. Memory 410 may be RAM, ROM, Flash, other volatile storage devices or non-volatile storage devices, or other known memory, or some combination thereof, and preferably includes storage in which data may be selectively saved. For example, the storage devices can include, for example, hard drives, optical discs, flash memory, and Zip drives. Programmable instructions may be stored on memory 410 to execute algorithms for, e.g., determining whether the pressure measured within negative pressure chamber 212 falls outside of a predetermined range and adjusting one or more parameters of pump 316 to maintain the pressure within negative pressure chamber 212 within the predetermined range.

Controller 400 may incorporate processor 402, which may consist of one or more processors and may be a general purpose processor, a digital signal processor (DSP), an application specific integrated circuit (ASIC), a field programmable gate array (FPGA) or other programmable logic device such as a programmable logic controller (PLC), discrete gate or transistor logic, discrete hardware components, or any suitable combination thereof designed to perform the functions described herein. Controller 400 also may be implemented as a combination of computing devices, e.g., a combination of a DSP and a microprocessor, a plurality of microprocessors, one or more microprocessors in conjunction with a DSP core, or any other such configuration. Controller 400, in conjunction with firmware/software stored in memory 410 may execute an operating system (e.g., operating system 418), such as, for example, Windows, Mac OS, QNX, Unix or Solaris 5.10. Controller 400 also executes software applications stored in the memory. For example, the software may be programs in any suitable programming language known to those skilled in the art, including, for example, C++, PHP, or Java.

Communication circuitry 404 may include circuitry that allows controller 400 to communicate with pump 316 and pressure transducer 312, and optionally, one or more additional sensors associated with system 100, as described in further detail below. Communication circuitry 404 may be configured for wired and/or wireless communication over a network such as the Internet, a telephone network, a Bluetooth network, and/or a WiFi network using techniques known in the art. Communication circuitry 404 may be a communication chip known in the art such as a Bluetooth chip and/or a WiFi chip. Communication circuitry 404 permits controller 400 to transfer information, such as pressure measurements within negative pressure chamber 212 locally and/or to a remote location such as a server.

Power supply 406 may supply alternating current or direct current. Power supply 406 may be a port to allow controller 400 to be plugged into a conventional wall socket, e.g., via a cord with an AC to DC power converter and/or a USB port, for powering components within controller 400. In direct current embodiments, power supply 406 may include a suitable battery such as a replaceable battery or rechargeable battery and may include circuitry for charging the rechargeable battery.

User interface 408 may be used to receive inputs from, and/or provide outputs to, a user. For example, user interface 408 may include a touchscreen display, switches, dials, lights, etc. Accordingly, user interface 408 may display information such as pressure measurements of negative pressure chamber 212 and/or visual alerts, e.g., when the pressure within negative pressure chamber 212 falls outside the predetermined range. In some embodiments, user interface 408 may receive user input including adjustments to one or more operating parameters of pump 316. In some embodiments, user interface 408 is not present on controller 400, but is instead provided on a remote, external computing device communicatively connected to controller 400 via communication circuitry 404.

Memory 410, which is one example of a non-transitory computer-readable medium, may be used to store operating system (OS) 418, system parameters determination module 412, pump interface module 414, and alert generation module 416. The modules are provided in the form of computer-executable instructions/algorithms that may be executed by processor 402 for performing various operations in accordance with the disclosure.

System parameters determination module 412 may be executed by processor 402 for receiving one or more signals from pressure transducer 312, indicative of pressure within negative pressure chamber 212 in real time. Moreover, system parameters determination module 412 may be configured to process and analyze the pressure measurement signals to determine whether the pressure within negative pressure chamber 212 falls outside of a predetermined range stored in memory 410. System parameters determination module 412 further may be configured to determine the volume of system 300 in real time, e.g., based on the measured pressure of system 300, as will be understood by a person having ordinary skill in the art. Accordingly, based on the measured volume of system 300 and the known target volume of system 300 stored in memory 410, as well as the known pump flow rate of pump 312, the expected pump run time, e.g., the amount of time required by pump 316 to achieve the known target volume of system 300 under normal conditions, may be calculated by system parameters determination module 412. Additionally or alternatively, the expected pump run time may be predetermined and stored in memory 410.

Further, the actual pump run time, e.g., the amount of time actually required by pump 316 to achieve the known target volume of system 300, may be recorded. Accordingly, system parameters determination module 412 may detect the presence of an occlusion within system 100 if the actual pump run time deviates from the expected pump run time, e.g., by more than a predetermined threshold. For example, for a negative pressure system having a total system volume of 500 mL and a pump flow rate of 10,000 mL/min, the expected pump run time for an operating vacuum range from 0 to −50 kPa may approximately be 6.5 seconds, and the expected pump run time for an operating vacuum range from −30 to −50 kPa may approximately be 1.5 seconds, such that system parameters determination module 412 may determine that there is an occlusion within the system if the pump run time is less than 1 second. For example, the total system volume may be 250 to 2000 mL, the pump flow rate may be 1,000 to 50,000 mL/min, the operating vacuum range may be from 0 to −80 kPa, and an occlusion may be detected if the actual pump run time deviates from the expected pump run time by, e.g., 0.25 to 10 seconds.

As described above, system 300 may include one or more additional sensors configured to generate one or more signals indicative of an amount of waste matter within fluid reservoir chamber 302. Accordingly, system parameters determination module 412 may be configured to receive the one or more signals indicative of the amount of waste matter within fluid reservoir chamber 302, and process and analyze the one or more signals to determine whether the amount of waste matter within fluid reservoir chamber 302 exceeds a predetermined threshold. In some embodiments, as described in further detail below, system 100 may include one or more additional sensors configured to measure, e.g., data indicative of a presence of at least one of blood, feces, or predefined gases between the bypass device and intestinal tissue surrounding bypass device 200, and/or data indicative of a position of bypass device 200 relative to the intestinal anastomosis. Accordingly, system parameters determination module 412 may be configured to process and analyze the data measured by the one or more additional sensors to determine whether the measured data falls outside one or more respective predetermined ranges.

Pump interface module 414 may be executed by processor 402 for controlling operation of pump 316. For example, upon actuation of pump 316, e.g., via user interface 408, pump interface module 414 may instruct pump 316 to turn on. Moreover, when system parameters determination module 412 determines that the pressure within negative pressure chamber 212 falls outside of the predetermined range, pump interface module 414 may automatically adjust one or more operating parameters of pump 316, and instruct pump 316 to operate in accordance with the adjusted parameters, to thereby maintain the pressure within negative pressure chamber 212 within the predetermine range. Preferably, pump interface module 414 may be configured to instruct pump 316 to turn off when the pressure within negative pressure chamber 212, as measured by pressure transducer 312, falls within the predetermined range. Thus, system 100 may include one or more valves fluidicly coupled to suction tubes 214, 216 configured to prevent fluid ingress towards negative pressure chamber 212, to thereby maintain the pressure within negative pressure chamber 212. Accordingly, pump interface module 414 may instruct pump 316 to turn back on when the pressure within negative pressure chamber 212 falls outside of the predetermined range.

In some embodiments, pump interface module 414 may be configured to adjust one or more parameters of pump 316 over time. For example, as intestinal tissue/mucosal ingrowth forms on inner and outer anchors 201, 220 over time, a smaller vacuum may be required to secure bypass device 200 at the target site upstream of the anastomosis site. Accordingly, pump interface module 414 may reduce the operations of pump 316 to generate a smaller vacuum within negative pressure chamber 212 over time. Alternatively, in some embodiments, pump interface module 414 may be configured to instruct pump 316 to operate continuously, e.g., continuously evacuating fluid from negative pressure chamber 212 to continuously create a vacuum having a pressure within the predetermined range.

Alert generation module 416 may be executed by processor 402 for generating an alert when system parameters determination module 412 determines that the pressure within negative pressure chamber 212 falls outside of the predetermined range. For example, the alert may be an audible alert and/or a visual alert, which may be displayed via user interface 408. Additionally, or alternatively, alert generation module 416 may be configured to periodically generate an alert to facilitate routine manual inspection of system 300 by a user. For example, alert generation module 416 may be configured to generate an alert once or multiple times a day to remind a user to manually monitor the operations of system 300. In addition, alert generation module 416 may be configured to generate an alert indicative of when the presence of a occlusion of system 100, e.g., a clog in one or more of suction tubes 214, 216, is detected, e.g., when system parameters determination module 412 determines that the actual pump run time deviates from the expected pump run time by more than a predetermined threshold, as described above.

Moreover, alert generation module 416 may be configured to generate an alert when the amount of waste matter within fluid reservoir chamber 302 measured exceeds the predetermined threshold, to thereby inform a user to empty or replace fluid reservoir chamber 302. As described above, system 100 may measure, e.g., data indicative of a presence of at least one of blood, feces, or predefined gases between the bypass device and intestinal tissue surrounding bypass device 200, and/or data indicative of a position of bypass device 200 relative to the intestinal anastomosis. Accordingly, alert generation module 416 may be configured to generate an alert indicative of when presence of at least one of blood, feces, or predefined gases between the bypass device and intestinal tissue surrounding bypass device 200 exceeds a predetermined threshold, and/or when the position of bypass device 200 relative to the intestinal anastomosis exceeds a predetermined threshold, such that corrective action may be taken.

Figure 5:
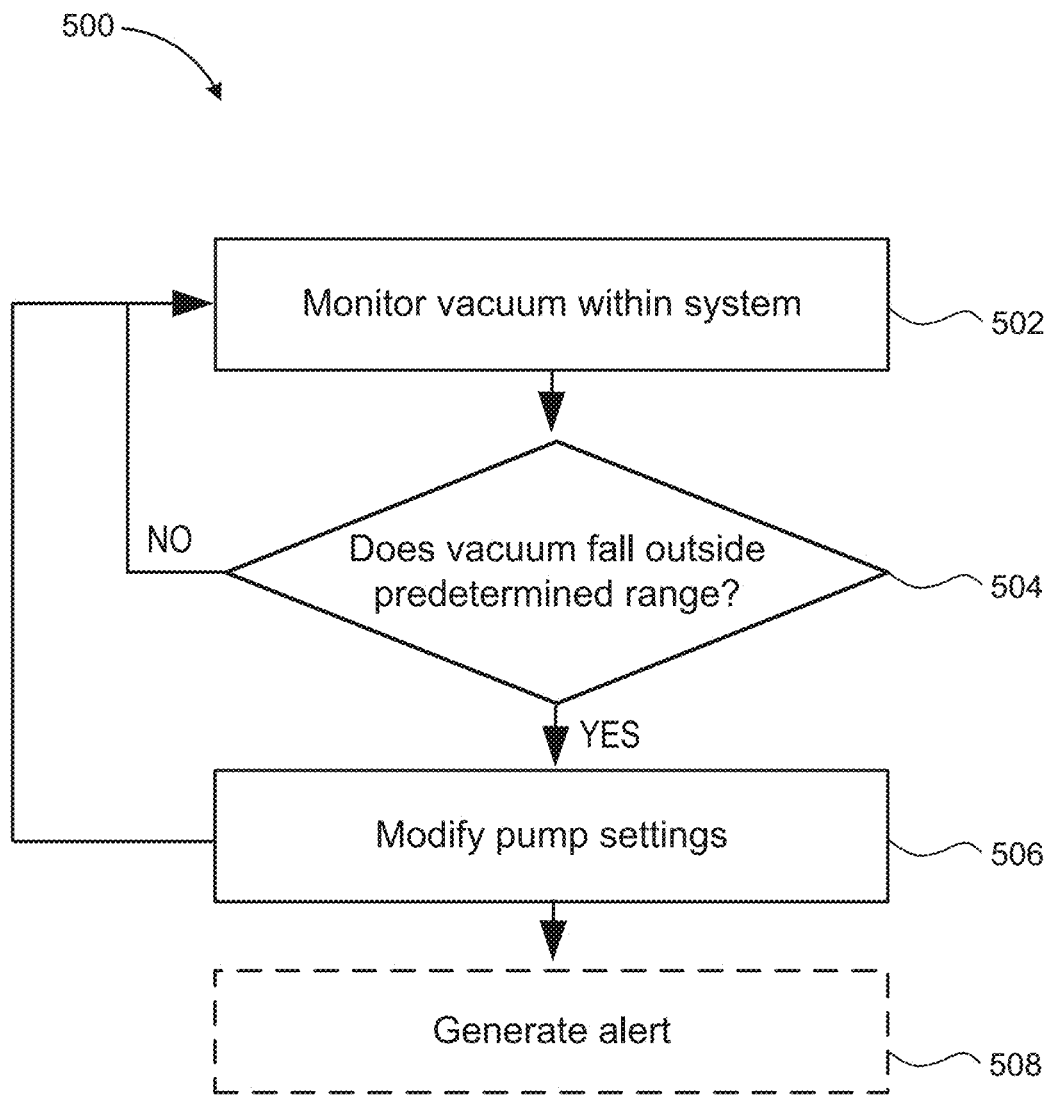
FIG. 5 is a flow chart illustrating exemplary method steps for monitoring and controlling pressure of the negative pressure bypass system.

Referring now to FIG. 5, exemplary method steps for automated monitoring of bypass device 200 is provided. At step 502, controller 400 may monitor the vacuum within system 100, e.g., the pressure within negative pressure chamber 212. For example, system parameters determination module 412 may process and analyze the pressure measurement signals received from pressure transducer 312, indicative of pressure within negative pressure chamber 212. At step 504, controller 400 may determine whether the pressure within negative pressure chamber 212, as indicated by the pressure measurements by pressure transducer 312, falls outside of a predetermined range. If the pressure within negative pressure chamber 212 is determined not to fall outside the predetermined range at step 504, method 500 may return to step 502. If the pressure within negative pressure chamber 212 is determined to fall outside the predetermined range at step 504, method 500 may proceed to step 506.

At step 506, controller 400 may automatically modify pump settings of pump 316, e.g., one or more operational parameters of pump 316, to maintain the pressure within negative pressure chamber 212 within the predetermined range. For example, controller 400 may instruct pump 316 to turn on if pump 316 is currently in an off state, controller 400 may instruct pump 316 to turn off if pump 316 is currently in an on state, and/or controller 400 may instruct pump 316 to evacuate fluid within negative pressure chamber 212 at a higher rate/force to thereby increase the pressure within negative pressure chamber 212 or at a lower rate/force to thereby decrease the pressure within negative pressure chamber 212. Accordingly, method 500 may return to step 502 to continuously monitor the vacuum of system 300. Optionally, at step 508, controller 400 may generate an alert to inform a user when the pressure within negative pressure chamber 212 is detected to fall outside of the predetermined range. Additionally, or alternatively, as described above, controller 400 may periodically generate an alert to remind a user to manually monitor operations of system 300.

Figure 6B:
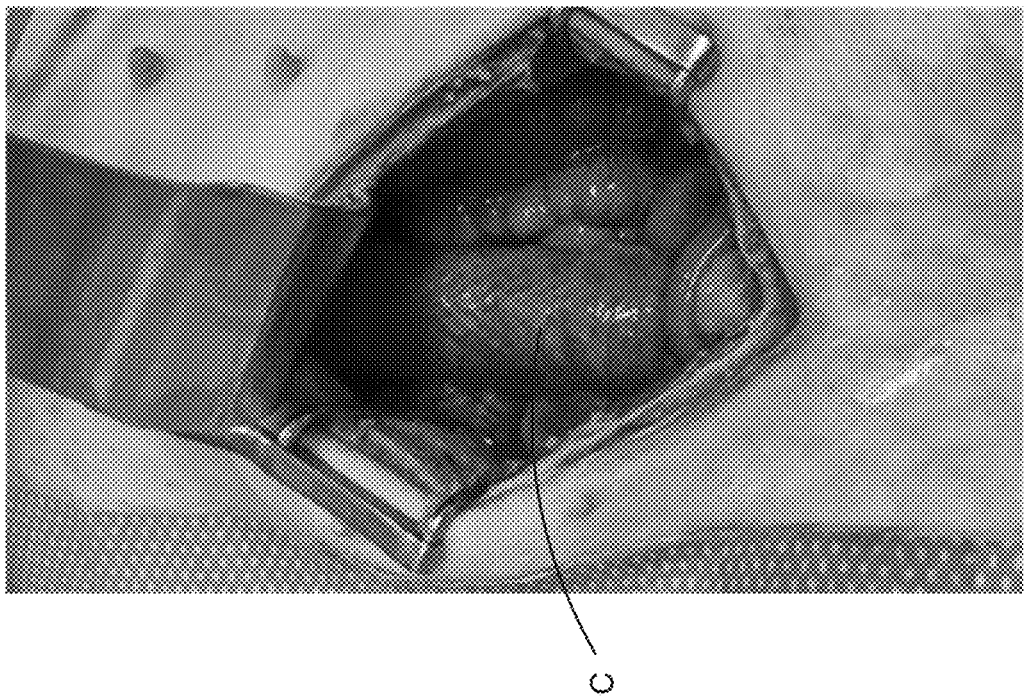
FIG. 6B illustrates the colon under vacuum generated via the single braided anchor.
Figure 6A:
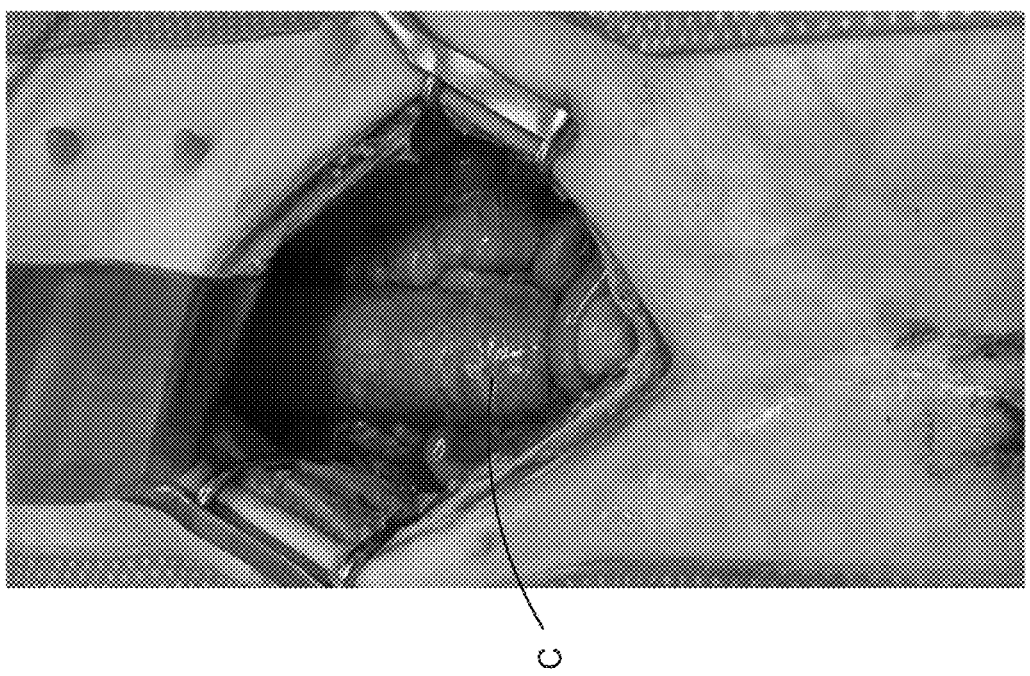
FIG. 6A illustrates a colon having a single braided anchor disposed therein.
Figure 6D:
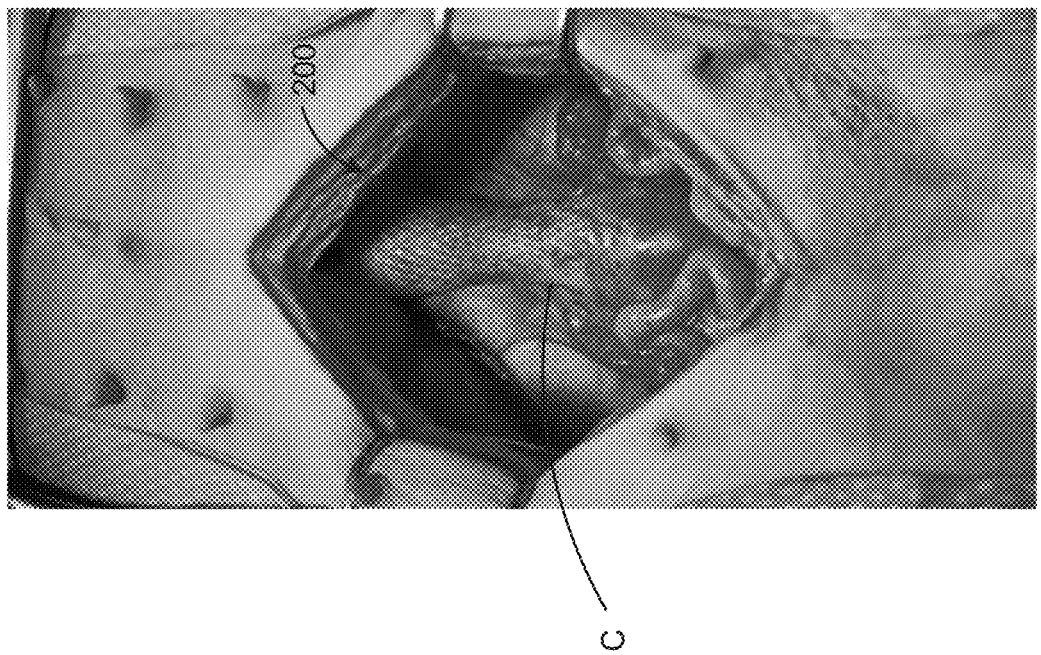
FIG. 6D illustrates the colon under vacuum generated via the double braided anchor.
Figure 6C:
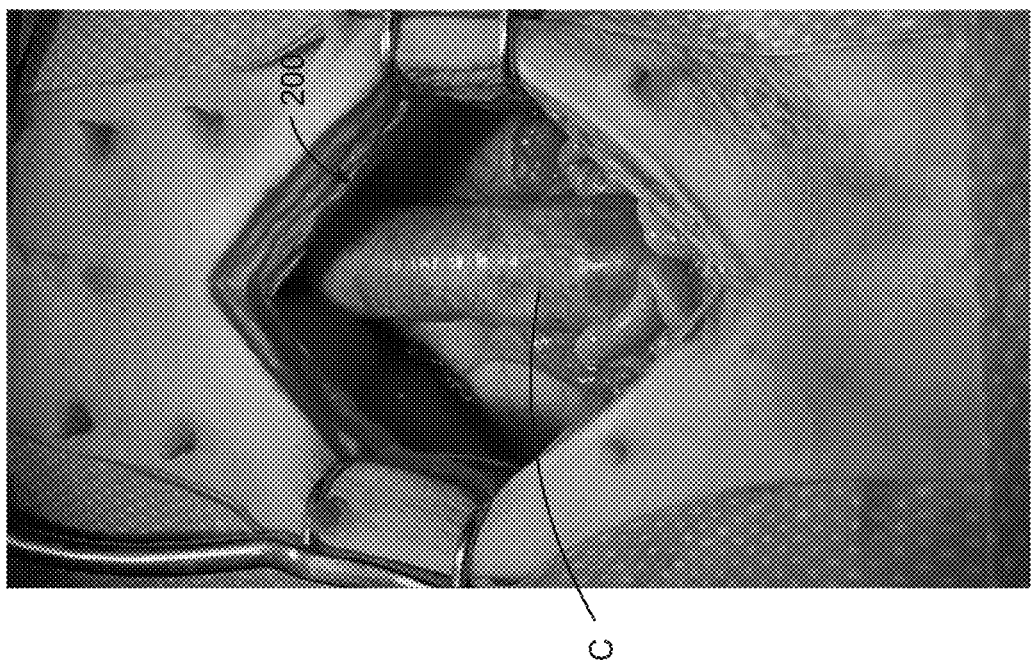
FIG. 6C illustrates a colon having a double braided anchor disposed therein.

FIG. 6A illustrates colon C with a bypass device having a single braided anchor disposed within the lumen of the colon, and FIG. 6B illustrates colon C under vacuum generated via the single braided anchor bypass device. FIG. 6C illustrates colon C with a bypass device having a double braided anchor, e.g., bypass device 200 having inner and outer anchors 201, 220, disposed within the lumen of the colon, and FIG. 6D illustrates colon C under vacuum generated via bypass device 200. From a comparison of FIGS. 6B and 6D, bypass device 200 is shown to generate a stronger and more consistent vacuum within the system, e.g., as evidenced by colon C being more tightly wrapped around the double braided anchor bypass system in FIG. 6D than the single braided anchor bypass system in FIG. 6B.

Figure 7A:
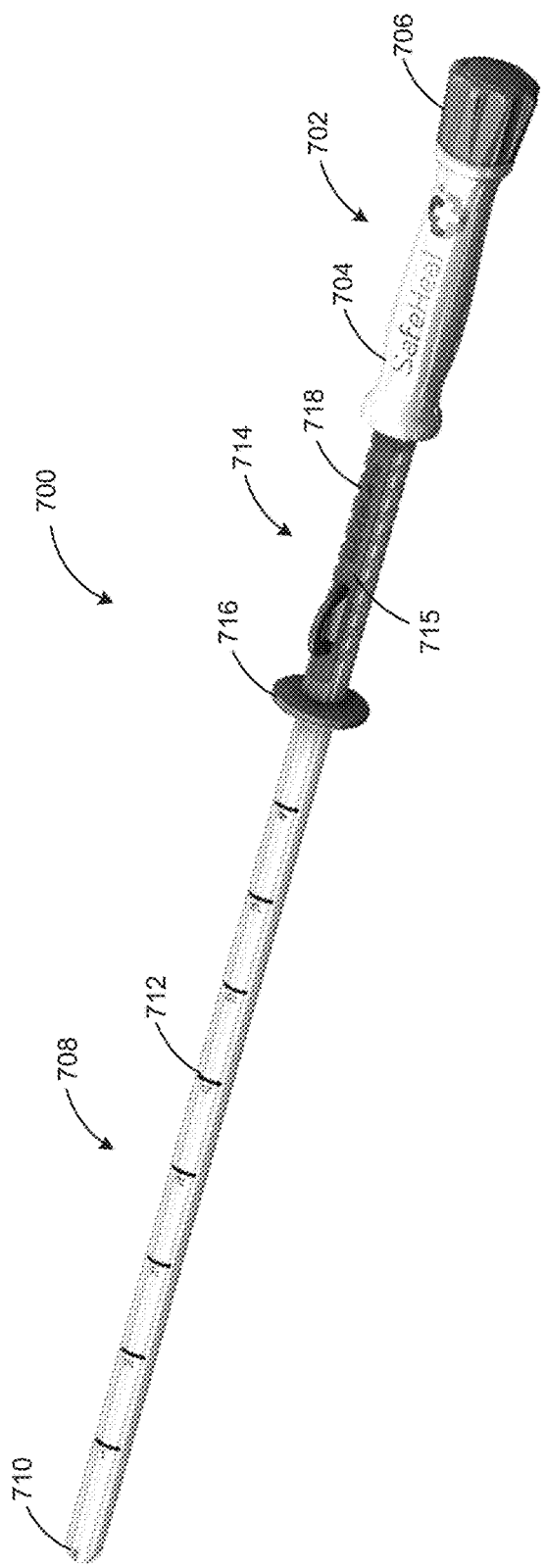
FIGS. 7A to 7G illustrate an exemplary introducer device for delivering the negative pressure bypass system, constructed in accordance with the principles of the present disclosure.
Figure 7B:
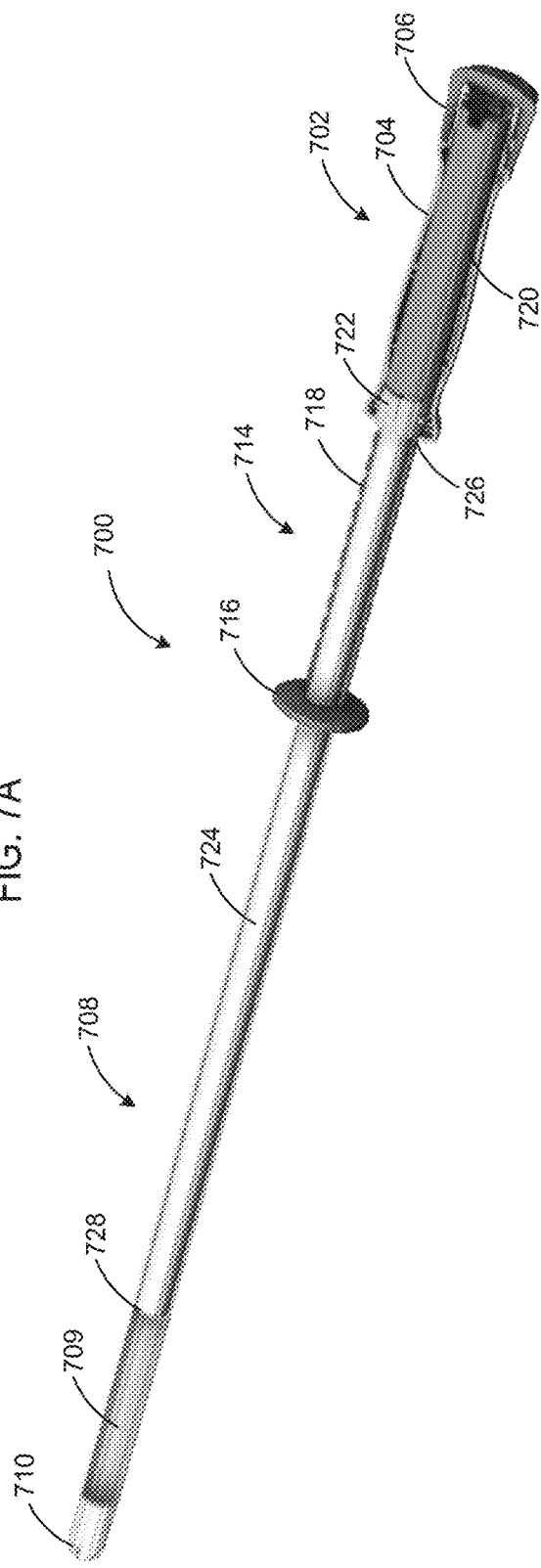

Referring now to FIGS. 7A to 7G, an exemplary introducer device for delivering bypass device 200 to the target site within the patient's GI tract is provided. Introducer 700 may include a guide tube having first tubular portion 708 configured for insertion within the patient's GI tract, and second tubular portion 714 coupled to a downstream end of first tubular portion 708. Additionally, introducer 700 may include handle portion 702 operatively coupled to second tubular portion 714 and configured to be actuated to actuate introducer 700. As shown in FIGS. 7A and 7B, an upstream end of second tubular portion 714 may be fixedly coupled to the downstream end of first tubular portion 708, e.g., via stop 716. Stop 716 may have a disc-shaped profile, having a diameter larger than the diameter of first tubular portion 708. For example, stop 716 may be sized and shaped to prevent further insertion of introducer 700 through a patient's anus into the GI tract, by contacting the patient's anus.

First tubular portion 708 may have a length selected such that upstream tip 710 of first tubular portion 708 may be disposed at the target site within the patient's GI tract upstream of an anastomosis site, while stop 716, second tubular portion 714, and handle portion 702 remain external to the patient's body. Accordingly, first tubular portion 708 may be formed of a flexible material to facilitate maneuvering of first tubular portion 708 through the patient's GI tract. As shown in FIG. 7A, the outer surface of first tubular portion 708 may include markings 712 for visually indicating a depth first tubular portion 708 has been inserted within a patient's GI tract through the anus. Moreover, as shown in FIG. 7B, first tubular portion 708 may have lumen 709 extending therethrough, and sized and shaped to receive bypass device 200 therein in its collapsed delivery state.

Upstream tip 710 may be constructed as described in U.S. Pat. No. 11,589,869 to Khosrovaninejad, the entire contents of which are incorporated herein by reference. For example, upstream tip 710 may be configured to transition between a closed configuration and an open configuration to expose lumen 709 and permit delivery of bypass device 200 therethrough. In addition, upstream tip 710 may have a tulip configuration formed of a plurality of elastically deformable cut-out tabs that are biased towards the closed configuration where the plurality of tabs form a sealed closure to isolate lumen 709 from the environment surrounding introducer 700, e.g., the GI tract. The plurality of tabs may overlap with each other to form the sealed closure, and may have a stiffness in the closed configuration sufficient to be inserted through a patient's anus and into the GI tract. Moreover, the plurality of tabs may be transitioned to the open configuration upon application of a force against the plurality of tabs, e.g., from within lumen 709. For example, as described in further detail below, as first tubular portion 708 is retracted in a downstream direction relative to bypass device 200 within lumen 709, bypass device 200 may apply a force against the plurality of tabs of upstream tip 710 to thereby transition upstream tip 710 to its open configuration to permit bypass device 100 to pass therethrough into the GI tract at the target site.

Figure 7C:
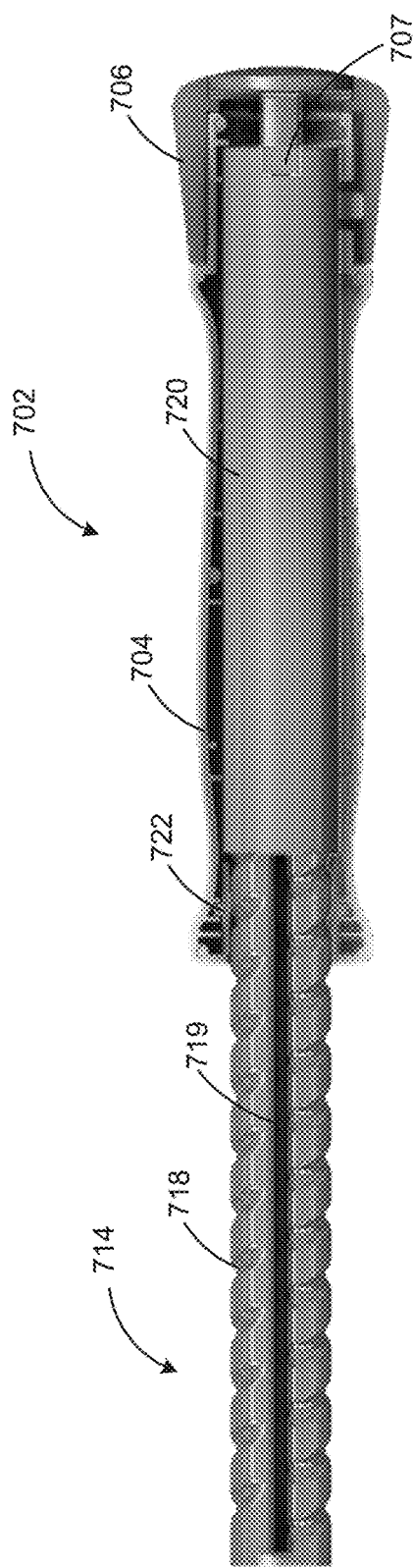

As shown in FIGS. 7A and 7B, handle portion 702 may include handle housing 704 sized and shaped to be held by a user as introducer 700 is inserted within a patient's GI tract. Handle housing 704 may be operatively coupled to actuator 706, e.g., a rotatable knob, configured to be rotated relative to handle housing 704 to actuate second tubular portion 714, as described in further detail below. For example, as shown in FIGS. 7C and 7D, knob 706 may be fixedly coupled to inner tube 720 disposed within handle housing 704 via connection 707, such that rotation of knob 706 causes rotation of inner tube 720 relative to handle housing 704, while axial movement of inner tube 720 relative to handle housing 704 is prevented.

Figure 7D:
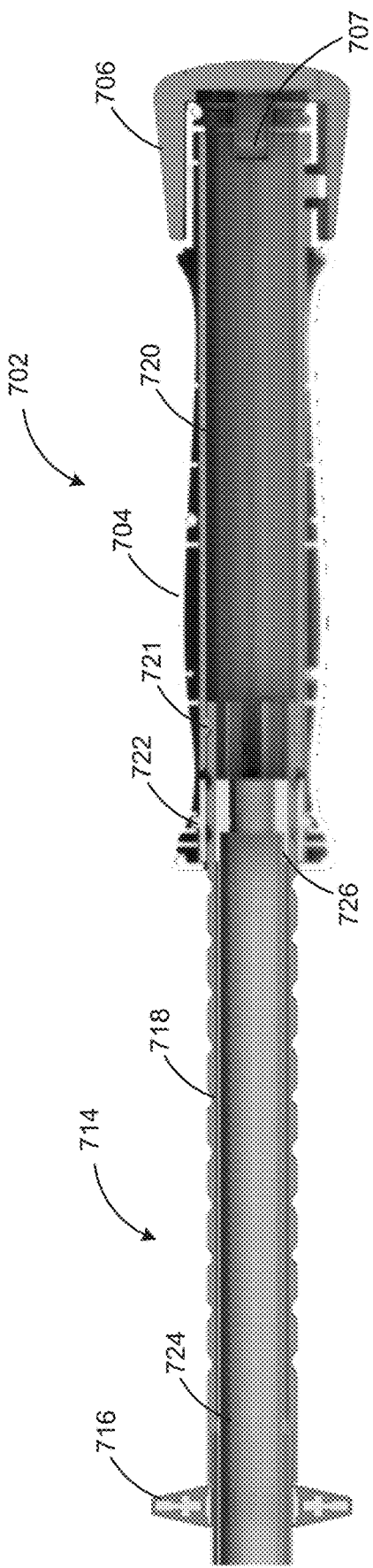

As shown in FIG. 7D, a downstream end of second tubular portion 714 may be disposed within a lumen of inner tube 720. Moreover, an upstream end of inner tube 720 may include one or more features 721 extending radially inwardly, and sized and shaped to slidably engage with one or more grooves 718 extending along an outer surface of second tubular portion 714. For example, one or more grooves 718 may form a threaded surface of second tubular portion 714, such that as inner tube 720, which is fixed axially relative to handle housing 704, rotates via rotation of knob 706, the slidable engagement between one or more features 721 and one or more grooves 718 causes one or more grooves 718 to slide along one or more grooves 718, thereby moving second tubular portion 714, and accordingly first tubular portion 708 fixed thereto, axially relative to inner tube 720 and handle housing 704. Accordingly, one or more grooves 718 may extend in a circumferential and axial pattern along the outer surface of second tubular portion 714, e.g., in a helical pattern. Moreover, as shown in FIG. 7C, second tubular portion 714 may have linear track 719 extending longitudinally along the outer surface of second tubular portion 714, and sized and shaped to slidably engage with a rail (not shown) of handle housing 704, to thereby prevent rotation of second tubular portion 714 relative to handle housing 704 as the engagement between one or more features 721 and one or more grooves 718 causes axial translation of second tubular portion 714 relative to handle housing 704 during rotation of knob 706. Specifically, the engagement between the rail of handle housing 704 and linear track 719 in conjunction with the engagement between one or more features 721 and one or more grooves 718 as inner tube 720 is rotated causes axial translation of second tubular portion 714 relative to handle housing 704.

As shown in FIGS. 7B and 7D, introducer 700 further may include pusher 724 fixedly coupled to handle housing 704, and extending through a lumen of second tubular portion 714 and at least a portion of lumen 709 of first tubular portion 708, such that upstream end 728 of pusher 724 is disposed within an upstream region of lumen 709 of first tubular portion 708, e.g., downstream of bypass device 200 in its collapsed delivery state within lumen 709. For example, as shown in FIG. 7D, downstream end 726 of pusher 724 may be fixedly coupled to holder 722 disposed within handle housing 704. For example, holder 722 may include an inner portion disposed within the lumen of second tubular portion 714, such that the inner portion is fixedly coupled to pusher 724, and an outer portion that is fixedly coupled to handle housing 704. Moreover, holder 722 may include the rail configured to be slidably received within linear track 719 to prevent rotation of second tubular portion 714 as second tubular portion 714 axially moves relative to handle housing 704, which extends between the inner portion and the outer portion of holder 722.

Figure 8A:
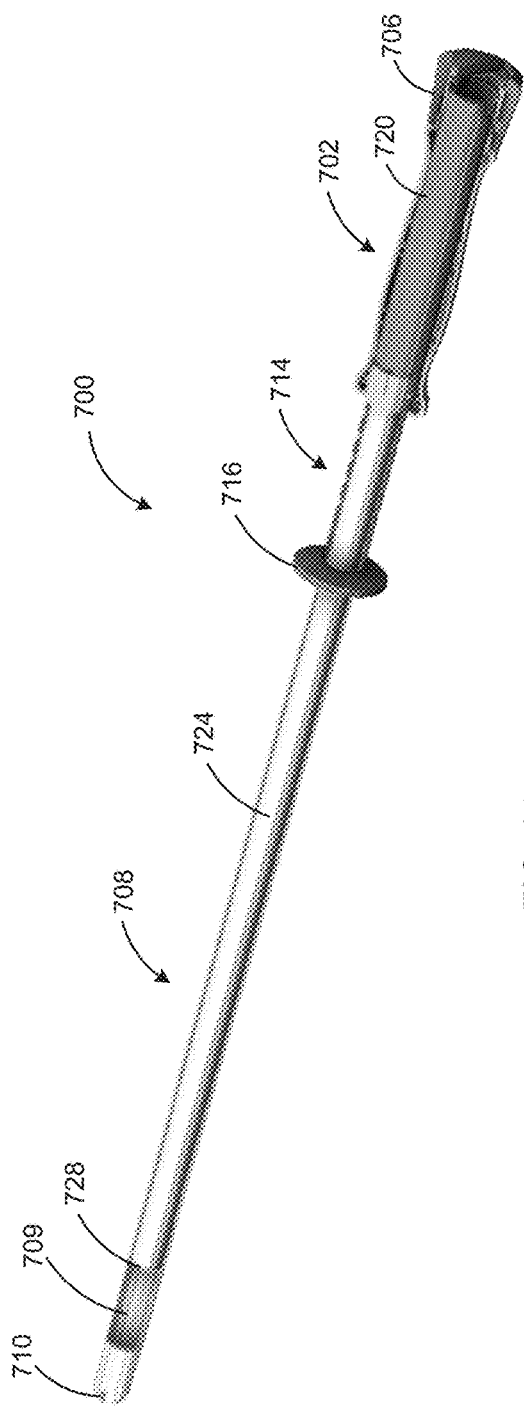
FIGS. 8A and 8B illustrate delivering the negative pressure bypass system using the introducer device of FIGS. 7A to 7G.
Figure 8B:
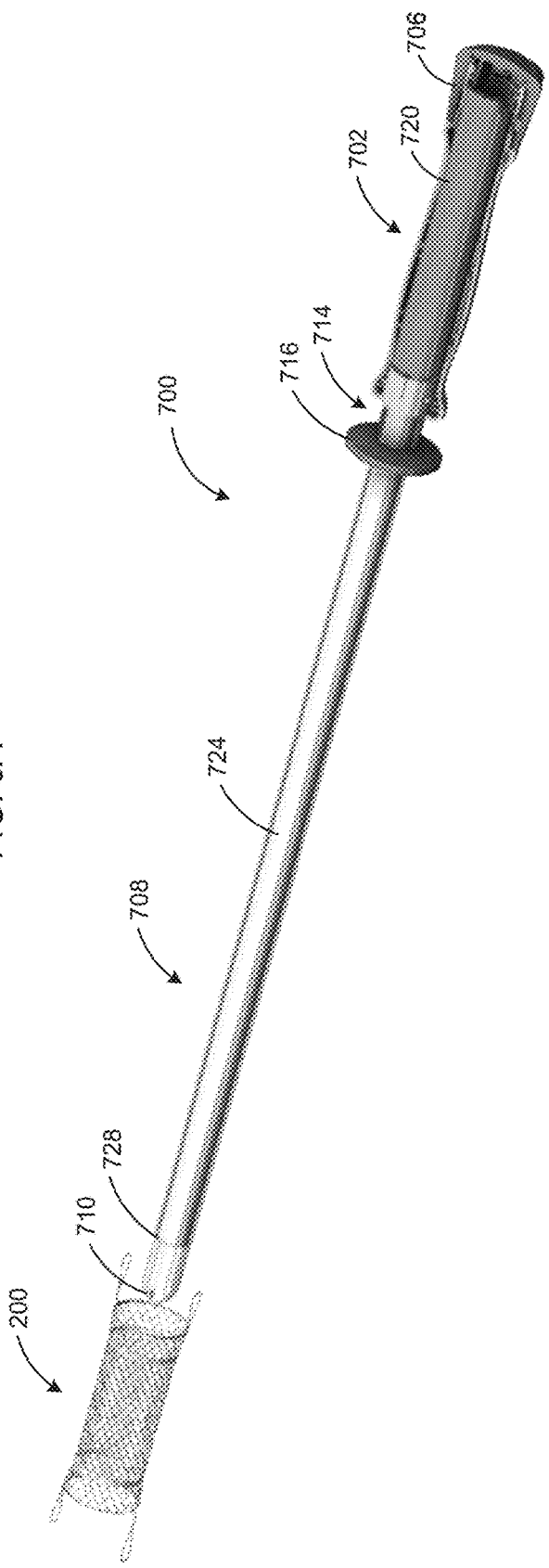

Moreover, pusher 724 may be formed of a flexible material to facilitate navigation introducer 700 through the patient's GI tract. Moreover, pusher 724 may be slidably disposed within lumen 709 of first tubular portion 708 and the lumen of second tubular portion 714, such that first tubular portion 708 and second tubular portion 714 may move axially relative to pusher 724, e.g., via rotation of knob 706 as described above, which pusher 724 and handle portion 702 relative stationary relative to the patient and the target site within the GI tract. Upstream end 728 may be sized and shaped to engage with and maintain bypass device 200 in position relative to the target site as first tubular portion 708 is moved axially relative to bypass device 200 and pusher 724 in the downstream direction, as shown in FIG. 8A (bypass device 200 omitted for brevity). Accordingly, as first tubular portion 708 is moved axially in the downstream direction, pusher 724 causes bypass device 200 to apply a force against the plurality of tabs of upstream tip 710 of first tubular portion 708, to thereby cause upstream tip 710 to transition from the closed configuration to the open configuration and permit bypass device 200 to pass therethrough. As shown in FIG. 8B, when bypass device 200 is fully exposed from lumen 709 of first tubular portion 708, bypass device 200 may transition from its collapsed delivery state to its expanded deployed state at the target site within the GI tract, e.g., via self-expansion.

Referring again to FIG. 7A, introducer 700 further may include safety clip 715 configured to prevent premature deployment of bypass device 200. As shown in FIG. 7A, safety clip 715 may be sized and shaped to engage with second tubular portion 714, between stop 716 and handle housing 704. For example, safety clip 715 may include a rail (not shown) sized and shaped to be received by linear track 719 of second tubular portion 714, to thereby removably secure safety clip 715 to second tubular portion 714. When safety clip 715 is engaged with second tubular portion 714, as shown in FIG. 7A, axial translation of second tubular portion 714 relative to handle housing 704 is prevented, as the rail of handle housing 704 may not move axially along linear track 719, as described above. Accordingly, during delivery of bypass device 200 via introducer 700, first tubular portion 708 may be inserted through the patient's anus and into the GI tract, while safety clip 715 is engaged with second tubular portion 714. When the user confirms that upstream tip 710 is in the desired position relative to the target site, such that bypass device 200 may be deployed at the target site within the GI tract, safety clip 715 may be removed from second tubular portion 714, to thereby permit actuation of handle portion 702 when bypass device 200 is ready for deployment.

Figure 7E:
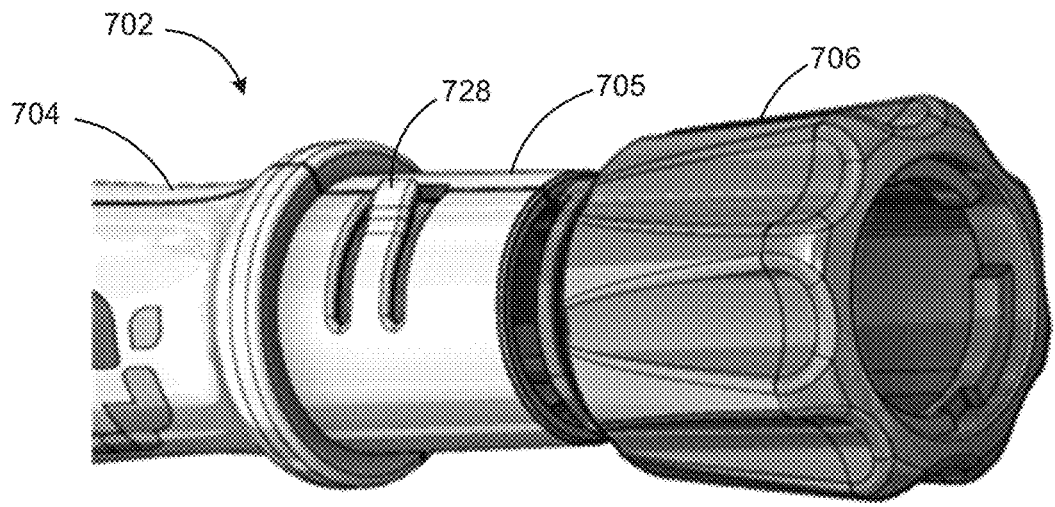
Figure 7F:
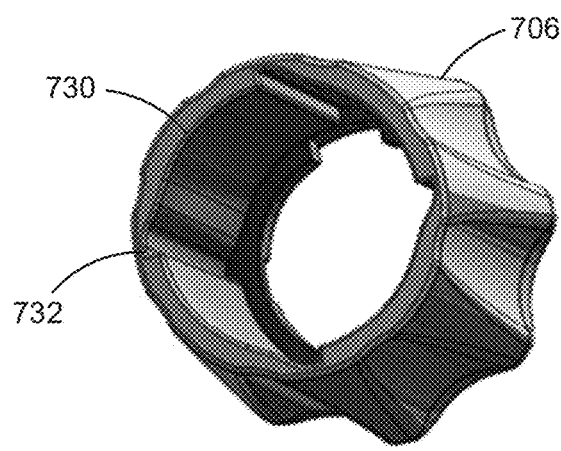
Figure 7G:
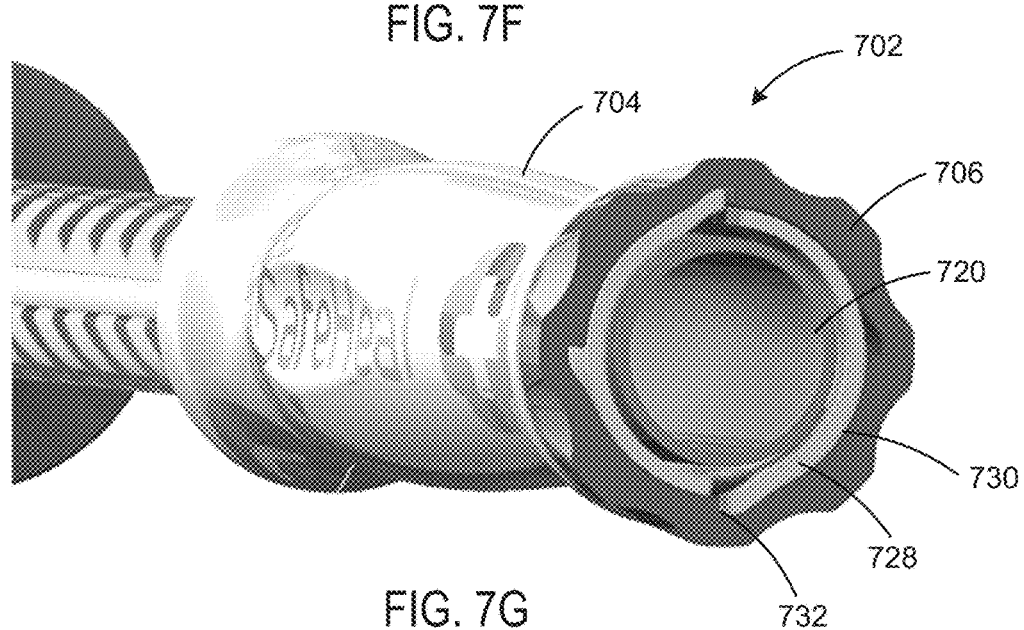

Referring now to FIGS. 7E to 7G, actuation of knob 706 may be restricted in a single direction during deploying of bypass device 200 at the target site. For example, as shown in FIG. 7E, downstream portion 705 of handle housing 704 may be configured to rotatably engage with knob 706. Specifically, downstream portion 705 may be sized and shaped to be received by an interior channel extending through at least a portion of knob 706, such that knob 706 may be rotated relative to downstream portion 705. As shown in FIG. 7E, downstream portion 728 may include one or more flexible tabs 728 extending circumferentially along at least a portion of downstream portion 705. Flexible tabs 728 may each be configured to transition between a radially compressed state where they extend radially inward, and a radially expanded state where they extend radially outward. Moreover, flexible tabs 728 may be biased toward the radially expanded state, such that a force is required to transition flexible tabs 728 to the radially compressed state.

As shown in FIG. 7F, an inner surface of knob 706 defining the interior channel of knob 706 may include one or more grooves 730 configured to slidably engage with one or more flexible tabs 728 as knob 706 is rotated relative to handle housing 704. Grooves 730 each may have a profile having stop feature 732 such that rotation of knob 706 in a first direction relative to handle housing 704 is permitted, while rotation of knob 706 in a second direction opposite to the first direction relative to handle housing 704 is prevented upon engagement of one or more flexible tabs 728 and stop feature 732 of one or more grooves 730 in the radially expanded state, as shown in FIG. 7G. Although FIG. 7G illustrates two flexible tabs 728, and four grooves 730, as will be understood by a person having ordinary skill in the art, handle portion 702 may include more or less flexible tabs and grooves. As will be understood by a person having ordinary skill in the art, introducer 700 may be used to deliver any of the bypass device anchors described herein, e.g., bypass device 1000, 1100, 1200, 1300, 1400, 1500, 1700, 1800.

Figure 9:
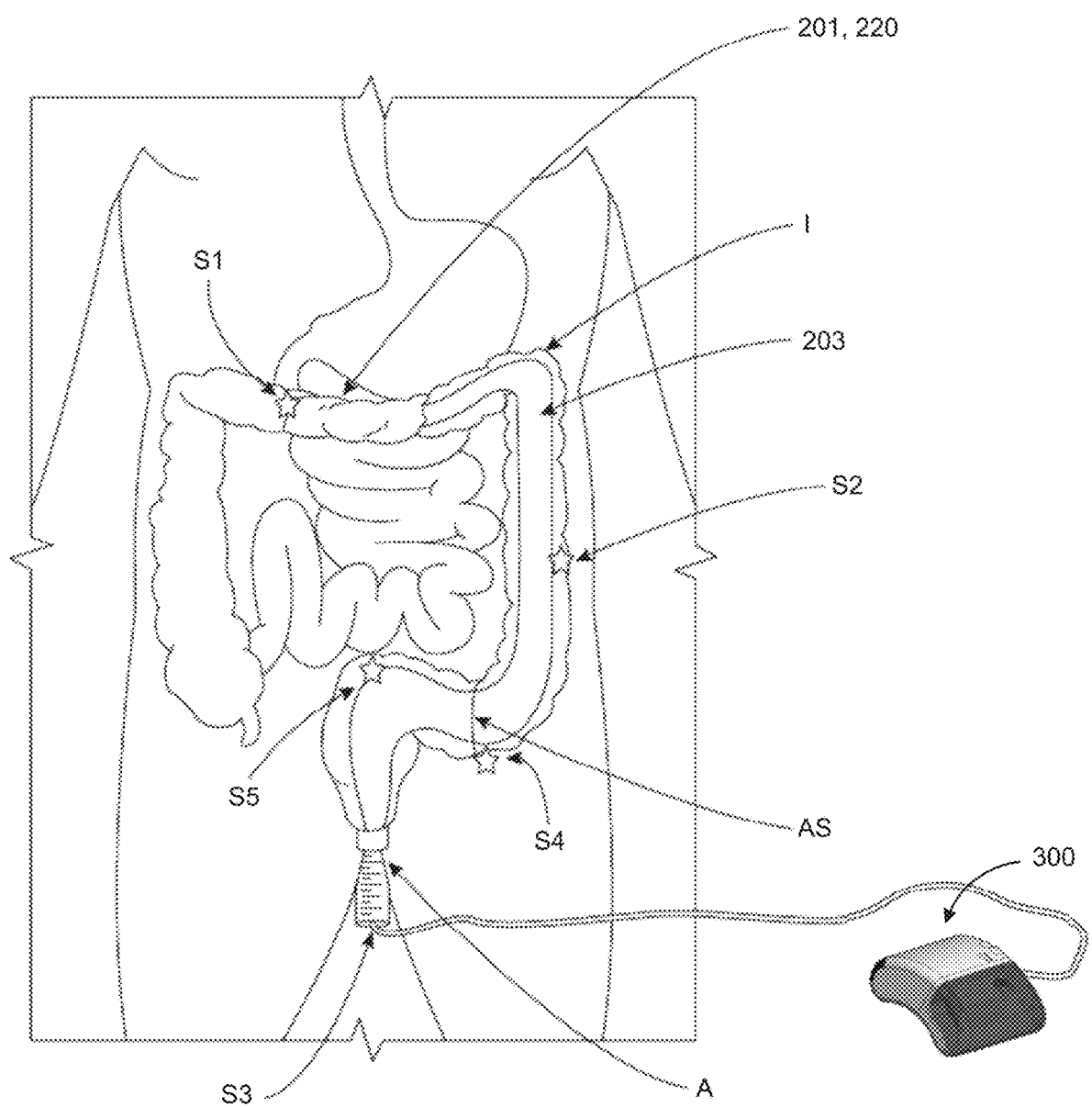
FIG. 9 illustrates an alternative exemplary negative pressure bypass system implanted within a patient anatomy, constructed in accordance with the principles of the present disclosure.

Referring now to FIG. 9, another exemplary system for monitoring bypass device 200 for protecting intestinal anastomosis AS using system 100 and one or more additional sensors is provided. As shown in FIG. 9, inner and outer anchors 201, 220 may be deployed and secured at a target site within intestine I, upstream of intestinal anastomosis AS, to thereby secure bypass device 200 within the patient's GI tract, such that sheath 203 extends from inner and outer anchors 201, 220, through intestine I, across anastomosis AS, and out of the patient's anus A. Moreover, one or more suction tubes, e.g., suction tubes 214, 216, may extend from the negative pressure chamber of bypass device 200, through intestine I and out of the patient's anus A, and fluidicly coupled to negative pressure system 300, as described above.

As shown in FIG. 9, one or more additional sensors may be operatively coupled to system 300 for monitoring bypass device 200. For example, sensor S1 may be disposed on at least one of inner or outer anchors 201, 220, and configured to generate one or more signals indicative of the pressure between inner and outer anchors 201, 220 and intestine I. Additionally or alternatively, sensor S1 may be configured to generate one or more signals indicative of the position of S1 within intestine I. Moreover, sensors S2 and/or S3 may be disposed along a length sheath 203, and may be configured to generate one or more signals indicative of the position of S2 and S3, respectively, within intestine I. Accordingly, based on the position measurements of S1, S2, and S3, the controller of system 300 may determine the relative positions between sensors S1, S2, S3, and may further determine if sheath 203 is, e.g., bunching, and/or if inner and outer anchors 201, 220 are, e.g., slipping within intestine I based on the position data. In addition, sensor S4 and/or sensor S5 may be disposed on the outer surface of sheath 203 along a length of sheath 203, and may be configured to generate one or more signals indicative of the presence of one or more substances, e.g., gases such as methane or hydrogen sulfide, which may be indicative of an anastomotic leak. Accordingly, based on the position measurements of sensors S4, S5, the controller of system 300 may determine whether a particular substance is detected within intestine I, and further may determine if there is an anastomotic leak based on the presence of the substance. As described above, system 300 may generate an alert responsive to determinations based on one or more parameters measured by the one or more additional sensors, e.g., sensors S1, S2, S3, S4, S5. For example, based on the sensed data, system 300 may generate an alert to inform a user when sheath 203 is bunching, inner and outer anchors 201, 220 are slipping, and/or there is an anastomotic leak.

Referring now to FIGS. 10A to 18C, alternative exemplary anchors for securing the bypass device at the target site within the GI tract are provided. For example, referring now to FIGS. 10A and 10B, bypass device 1000 for providing an internal bypass at a target site within the GI tract of the patient is provided. As shown in FIG. 10A, bypass device 1000 includes anchor 1001, and elongated flexible sheath 1002 coupled to anchor 1001 and extending therefrom in a downstream direction. Like sheath 203, sheath 1002 has an outer surface and an internal channel for allowing passage of feces and other waste matter therethrough. Sheath 1002 has a length selected to extend from the target site in the GI tract through the patient's intestines and anus to a location external to the patient. In some embodiments, the downstream end of sheath 1002 may be coupled to a collection vessel (not shown) external to the patient's body for collecting feces and other waste matter therein. Sheath 1002 may be formed of a biocompatible elastomer material such as, e.g., silicone or polyurethane.

Unlike bypass device 200, bypass device 1000 may include a single anchor, e.g., anchor 1001. Like the anchors of bypass device 200, anchor 1001 may be formed by a stent/scaffold, e.g., a self-expandable braided wire mesh, coupled to sheath 1002 and configured to provide an outward radial force against the walls of the intestine at the target site. Accordingly, anchor 1001 functions secure bypass device at the target site in conjunction with the negative pressure system, and to hold open the target area within the GI tract such that feces and other waste matter may pass through anchor 1001 and sheath 1002 without contacting the walls surrounding the anastomosis site. For example, as shown in FIG. 10B, an upstream region of sheath 1002 may extend through the lumen of anchor 1001, and may be coupled to an inner surface of stent 1001 via upstream scaling ring 1006 and downstream sealing ring 1004, thereby forming negative pressure chamber 1008 defined by an outer surface of sheath 1002, upstream scaling ring 1006, downstream sealing ring 1004, and the portion of anchor 1001 between upstream sealing ring 1006 and downstream sealing ring 1004. Anchor 1001 and sheath 1002 for use with bypass device 1000 may be constructed as described in U.S. Pat. Nos. 9,339,272 and 9,980,727 to Khosrovaninejad, the entire contents of each of which are incorporated herein by reference.

As described above, anchor 1001 may be used in conjunction with the negative pressure systems described herein to evacuate fluid from negative pressure chamber 1008 via one or more suction/fluid inlet tubes, e.g., suction tubes 1012, 1014, fluidicly coupled to an external pump, to thereby create a vacuum within negative pressure chamber 1008, which pulls intestinal tissue towards and at least partially through plurality of openings 1003 of anchor 1001, to thereby secure anchor 1001 at the target site. Although FIGS. 10A and 10B illustrate two suction tubes, as will be understood by a person having ordinary skill in the art, bypass device 1000 may include more or less than two suction tubes for generating the desired vacuum within negative pressure chamber 1008. As shown in FIG. 10B, the upstream regions of suction tubes 1012, 1014 may extend through downstream sealing ring 1004 and may be disposed within negative pressure chamber 1008.

Moreover, the upstream regions of suction tubes 1012, 1014 may include a plurality of inlet ports 1013, 1015, respectively, sized and shaped to evacuate fluid therethrough, sufficient to create the vacuum within negative pressure chamber 1008. Inlet ports 1013, 1015 may be distributed spatially evenly along the length of the upstream regions of suction 1012, 1014. Alternatively, the spatial distribution of inlet ports 1013, 1015 may be selected to create a desired vacuum within negative pressure chamber 1008. Preferably, the upstream regions of suction tubes 1012, 1014 may be equally spaced apart within negative pressure chamber 1008 along the circumference of sheath 1002. Suction tubes 1012, 1014 may extend from within negative pressure chamber 1008, through downstream sealing ring 1004, and along the outer surface of sheath 1002 and out the patient's anus, such that the downstream ends of suction tubes 1012, 1014 may be fluidicly coupled to the external pump of the negative pressure system for creating the vacuum within negative pressure chamber 1008. In some embodiments, at least a portion of suction tubes 1012, 1014 may extend within the wall of sheath 1002, e.g., within the membrane forming sheath 1002.

In some embodiments, the upstream end of sheath 1002 may extend towards the upstream end of anchor 1001, and may be coupled to the upstream end of anchor 1001 via upstream covering ring 1010 extending along the periphery of the upstream end of anchor 1001, to thereby securely fasten sheath 1002 to anchor 1001, as shown in FIG. 10A. Moreover, anchor 1001 may include one or more downstream retrieval loops 1016 extending from a downstream end of anchor 1001, and/or one or more upstream retrieval loops 1018 extending from an upstream end of anchor 1001 for facilitating removal of bypass device 1000, e.g., after the anastomosis has fully healed. For example, a retrieval device, e.g., an endoscopic grasper, may be introduced through the lumen of sheath 1002 toward the lumen of anchor 1001, to thereby engage with upstream retrieval loops 1018, such that a force may be applied to the downstream portion of the retrieval device to pull on upstream retrieval loops 1018 in the downstream direction. Accordingly, the upstream end of anchor 1001 may be inverted into the lumen of anchor 1001 towards the lumen of sheath 1002 via the pulling force on upstream retrieval loops 1018, to thereby detach anchor 1001 from the intestinal tissue surrounding anchor 1001, e.g., mucosal ingrowth that may have formed on anchor 1001. The retrieval device may then be disengaged from upstream retrieval loops 1018, and subsequently engaged with downstream retrieval loops 1016, to thereby apply a pulling force to downstream retrieval loops 1016 in the downstream direction and remove bypass device 1000 from the patient's body.

Figure 11:
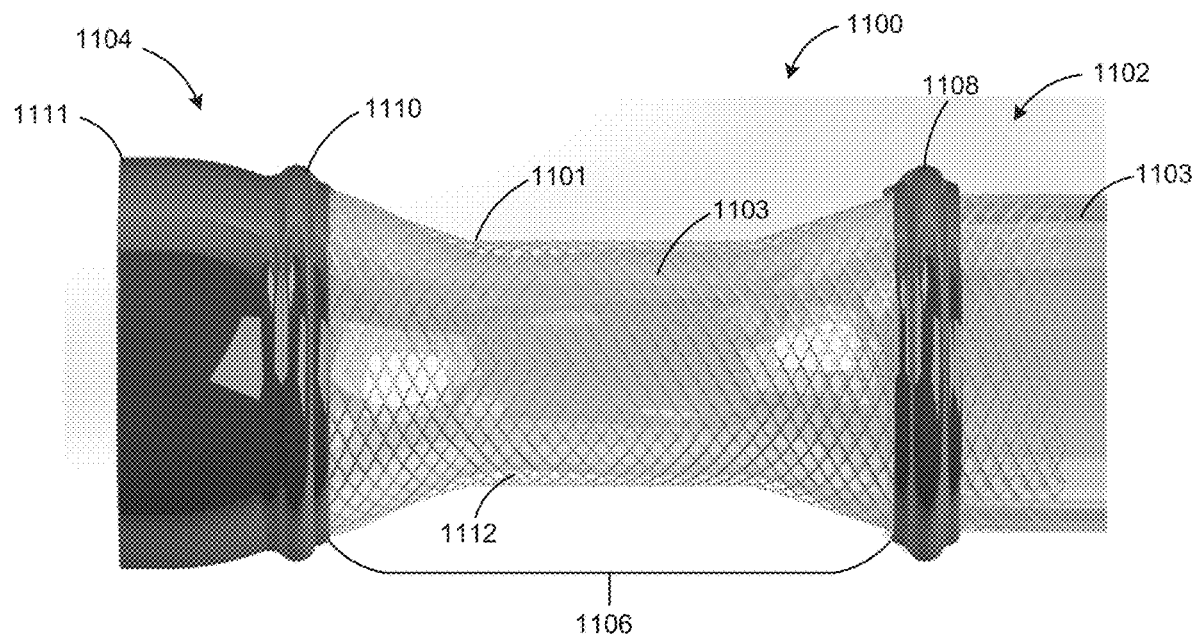
Figure 12:
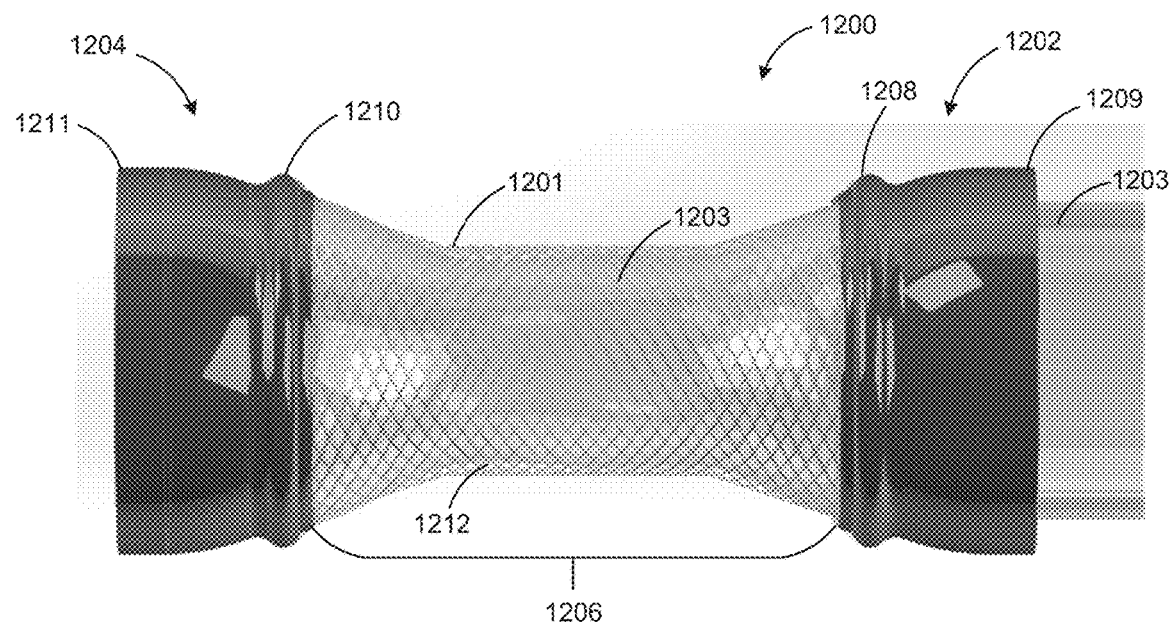
Figure 13:
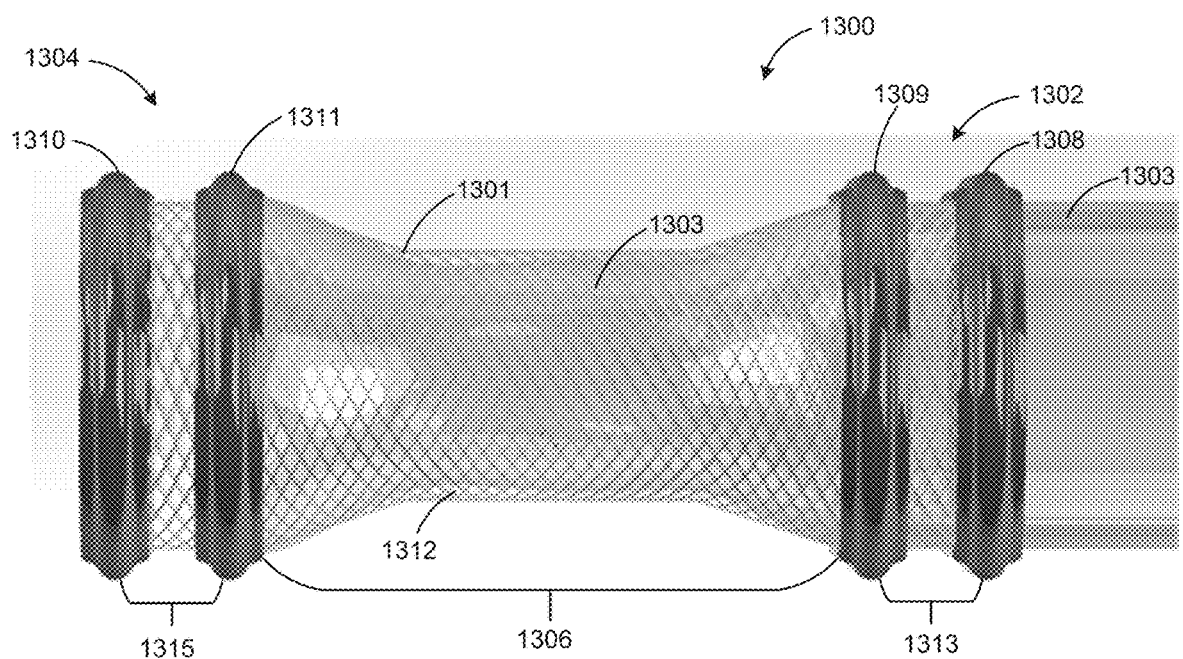
Figure 14:
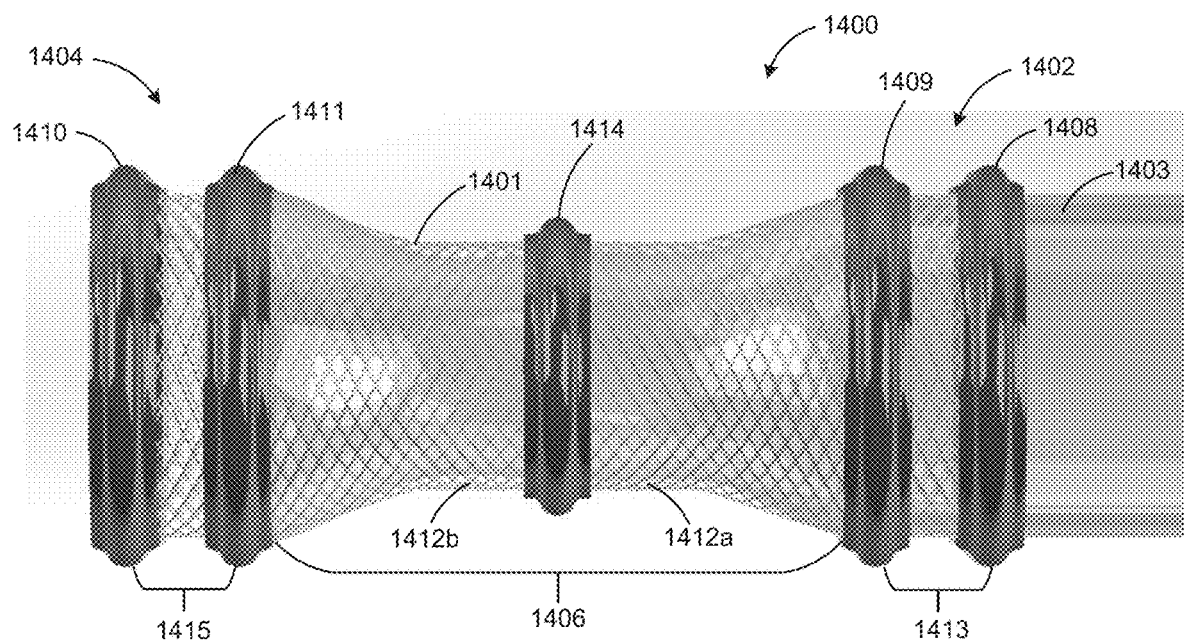
Figure 15A:
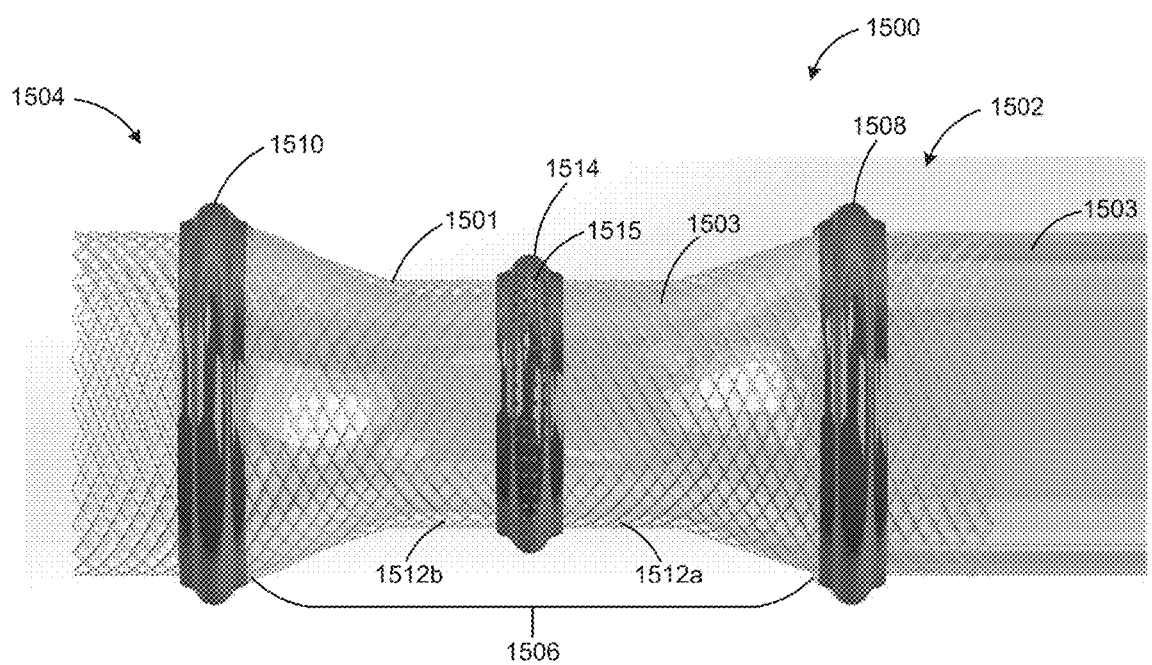
Figure 17:
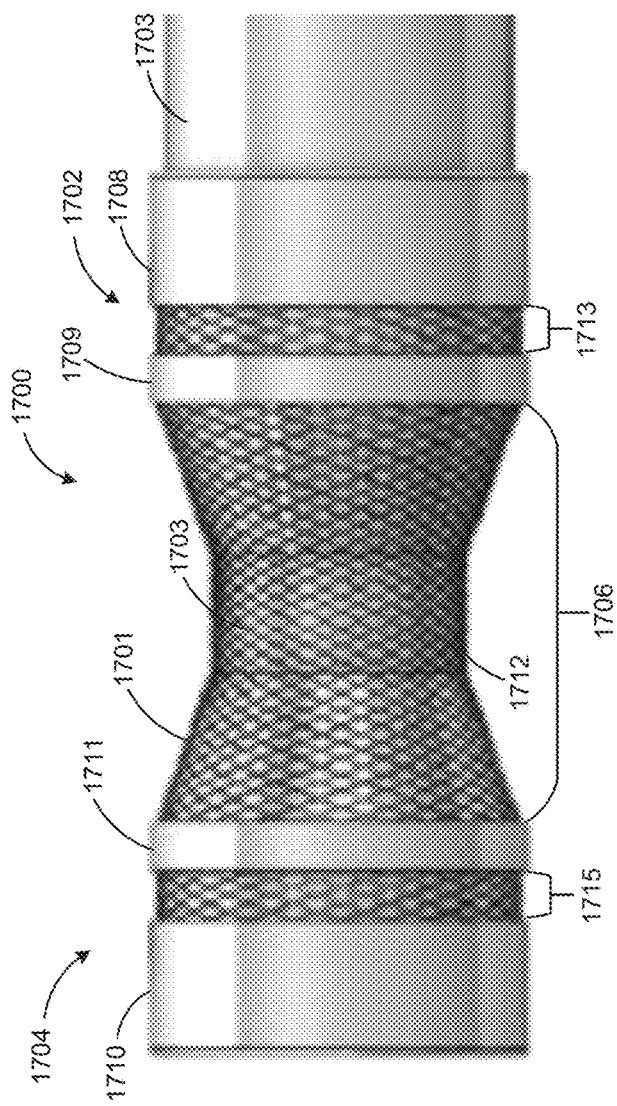
FIG. 17 illustrates another alternative exemplary implantable portion of the negative pressure bypass system, constructed in accordance with the principles of the present disclosure.
Figure 18A:
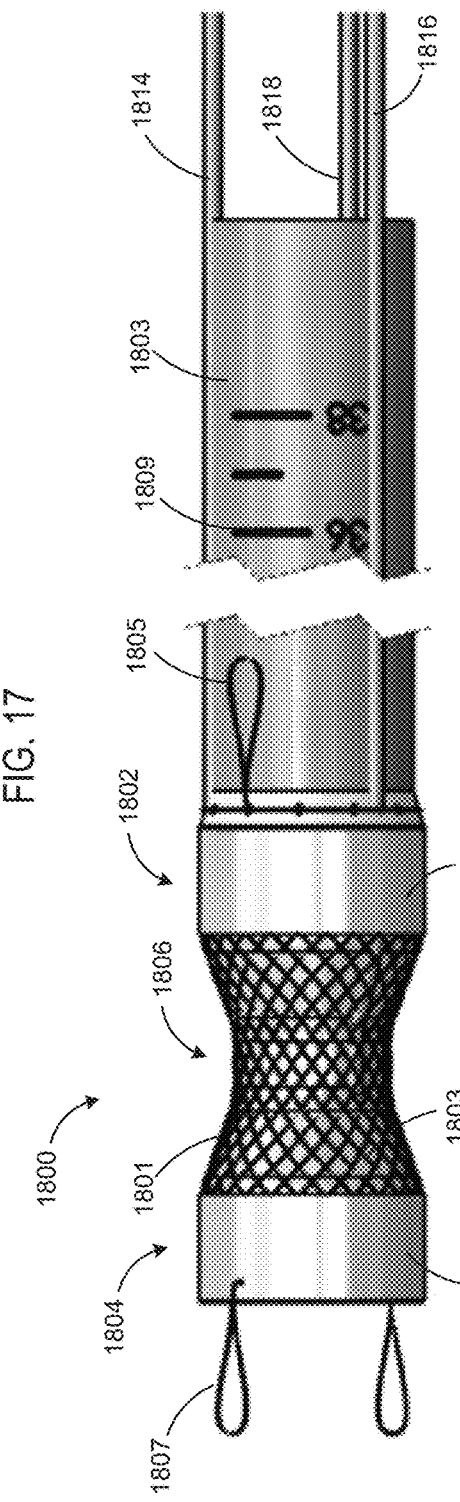

Anchor 1101 of FIG. 11, anchor 1201 of FIG. 12, anchor 1301 of FIG. 13, anchor 1401 of FIG. 14, anchor 1501 of FIG. 15A, anchor 1701 of FIG. 17, and anchor 1801 of FIG. 18A each may be constructed similar to anchor 1001 in that they each may be formed of a self-expandable braided wire mesh stent/scaffold that may be coupled to an outer surface of an inner sheath, e.g., sheaths 1103, 1203, 1303, 1403, 1503, 1703, 1803 respectively, via at least upstream and downstream sealing rings to thereby define one or more negative pressure chambers for creating a vacuum and evacuating fluid via one or more suction tubes fluidly coupled to the one or more negative pressure chambers. Unlike anchor 1001, but like inner anchor 201, the stent/scaffold forming anchors 1101, 1201, 1301, 1401, 1501, 1701, 1801 may have a recessed middle region between flared upstream and downstream regions, e.g., a bone-shaped profile that makes an hourglass, to thereby improve negative pressure chamber engagement with the intestinal tissue. For example, the recessed middle region may have an outer diameter that is less than the outer diameters of the upstream and downstream regions to thereby provide a larger volume between the outer surface of the respective anchors and the wall of the intestine.

Referring now to FIG. 11, anchor 1101 of bypass device 1100 may include downstream region 1102, upstream region 1104, and recessed middle region 1106 extending between downstream region 1102 and upstream region 1104. Middle region 1106 may have an outer diameter that is less than the outer diameters of downstream region 1102 and upstream region 1104, thereby providing a larger volume between the outer surface of middle region 1106 and the wall of the intestine to improve negative pressure chamber engagement with the intestinal tissue during application of the vacuum. In some embodiments, anchor 1101 may be symmetric such that downstream region 1102 may have an outer diameter that is equal to the outer diameter of upstream region 1104. Moreover, sheath 1103 of bypass device 1100 may be coupled to anchor 1101 via downstream sealing ring 1108 and integrated upstream sealing ring 1110, to thereby define negative pressure chamber 1112 between the outer surface of sheath 1103, downstream sealing ring 1108, upstream sealing ring 1110, and middle region 1106 of anchor 1101.

As shown in FIG. 11, integrated upstream sealing ring 1110 may include an integrated upstream edge sealing ring portion 1111 configured to be disposed along the upstream edge of anchor 1101, thereby forming a soft, flexible upstream leading edge of anchor 1101. For example, integrated upstream edge sealing ring portion 1111 may prevent damage to the intestinal tissue adjacent to the upstream end of anchor 1101. In addition, integrated upstream edge sealing ring portion 1111 provides a longer sealing surface along the upstream region 1104 and flexibility to aid in retrieval of bypass device 1100. Moreover, integrated upstream edge sealing ring portion 1111 inhibits mucosal ingrowth on at least upstream region 1104 of anchor 1101. Downstream sealing ring 1108 and integrated upstream sealing ring 1110, 1111 may be compression molded onto or overmolded directly over the stent/scaffold of anchor 1101 and sheath 1103, or alternatively, may be thermally bonded or solvent bonded thereto. For example, downstream sealing ring 1108 and integrated upstream sealing ring 1110, 1111 may be formed of a moldable thermoplastic material such as, thermoplastic urethane (TPU), thermoplastic elastomer (TPE), and/or thermoplastic vulcanizate (TPV). One or more suction tubes (not shown) may be disposed across downstream sealing ring 1108, such that one or more inlet ports of the one or more suction tubes may be disposed within negative pressure chamber 1112. Upon actuation of the negative pressure system, e.g., an external pump fluidicly coupled to the one or more suction tubes, a vacuum having a predetermined pressure may be created within negative pressure chamber 1112 to thereby pull intestinal tissue toward anchor 1101 and secure bypass device 1100 at the target site. At least some intestinal tissue may be pulled through at least some openings of the stent/scaffold of middle region 1106.

Referring now to FIG. 12, anchor 1201 of bypass device 1200 may include downstream region 1202, upstream region 1204, and recessed middle region 1206 extending between downstream region 1202 and upstream region 1204. Middle region 1206 may have an outer diameter that is less than the outer diameters of downstream region 1202 and upstream region 1204, thereby providing a larger volume between the outer surface of middle region 1206 and the wall of the intestine to improve negative pressure chamber engagement with the intestinal tissue during application of the vacuum. In some embodiments, anchor 1201 may be symmetric such that downstream region 1202 may have an outer diameter that is equal to the outer diameter of upstream region 1204. Moreover, sheath 1203 of bypass device 1200 may be coupled to anchor 1201 via integrated downstream sealing ring 1208 and integrated upstream sealing ring 1210, to thereby define negative pressure chamber 1212 between the outer surface of sheath 1203, downstream sealing ring 1208, upstream sealing ring 1210, and middle region 1206 of anchor 1201.

As shown in FIG. 12, integrated downstream sealing ring 1208 may include an integrated downstream edge sealing ring portion 1209 configured to be disposed along the downstream edge of anchor 1201, thereby forming a soft, flexible downstream trailing edge of anchor 1201. For example, integrated downstream edge scaling ring portion 1209 may prevent damage to the intestinal tissue and the outer surface of sheath 1203 adjacent to the downstream end of anchor 1201. In addition, integrated upstream sealing ring 1210 may include an integrated upstream edge sealing ring portion 1211 configured to be disposed along the upstream edge of anchor 1201, thereby forming a soft, flexible upstream leading edge of anchor 1201. For example, integrated upstream edge sealing ring portion 1211 may prevent damage to the intestinal tissue adjacent to the upstream end of anchor 1201. Moreover, integrated downstream edge scaling ring portion 1209 and integrated upstream edge sealing ring portion 1211 provide a longer sealing surface along the downstream region 1202 and upstream region 1204, respectively, and flexibility to aid in retrieval of bypass device 1200. In addition, integrated downstream edge sealing ring portion 1209 and integrated upstream edge sealing ring portion 1211 inhibit mucosal ingrowth on at least downstream region 1202 and upstream region 1204 of anchor 1201.

Integrated downstream sealing ring 1208, 1209 and integrated upstream sealing ring 1210, 1211 may be compression molded onto or overmolded directly over the stent/scaffold of anchor 1201 and sheath 1203, or alternatively, may be thermally bonded or solvent bonded thereto. For example, integrated downstream sealing ring 1208, 1209 and integrated upstream scaling ring 1210, 1211 may be formed of a moldable thermoplastic material such as, thermoplastic urethane (TPU), thermoplastic elastomer (TPE), and/or thermoplastic vulcanizate (TPV). One or more suction tubes (not shown) may be disposed across integrated downstream sealing ring 1208, 1209 such that one or more inlet ports of the one or more suction tubes may be disposed within negative pressure chamber 1212. Upon actuation of the negative pressure system, e.g., an external pump fluidicly coupled to the one or more suction tubes, a vacuum having a predetermined pressure may be created within negative pressure chamber 1212 to thereby pull intestinal tissue toward anchor 1201 and secure bypass device 1200 at the target site. At least some intestinal tissue may be pulled through at least some openings of the stent/scaffold of middle region 1206.

Referring now to FIG. 13, anchor 1301 of bypass device 1300 may include downstream region 1302, upstream region 1304, and recessed middle region 1306 extending between downstream region 1302 and upstream region 1304. Middle region 1306 may have an outer diameter that is less than the outer diameters of downstream region 1302 and upstream region 1304, thereby providing a larger volume between the outer surface of middle region 1306 and the wall of the intestine to improve negative pressure chamber engagement with the intestinal tissue during application of the vacuum. In some embodiments, anchor 1301 may be symmetric such that downstream region 1302 may have an outer diameter that is equal to the outer diameter of upstream region 1304.

Moreover, sheath 1303 of bypass device 1300 may be coupled to anchor 1301 via first downstream sealing ring 1308 and first upstream sealing ring 1310, to thereby define negative pressure chamber 1312 between the outer surface of sheath 1303, first downstream scaling ring 1308, first upstream sealing ring 1310, and middle region 1306 of anchor 1301. In some embodiments, first downstream sealing ring 1308 may be disposed along the downstream edge of anchor 1301 and/or first upstream sealing ring 1310 may be disposed along the upstream edge of anchor 1301, thereby forming a soft, flexible downstream trailing edge of anchor 1301 and/or a soft, flexible upstream trailing edge of anchor 1301, respectively. For example, first downstream sealing ring 1308 may prevent damage to the intestinal tissue and the outer surface of sheath 1303 adjacent to the downstream end of anchor 1301, and first upstream scaling ring 1310 may prevent damage to the intestinal tissue adjacent to the upstream end of anchor 1301. First downstream sealing ring 1308 and first upstream sealing ring 1310 may be compression molded onto or overmolded directly over the stent/scaffold of anchor 1301 and sheath 1303, or alternatively, may be thermally bonded or solvent bonded thereto. For example, first downstream sealing ring 1308 and first upstream sealing ring 1310 may be formed of a moldable thermoplastic material such as, thermoplastic urethane (TPU), thermoplastic elastomer (TPE), and/or thermoplastic vulcanizate (TPV).

As shown in FIG. 13, bypass device 1300 further may include second downstream scaling ring 1309 disposed on anchor 1301 upstream of first downstream scaling ring 1308, as well as second upstream sealing ring 1311 disposed on anchor 1301 downstream of first upstream sealing ring 1310. Neither second downstream sealing ring 1309 nor second upstream scaling ring 1311 are coupled to sheath 1303. Accordingly, second downstream sealing ring 1309 and second upstream sealing ring 1311 may be compression molded onto or overmolded directly over the stent/scaffold of anchor 1301, or alternatively, may be thermally bonded or solvent bonded thereto. For example, second downstream sealing ring 1309 and second upstream sealing ring 1311 may be formed of a moldable thermoplastic material such as, thermoplastic urethane (TPU), thermoplastic elastomer (TPE), and/or thermoplastic vulcanizate (TPV).

One or more suction tubes (not shown) may be disposed across first downstream sealing ring 1308 such that one or more inlet ports of the one or more suction tubes may be disposed within negative pressure chamber 1312. Upon actuation of the negative pressure system, e.g., an external pump fluidically coupled to the one or more suction tubes, a vacuum having a predetermined pressure may be created within negative pressure chamber 1312 to thereby pull intestinal tissue toward anchor 1301 and secure bypass device 1300 at the target site. At least some intestinal tissue may be pulled through at least some openings of the stent/scaffold of middle region 1306. Moreover, as the vacuum created within negative pressure chamber 1312 causes intestinal tissue to be pulled toward anchor 1301, the intestinal tissue may contact the outer surface of second downstream sealing ring 1309 and second upstream sealing ring 1311, thereby creating downstream suction chamber 1313 defined by sheath 1303, first and second downstream sealing rings 1308, 1309, and the intestinal tissue surrounding anchor 1301 between first and second downstream sealing rings 1308, 1309, and upstream suction chamber 1315 defined by sheath 1303, first and second upstream sealing rings 1310, 1311, and the intestinal tissue surrounding anchor 1301 between first and second upstream sealing rings 1310, 1311. Accordingly, the vacuum created within downstream suction chamber 1313 and upstream suction chamber 1315 may facilitate engagement of bypass device 1300 to the intestinal wall.

Referring now to FIG. 14, bypass device 1400 is provided. Bypass device 1400 may be constructed similar to bypass device 1300. For example, bypass device 1400 may include anchor 1401 having upstream, downstream, and middle regions 1402, 1404, 1406, first and second downstream sealing rings 1408, 1409 for generating downstream suction chamber 1413, and first and second upstream sealing rings 1410, 1411 for generating upstream suction chamber 1415, which corresponds to anchor 1301 having upstream, downstream, and middle regions 1302, 1304, 1306, first and second downstream sealing rings 1308, 1309 for generating downstream suction chamber 1313, and first and second upstream sealing rings 1310, 1311 for generating upstream suction chamber 1315, of bypass device 1300. Bypass device 1400 differs from bypass device 1300 in that bypass device 1400 may include middle sealing ring 1414, as shown in FIG. 14, configured to couple sheath 1403 to anchor 1401 within middle region 1406, thereby defining first negative pressure chamber 1412a defined by first downstream sealing ring 1408, middle sealing ring 1414, the upper surface of sheath 1403, and the portion of anchor 1401 between first downstream sealing ring 1408 and middle sealing ring 1414, and second negative pressure chamber 1412b defined by first upstream sealing ring 1410, middle sealing ring 1414, the upper surface of sheath 1403, and the portion of anchor 1401 between first upstream sealing ring 1410 and middle sealing ring 1414.

Accordingly, one or more suction tubes (not shown) may be disposed across first downstream sealing ring 1408 such that one or more inlet ports of the one or more suction tubes may be disposed within negative pressure chamber 1412a. Additionally, one or more additional suction tubes (not shown) may be disposed across first downstream sealing ring 1408 and middle sealing ring 1414 such that one or more inlet ports of the one or more additional suction tubes may be disposed within negative pressure chamber 1412b. Alternatively, the same one or more suction tubes may be disposed across first downstream sealing ring 1408 and middle sealing ring 1414 such that a first set of one or more inlet ports of the one or more suction tubes may be disposed within negative pressure chamber 1412a, and a second set of one or more inlet ports of the one or more suction tubes may be disposed within negative pressure chamber 1412b. Upon actuation of the negative pressure system, e.g., an external pump fluidicly coupled to the suction tubes, a vacuum having a predetermined pressure may be created within negative pressure chambers 1412a, 1412b to thereby pull intestinal tissue toward anchor 1401 and secure bypass device 1400 at the target site. At least some intestinal tissue may be pulled through at least some openings of the stent/scaffold of middle region 1406.

Moreover, as the vacuum created within negative pressure chamber 1412a causes intestinal tissue to be pulled toward anchor 1401, the intestinal tissue may contact the outer surface of second downstream sealing ring 1409, thereby creating downstream suction chamber 1413 defined by sheath 1403, first and second downstream sealing rings 1408, 1409, and the intestinal tissue surrounding anchor 1401 between first and second downstream sealing rings 1408, 1409. Similarly, as the vacuum created within negative pressure chamber 1412b causes intestinal tissue to be pulled toward anchor 1401, the intestinal tissue may contact the outer surface of second upstream sealing ring 1411, thereby creating upstream suction chamber 1415 defined by sheath 1403, first and second upstream sealing rings 1410, 1411, and the intestinal tissue surrounding anchor 1401 between first and second upstream sealing rings 1410, 1411. Accordingly, the vacuum created within downstream suction chamber 1413 and upstream suction chamber 1415 may facilitate engagement of bypass device 1400 to the intestinal wall. In some embodiments, the suction tubes fluidicly coupled to negative pressure chamber 1412a may be actuated independently from the suction tubes fluidicly coupled to negative pressure chamber 1412b, to thereby create a vacuum within negative pressure chamber 1412a having a different pressure than the vacuum created within negative pressure chamber 1412b.

Referring now to FIG. 15A, bypass device 1500 is provided. Bypass device 1500 may be constructed similar to bypass device 1400, except without second downstream and upstream sealing rings. For example, bypass device 1500 may include anchor 1501 having upstream, downstream, and middle regions 1502, 1504, 1506, downstream scaling ring 1508, and upstream sealing ring 1510, which corresponds to anchor 1401 having upstream, downstream, and middle regions 1402, 1404, 1406, downstream scaling ring 1408, and upstream scaling ring 1410 of bypass device 1400. Like bypass device 1400, bypass device 1500 also may include a middle sealing ring, e.g., middle sealing ring 1514, thereby defining first negative pressure chamber 1512a defined by downstream sealing ring 1508, middle sealing ring 1514, the upper surface of sheath 1503, and the portion of anchor 1501 between downstream scaling ring 1508 and middle sealing ring 1514, and second negative pressure chamber 1512b defined by upstream scaling ring 1510, middle sealing ring 1514, the upper surface of sheath 1503, and the portion of anchor 1501 between first upstream sealing ring 1510 and middle sealing ring 1514.

Figure 15B:
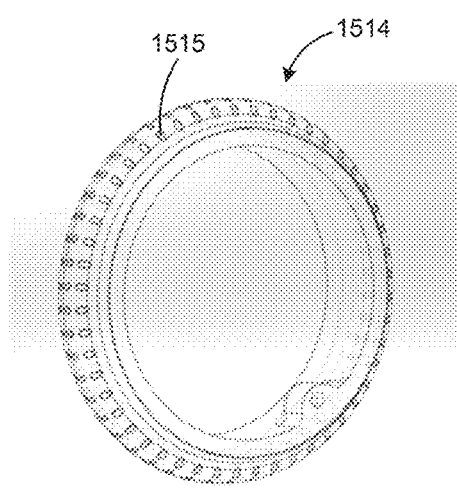
FIG. 15B is a perspective view of the middle sealing ring of the implantable portion of FIG. 15A.

However, middle scaling ring 1514 differs from middle sealing ring 1414 in that middle sealing ring 1514 may include a plurality of inlet ports 1515 configured to be fluidicly coupled to one or more suction tubes of the negative pressure system, and sized and shaped to evacuate fluid therethrough. For example, middle scaling ring 1514 may include a chamber configured to be fluidly coupled to plurality of inlet ports 1515 and to the one or more suction tubes. As shown in FIG. 15B, plurality of inlet ports 1515 may be spatially evenly distributed along the outer surface of middle sealing ring 1514. In some embodiments, plurality of inlet ports 1515 may only be distributed along an upstream side of middle sealing ring 1514, or alternatively, plurality of inlet ports 1515 may only point in the upstream direction, such that the suction is directed upstream to thereby create resistance to tension downstream and resist the main direction of peristaltic forces during operation.

A first set of one or more additional suction tubes (not shown) may be disposed across downstream sealing ring 1508, such that one or more inlet ports of the first set of one or more additional suction tubes may be disposed within negative pressure chamber 1512a, and a second set of one or more additional suction tubes (not shown) may be disposed across downstream sealing ring 1508 and middle sealing ring 1514 such that one or more inlet ports of the second set of one or more additional suction tubes may be disposed within negative pressure chamber 1512b. Alternatively, the same one or more additional suction tubes may be disposed across downstream sealing ring 1508 and middle sealing ring 1514 such that a first set of one or more inlet ports of the one or more additional suction tubes may be disposed within negative pressure chamber 1512a, and a second set of one or more inlet ports of the one or more additional suction tubes may be disposed within negative pressure chamber 1512b.

Upon actuation of the negative pressure system, e.g., an external pump fluidicly coupled to the suction tubes, a vacuum having a predetermined pressure may be created within negative pressure chambers 1512a, 1512b, to thereby pull intestinal tissue toward anchor 1501 and secure bypass device 1500 at the target site. At least some intestinal tissue may be pulled through at least some openings of the stent/scaffold of middle region 1506. Moreover, actuation of the negative pressure system may cause evacuation of fluid through inlet ports 1515 of middle sealing ring 1514, thereby creating a vacuum in the space between anchor 1501 and the inner wall of the intestine surrounding middle region 1506, which pulls intestinal tissue toward middle sealing ring 1514. For example, the intestinal tissue may be pulled to contact the sealing surface of middle sealing ring 1514, thereby creating a localized vacuum ring and protecting against vacuum leaks due to seal breach. In some embodiments, the suction tubes fluidicly coupled to negative pressure chamber 1512a, negative pressure chamber 1512b, and middle sealing ring 1514, each may be independently actuatable.

Figure 16A:
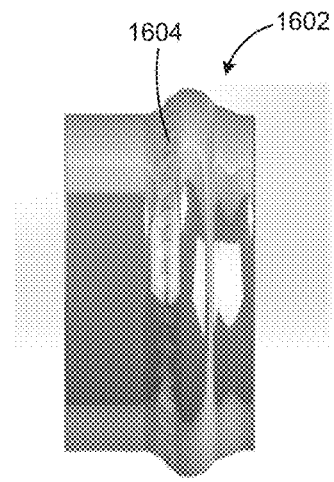
FIGS. 16A and 16B illustrate alternative exemplary sealing rings constructed in accordance with the principles of the present disclosure.
Figure 16B:
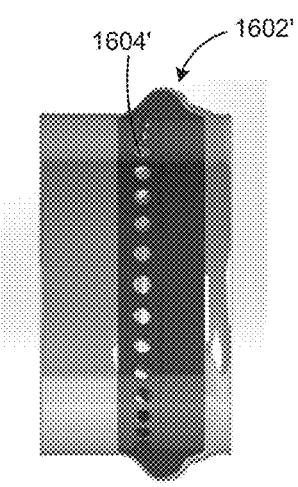

Referring now to FIGS. 16A and 16B, alternatively exemplary downstream scaling rings are provided. As shown in FIG. 16A, downstream sealing ring 1602 may include a plurality of inlet ports 1604 configured to be fluidicly coupled to one or more suction tubes of the negative pressure system, e.g., negative pressure system 300, and sized and shaped to evacuate fluid therethrough. For example, downstream sealing ring 1602 may include a chamber configured to be fluidly coupled to plurality of inlet ports 1604 and to the one or more suction tubes. As shown in FIG. 16A, plurality of inlet ports 1604 may be spatially evenly distributed along the outer surface of the upstream side of downstream sealing ring 1602, such that the suction is directed upstream to thereby create resistance to tension downstream and resist the main direction of peristaltic forces during operation. Alternatively, distribution of plurality of inlet ports 1602 along downstream sealing ring 1602 may not be limited to the upstream side of downstream sealing ring 1602. As shown in FIG. 16A, plurality of inlet ports 1604 may each have an oval-shaped profile. Alternatively, as shown in FIG. 16B, plurality of inlet ports 1604' of downstream sealing ring 1602', which may be constructed similar to downstream scaling ring 1602, may each have a circular-shaped profile.

As will be understood by a person having ordinary skill in the art, a scaling ring having a plurality of inlet ports for evacuating fluid therethrough (such as downstream sealing ring 1602) may be incorporated in any of the bypass devices described herein to facilitate securement of the respective bypass device at the target site within the patient's GI tract. Moreover, such a sealing ring is not limited for use as a downstream sealing ring, but also may be incorporated within the upstream sealing rings described herein. Such upstream sealing rings may have downstream facing inlet ports.

Referring now to FIG. 17, bypass device 1700 is provided. Bypass device 1700 may be constructed similar to bypass device 1200. For example, bypass device 1700 may include anchor 1701 having upstream, downstream, and middle regions 1702, 1704, 1706, first and second downstream sealing rings 1708, 1709 for generating downstream suction chamber 1713, and first and second upstream sealing rings 1710, 1711 for generating upstream suction chamber 1715. Bypass device 1700 differs from bypass device 1200 in that, like bypass device 1200, downstream sealing ring 1708 may include an integrated downstream edge sealing ring portion configured to be disposed along the downstream edge of anchor 1701, thereby forming a soft, flexible downstream trailing edge of anchor 1701, and upstream sealing ring 1710 may include an integrated upstream edge sealing ring portion configured to be disposed along the upstream edge of anchor 1701, thereby forming a soft, flexible upstream leading edge of anchor 1701. Accordingly, the integrated downstream and upstream edge scaling ring portions of downstream scaling ring 1708 and upstream sealing ring 1710 may prevent damage to the intestinal tissue adjacent the downstream and upstream ends of anchor 1701. Moreover, downstream sealing ring 1708 and upstream sealing ring 1710 provide a longer sealing surface along the downstream region 1702 and upstream region 1704, respectively, and flexibility to aid in retrieval of bypass device 1700. In addition, downstream sealing ring 1708 and upstream sealing ring 1710 inhibit mucosal ingrowth on at least downstream region 1702 and upstream region 1704 of anchor 1701.

One or more suction tubes (not shown) may be disposed across first downstream sealing ring 1708 such that one or more inlet ports of the one or more suction tubes may be disposed within negative pressure chamber 1712. Upon actuation of the negative pressure system, e.g., an external pump fluidicly coupled to the one or more suction tubes, a vacuum having a predetermined pressure may be created within negative pressure chamber 1712 to thereby pull intestinal tissue toward anchor 1701 and secure bypass device 1700 at the target site. At least some intestinal tissue may be pulled through at least some openings of the stent/scaffold of middle region 1706. Moreover, as the vacuum created within negative pressure chamber 1712 causes intestinal tissue to be pulled toward anchor 1701, the intestinal tissue may contact the outer surface of second downstream sealing ring 1709 and second upstream sealing ring 1711, thereby creating downstream suction chamber 1713 defined by sheath 1703, first and second downstream sealing rings 1708, 1709, and the intestinal tissue surrounding anchor 1701 between first and second downstream sealing rings 1708, 1709, and upstream suction chamber 1715 defined by sheath 1703, first and second upstream sealing rings 1710, 1711, and the intestinal tissue surrounding anchor 1701 between first and second upstream sealing rings 1710, 1711. Accordingly, the vacuum created within downstream suction chamber 1713 and upstream suction chamber 1715 may facilitate engagement of bypass device 1700 to the intestinal wall.

Referring now to FIGS. 18A to 18C, bypass device 1800 is provided. Bypass device 1800 may be constructed similar to bypass device 1200. For example, bypass device 1800 may include anchor 1801 having downstream, upstream, and middle regions 1802, 1804, 1806, and integrated downstream sealing ring 1808 including an integrated downstream edge sealing ring portion configured to be disposed along the downstream edge of anchor 1801 and integrated upstream sealing ring 1810 including an integrated upstream edge sealing ring portion configured to be disposed along the upstream edge of anchor 1801 to thereby form a soft, flexible downstream trailing edge and a soft, flexible upstream leading edge of anchor 1801, as shown in FIG. 18B. Moreover, sheath 1803 may be disposed within the lumen of anchor 1801, and coupled to integrated downstream sealing ring 1808 and integrated upstream sealing ring 1810 to thereby define negative pressure chamber 1812 between the outer surface of sheath 1803, integrated downstream sealing ring 1808, integrated upstream sealing ring 1810, and anchor 1801. As shown in FIG. 18A, sheath 1803 may extend downstream from anchor 1801.

As shown in FIG. 18A, anchor 1801 may include one or more downstream retrieval loops 1805 extending from a downstream end of anchor 1801, and/or one or more upstream retrieval loops 1807 extending from an upstream end of anchor 1801 for facilitating removal of bypass device 1800, e.g., after the anastomosis has fully healed. Retrieval loops 1805, 1807 may be constructed similar to retrieval loops 1016, 1018, described above with regard to FIG. 10A. Moreover, as shown in FIG. 18A, the outer surface of a downstream region of sheath 1803 may include markings 1809 for visually indicating a depth sheath 1803 has been inserted within a patient's GI tract through the anus. In addition, as shown in FIG. 18A, bypass device 1800 may include first and second suction/fluid inlet tubes 1814, 1816, which may be constructed similar to suction tubes 214, 216 described above. For example, fluid inlet tubes 1814, 1816 may each have a distal region having a set of inlet ports disposed within and in fluid communication with negative pressure chamber 1812, and a proximal end fluidically coupled to a pump configured to apply negative pressure within negative pressure chamber 1812. The proximal ends of fluid inlet tubes 1814, 1816 also may be fluidicly coupled to one or more vacuum/pressure transducers configured to measure pressure within negative pressure chamber 1812 via fluid inlet tubes 1814, 1816, as described in further detail below.

As shown in FIGS. 18A and 18C, bypass device 1800 further may include sensing tube 1818 having a distal region disposed within and in fluid communication with negative pressure chamber 1812 and a proximal end fluidically coupled to a vacuum/pressure transducer configured to measure pressure within negative pressure chamber 1812 via sensing tube 1818. Preferably, the distal regions of fluid inlet tubes 1814, 1816 and sensing tube 1818 are equally and circumferentially spaced apart within negative pressure chamber 1812, as shown in FIG. 18C. As will be understood by a person having ordinary skill in the art, the distal regions of fluid inlet tubes 1814, 1816 and sensing tube 1818 may be disposed in a different manner than is illustrated in FIG. 18C. In addition, there may be more or less than two fluid inlet tubes, and/or more or less than one sensing tube, as shown in FIG. 18C. Moreover, the number and arrangement of fluid inlet tubes and sensing tube(s) may be incorporated with any of the bypass devices described above, e.g., bypass devices 200, 1000, 1100, 1200, 1300, 1400, 1500, 1700.

Like bypass device 200, at least a portion of the outer surface of sheath 1803 within negative pressure chamber 1812 may include a plurality of microstructures, e.g., a micropattern of microstructures 1820, disposed thereon. For example, the micropattern of microstructures 1820 may comprise a micropattern of protrusions extending outwardly from the outer surface of sheath 1803. Preferably, the micropattern of microstructures 1820 is only disposed on the outer surface of sheath 1803 that is disposed within negative pressure chamber 1812. In addition, microstructures 1820 preferably are integrally formed with the portion of sheath 1803 within negative pressure chamber 1812. Alternatively, microstructures 1820 may be affixed to the portion of sheath 1803 within negative pressure chamber 1812 during manufacture.

As shown in FIG. 18B, each microstructure of the micropattern of microstructures 1820 may have a semi-spherical shape. For example, each microstructure of the micropattern of microstructures 1820 may have a cross-sectional width of between 50 and 500 microns, e.g., about 300 microns, and a height of between 50 to 1000 microns, e.g., about 600 microns. In some embodiments, each microstructure of the micropattern of microstructures 1820 may have a pitch of between 800-1200 microns, e.g., about 1000 microns. As will be understood by a person having ordinary skill in the art, the microstructures may have other shapes, e.g., columns, cubes, cones, pyramidal, circular pillars, rectangles, triangles, squares, sinusoids, etc.

The micropattern of microstructures 1820 may include a plurality of rows and a plurality of columns of microstructures throughout negative pressure chamber 1812. For example, the micropattern of microstructures 1820 may extend radially around a full circumference of the outer surface of sheath 1803 and longitudinally along an entire length of the outer surface of sheath 1803 within negative pressure chamber 1812. In some embodiments, the micropattern of microstructures 1820 may be arranged in a triangular or rectangular shape on the outer surface of sheath 1803 within negative pressure chamber 1812. In some embodiments, the outer surface of sheath 1803 further may include one or more ribs and/or one or more channels sized and shaped to guide fluid flow within negative pressure chamber 1812, e.g., towards fluid inlet tubes 1814, 1816.

Upon actuation of the negative pressure system, e.g., an external pump fluidicly coupled to the one or more suction tubes, a vacuum having a predetermined pressure may be created within negative pressure chamber 1812 to thereby pull intestinal tissue toward anchor 1801 and secure bypass device 1800 at the target site. At least some intestinal tissue may be pulled through at least some openings of the stent/scaffold of middle region 1806, and further may contact the micropattern of microstructures 1820. The micropattern of microstructures 1820 is configured to inhibit the inner wall of the intestine from sealing against the outer surface of sheath 1803 responsive to the vacuum to thereby encourage 360° fluidic communication within negative pressure chamber 1812. Thus, the micropattern of microstructures 1820 prevents the intestinal tissue from shutting off on the outer surface of sheath 1803 and creating a sub-chamber of vacuum within negative pressure chamber 1812. Accordingly, the micropattern of microstructures 1820 maintains a vacuum throughout negative pressure chamber 1812 such that anchor 1801 remains anchored at the target location when negative pressure is applied in negative pressure chamber 1812. By implementing a micropattern of microstructures on the outer surface of a sheath within the negative pressure chamber to encourage 360° fluidic communication within the negative pressure chamber, as well as an anchor having a recessed middle region, e.g., dog bone shape resembling an hourglass, to improve mechanical anchoring, and automated pump parameters adjustment to improve vacuum maintenance, the overall length of the stent/scaffold of the anchor may be reduced, e.g., 80-90 mm, or 70 mm.

Figure 19A:
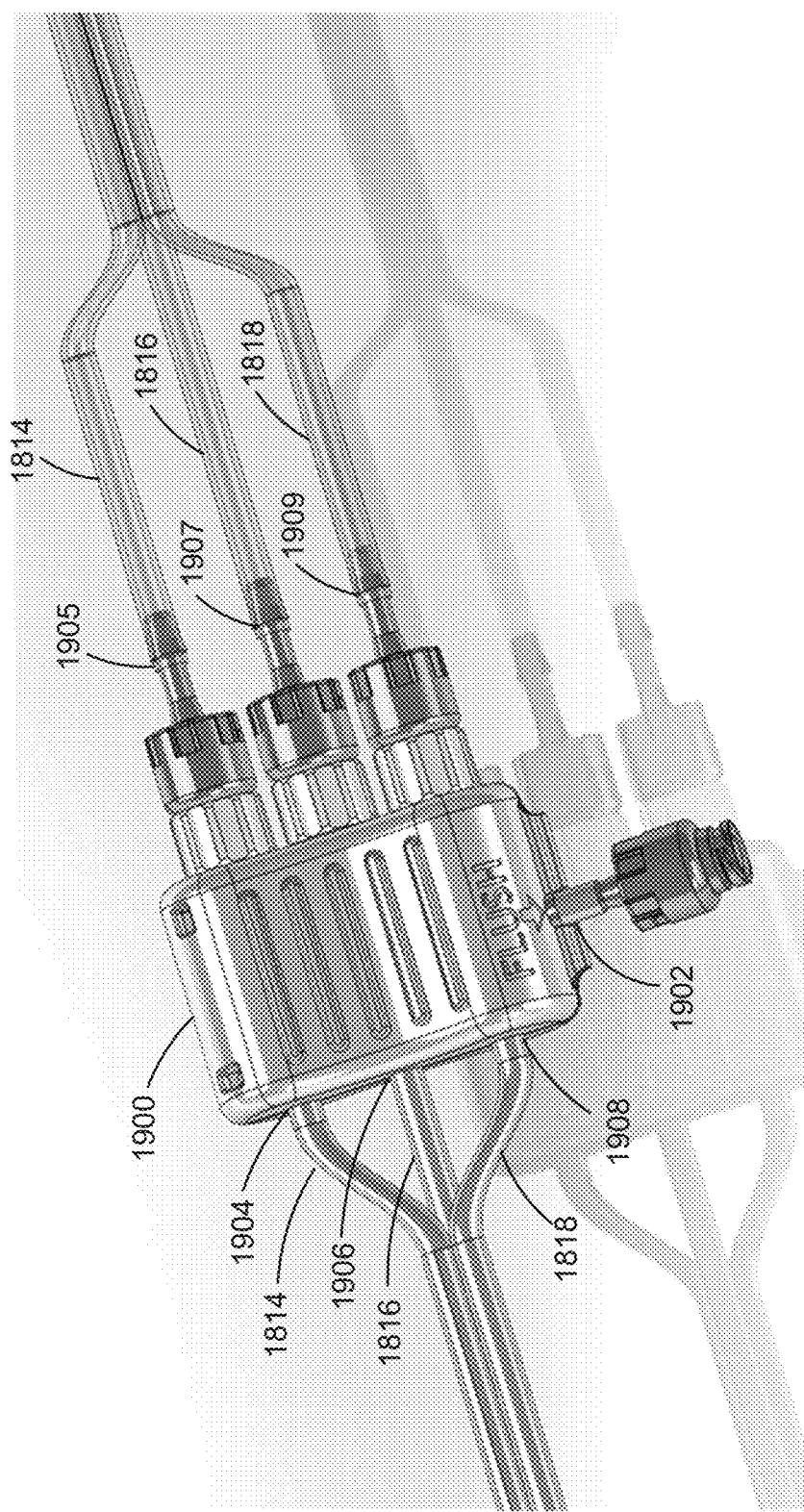
FIG. 19A illustrates an exemplary manifold of the negative pressure bypass system of FIG. 18A, constructed in accordance with the principles of the present disclosure.
Figure 19B:
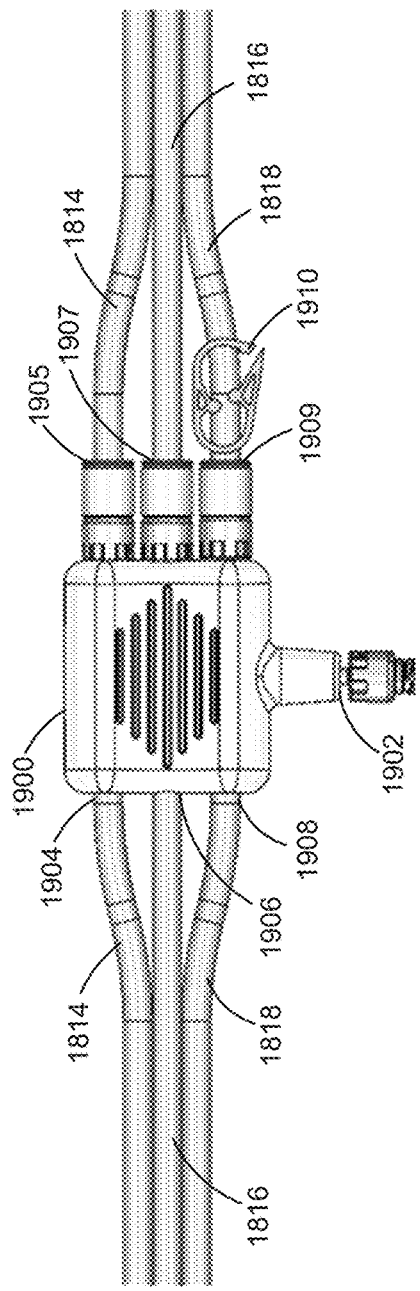
FIG. 19B illustrates the manifold of FIG. 19A with a closed clamp.
Figure 19C:
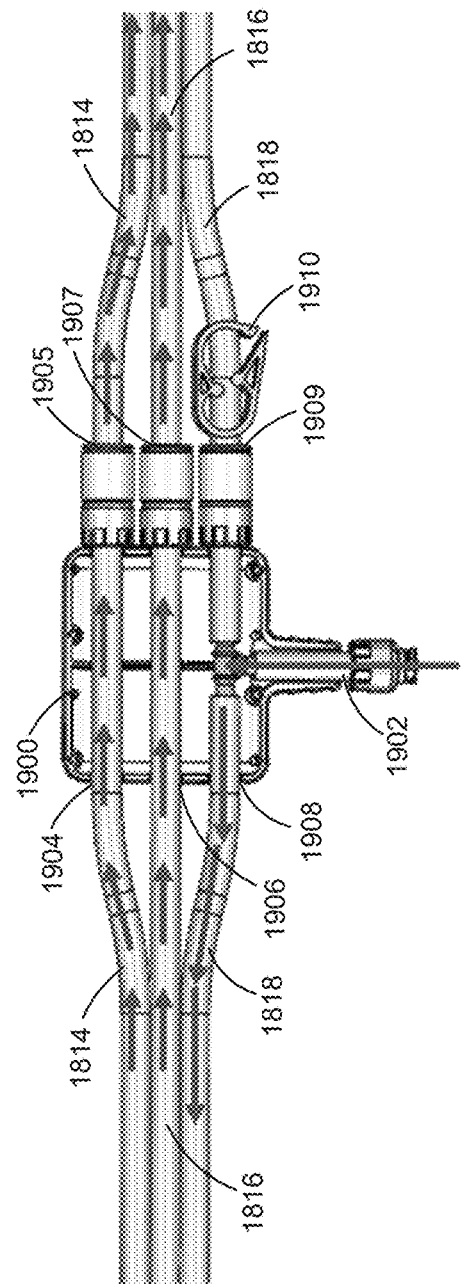
FIG. 19C illustrates the manifold of FIG. 19A with an open clamp during flushing.

Referring now to FIGS. 19A to 19C, an exemplary manifold for fluidicly coupling the fluid inlet tubes and the sensing tube to the negative pressure chamber and to the respective pump and pressure/vacuum transducers is provided. As shown in FIG. 19A, manifold 1900 may include first inlet port 1904 and first outlet port 1905 sized and shaped to receive first inlet tube 1814 therethrough, such that first inlet tube 1814 extends into manifold 1900 through first inlet port 1904 and out of manifold 1900 through first outlet port 1905, and second inlet port 1906 and second outlet port 1907 sized and shaped to receive second inlet tube 1816 therethrough, such that second inlet tube 1816 extends into manifold 1900 through second inlet port 1906 and out of manifold 1900 through second outlet port 1907. In addition, manifold 1900 may include third inlet port 1908 sized and shaped to receive a downstream end of a distal portion of sensing tube 1818 therethrough, and third outlet port 1909 sized and shaped to receive an upstream end of a proximal portion of sensing tube 1818 therethrough, such that sensing tube 1818 extends into manifold 1900 through third inlet port 1908 and out of manifold 1900 through third outlet port 1909.

As described above, the distal/upstream regions of fluid inlet tubes 1814, 1816 and sensing tube 1818 may extend towards and be disposed within the negative pressure chamber of the anchor, and the proximal/downstream ends of fluid inlet tubes 1814, 1816 and sensing tube 1818 may extend towards and be fluidicly coupled to the respective pump and pressure/vacuum transducers. As shown in FIGS. 19B and 19C, manifold 1900 further may include clamp 1910 configured to transition between an open state where fluid is permitted to flow throughout sensing tube 1818, as shown in FIG. 19B, and a closed state where fluid flow is prevented through at least a portion of sensing tube 1818, e.g., beyond clamp 1910, as shown in FIG. 19C. As shown in FIG. 19C, clamp 1910 may be coupled to the proximal portion of sensing tube 1818, downstream of the junction of fluid port 1902 and sensing tube 1818. Moreover, clamp 1901 may be removeably coupled to sensing tube 1818, or alternatively, may be permanently fixed to/integral with sensing tube 1818.

Manifold 1900 further may include flush port 1902 in fluid communication with sensing tube 1818. For example, flush port 1902 may be fluidicly coupled to the downstream end of a distal portion of sensing tube 1818 and to the upstream end of a proximal portion of sensing tube 1818, as shown in FIG. 19C. Flush port 1902 may be configured to receive fluid from a fluid source for flushing fluid inlet tubes 1814, 1816 and sensing tube 1818, e.g., for routine cleaning/maintenance and/or to remove a clog therein. For example, clamp 1910 may be transitioned to its closed state and fluid may be introduced through fluid port 1902, such that clamp 1901 forces the fluid to flow through sensing tube 1818 in an upstream direction towards the negative pressure of the anchor. As negative pressure is applied to the negative pressure chamber via fluid inlet tubes 1814, 1816, the fluid within the negative pressure chamber will flow through fluid inlet tubes 1814, 1816 in a downstream direction towards the fluid reservoir chamber of the external pump, as shown in FIG. 19C.

Figure 20:
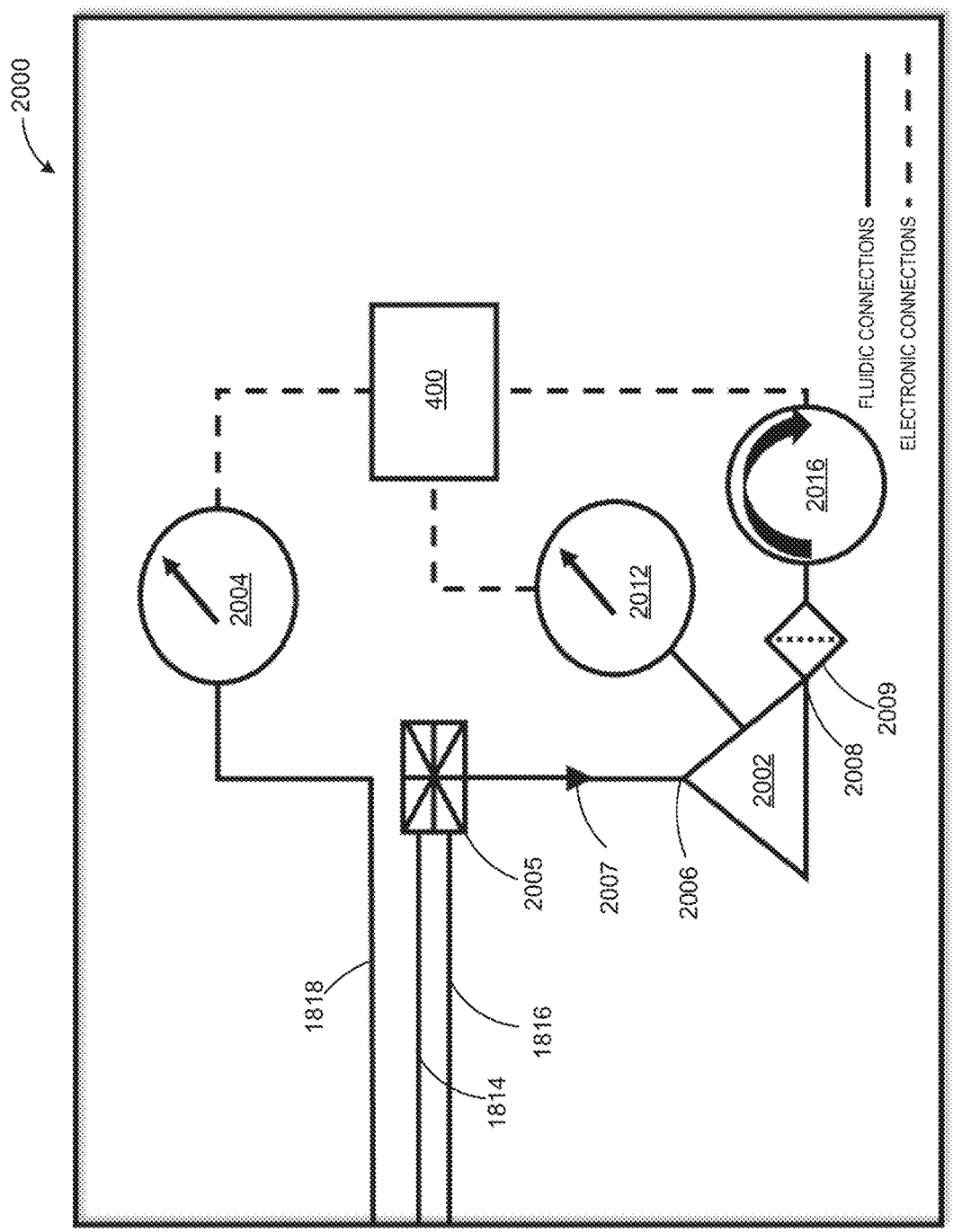
FIG. 20 is a schematic illustrating various components of an exemplary pump device of the negative pressure bypass system of FIGS. 18A to 18C constructed in accordance with the principles of the present disclosure.

FIG. 20 is a schematic illustrating the internal components of an alternative negative pressure system for generating the vacuum within the negative pressure chamber. System 2000 may be constructed similar to system 300 of FIGS. 3A and 3B, and may be used with any of the bypass devices described herein when a sensing line is utilized, e.g., bypass device 1800 having sensing line 1818. For example, system 2000 may include a housing sized and shaped to house an external pump therein, and may be fluidicly coupled to the downstream ends of the suction/fluid inlet tubes, e.g., tubes 242, 216, 1814, 1816. As shown FIG. 20, system 2000 may include a controller, e.g., controller 400, in electrical communication with the electrical components of system 2000, e.g., pump 2016 and pressure transducers 2004, 2012, described in further detail below. System 2000 may include fluid reservoir chamber 2002 fluidicly coupled to pump 2016. Fluid reservoir chamber 2002 may be sized and shaped for collecting fluid and waste matter within the fluid evacuated from the negative pressure chamber of the anchor. Controller 400 may be operatively coupled to pump 2016, e.g., via pump interface 414, as described above with regard to FIG. 4. Accordingly, pump interface 414 may cause pump 2016 to generate a vacuum having a predetermined pressure within the negative pressure chamber via the fluid inlet tubes. For example, fluid evacuated from the negative pressure chamber may travel through fluid inlet tubes 1814, 1816, and enter fluid reservoir chamber 2002 via inlet 2006.

In addition, may include vacuum/pressure transducer 2012 fluidicly coupled to the negative pressure chamber of the anchor via fluid reservoir chamber 2002 and the suction/fluid inlet tubes coupled thereto, e.g., fluid inlet tubes 1814, 1816. In some embodiments, each fluid inlet tube may be fluidicly coupled to a dedicated pressure transducer for measuring pressure within the respective fluid inlet tube. Pressure transducer 2012 may be configured to measure pressure within the negative pressure chamber via fluid inlet tubes 1814, 1816, and generate one or more signals indicative of the measured pressure for transmission to controller 400, e.g., system parameters determination module 412. Accordingly, system parameters determination module 412, may be configured to receive, process, and analyze pressure data received from pressure transducer 2012 to calculate the pressure within negative pressure chamber via fluid inlet tubes 1814, 1816.

As shown in FIG. 20, fluid inlet tubes 1814, 1816 may be fluidicly coupled together via coupler 2005, such that a single fluid inlet line in fluid communication with both fluid inlet tubes 1814, 1816 is fluidicly coupled to fluid reservoir chamber 2002 via inlet 2006 of fluid reservoir chamber 2002. Waste matter within the fluid evacuated from the negative pressure chamber and other fluids may be collected within fluid reservoir chamber 2002, such that the remaining fluid, e.g., gas, may exit fluid reservoir chamber 2002 via outlet 2008 and travel across filter 2009 and exit system 2000 via pump 2016. In addition, system 2000 may include filter 2009 disposed between fluid reservoir chamber 2002 and pump 2016 to prevent waste matter from entering pump 2016. Fluid reservoir chamber 2002 may be removably coupled to the housing to facilitate removal of waste matter from fluid reservoir chamber 2002 and/or cleaning of fluid reservoir chamber 2002. Like system 300, system 2000 further may include one or more check valves fluidicly coupled to suction tubes 1814, 1816, e.g., between filter 2009 and pump 2016, configured to allow pump 2016 to return to ambient pressure, e.g., atmospheric pressure, without impacting pressure of system 2000.

As shown in FIG. 20, system 2000 may include vacuum/pressure transducer 2004 fluidically coupled to the negative pressure chamber of the anchor via dedicated sensing tube 1818, which has a direct path to the negative pressure chamber and should always be clear of potential occluders, e.g., waste matter. Pressure transducer 2004 may be configured to measure pressure within the negative pressure chamber via sensing tube 1818, and generate one or more signals indicative of the measured pressure for transmission to controller 400, e.g., system parameters determination module 412, described above with regard to FIG. 4. Accordingly, system parameters determination module 412 may be configured to receive, process, and analyze pressure data received from pressure transducer 2004 to calculate the pressure within the negative pressure chamber as measured by sensing tube 1818. For example, when system parameters determination module 412 determines that the pressure within the negative pressure chamber falls outside of the predetermined range, controller 400 may automatically adjust one or more operating parameters of pump 2016, and instruct pump 2016 to operate in accordance with the adjusted parameters, to thereby maintain the pressure within the negative pressure chamber within the predetermine range.

System parameters determination module 412 may be configured to detect vacuum pressure differences between sensing tube 1818 and fluid inlet tubes 1814, 1816 by comparing pressure measurement data received from pressure transducers 2004, 2012, e.g., pressure within the negative pressure chamber of the anchor and pressure within fluid reservoir chamber 2002, and may determine the presence of an occlusion/blockage/clog within at least one of fluid inlet tubes 1814, 1816, and/or when fluid reservoir chamber 2002 is full and needs to be emptied/changed, e.g., when the pressure differential detected exceeds a predetermined pressure threshold. In some embodiments, system 2000 may include one or more additional sensors fluidically coupled to fluid reservoir chamber 2002 and configured to measure an amount of waste matter within fluid reservoir chamber 2002. The one or more additional sensors may generate one or more signals indicative of the level of waste matter within fluid reservoir chamber 2002 for transmission to controller 400.

In addition, controller 400 of system 2000 may generate one or more alerts, e.g., via alert generation module 416 of controller 400, described above with regard to FIG. 4. For example, alert generation module 416 may be configured to generate an alert when the pressure within the negative pressure chamber falls outside of the predetermined range, to periodically facilitate routine manual inspection of system 2000 by a user, when the amount of waste matter within fluid reservoir chamber 2002 measured exceeds the predetermined threshold, when the presences of a clog is detected within fluid inlet tubes 1814, 1816, etc.

Figure 21A:
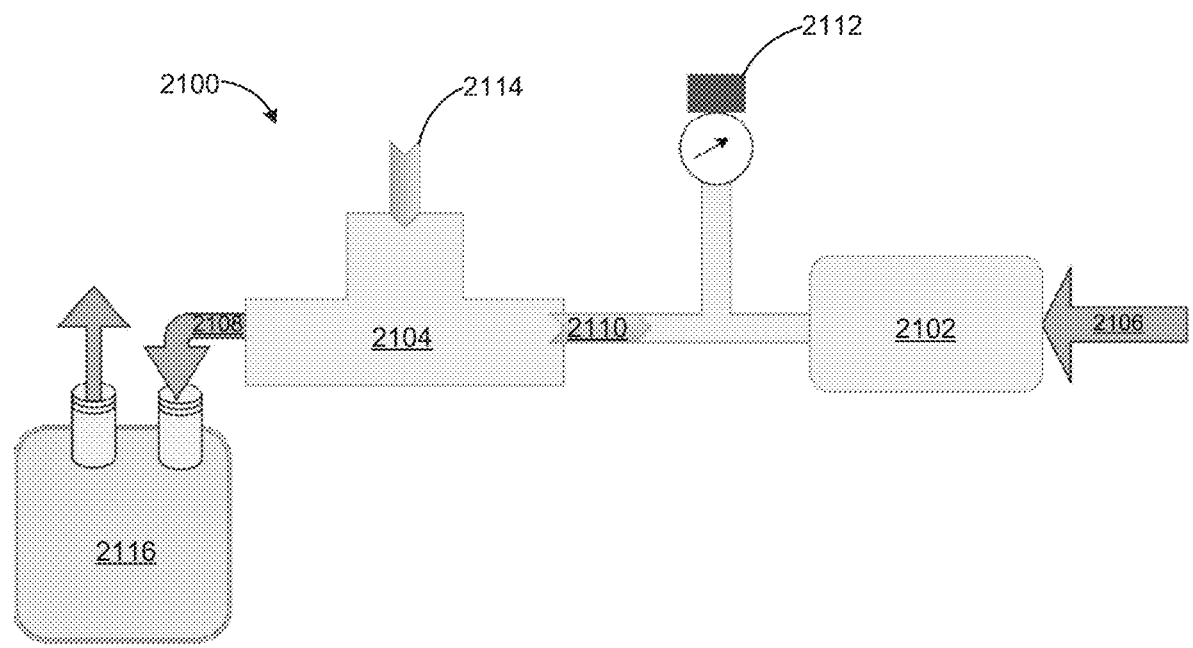
FIGS. 21A and 21B are schematics illustrating various components of an alternative exemplary pump device of the negative pressure bypass system constructed in accordance with the principles of the present disclosure.
Figure 21B:
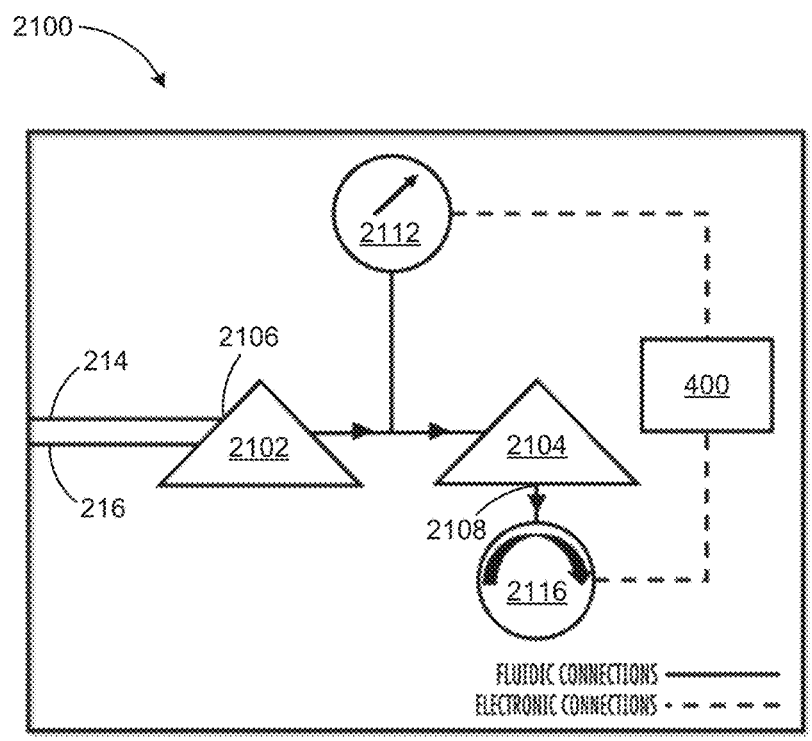

Referring now to FIGS. 21A and 21B, internal components of an alternative exemplary negative pressure system is provided. Negative pressure system 2100 may be constructed similar to system 300. For example, fluid reservoir chamber 2102 having inlet 2106 configured to be fluidically coupled to one or more suction tubes, e.g., suction tubes 214, 216, pump 2112, and pressure transducer 2112 correspond with fluid reservoir chamber 302 having inlet 306, pump 316, and pressure transducer 312. System 2100 differs from system 300 in that system 2100 may include pressure normalization chamber 2104 fluidically coupled to pump 2116. For example, fluid reservoir chamber 2102 may be fluidicly coupled to pressure normalization chamber 2104 via valve 2110, e.g., a solenoid valve, as shown in FIG. 21A. Valve 2110 may be configured to be actuated to transition between a closed state where fluid reservoir chamber 2102 is fluidicly isolated from pressure normalization chamber 2104, and an open state where fluid reservoir chamber 2102 is fluidicly coupled to pressure normalization chamber 2104.

In addition, pressure normalization chamber 2104 may include check valve 2114 configured to be actuated to permit pressure normalization chamber 2104 to reach atmospheric pressure. For example, check valve 2114 may be actuated to an open state to allow pressure normalization chamber 2104, prior to turning on pump 2116. When the pressure within pressure normalization chamber 2104 is at atmospheric pressure, pump 2116 may be turned on, check valve 2114 may be actuated to a closed state, and valve 2110 may be actuated to the open state to fluidicly couple pump 2116, fluid reservoir chamber 2102, and pressure normalization chamber 2104, such that pump 2116 may generate a vacuum having a predetermined pressure within negative pressure chamber 212. In some embodiments, instead of check valve 2114, system 2100 may include a small controlled leak configured to allow pressure normalization chamber 2104 to reach atmospheric pressure, e.g., when system 2100 is in steady state conditions.

Moreover, waste matter within the fluid evacuated from negative pressure chamber 212 and other fluids may be collected within fluid reservoir chamber 2102, such that the remaining fluid, e.g., gas, may travel across valve 2110 in the open state to pressure normalization chamber 2104 and exit system 2100 via pump 2116. For example, the fluid may exit pressure normalization chamber 2104 via outlet 2108. As shown in FIG. 21B, system 2100 may include controller 400 in electrical communication with the electrical components of system 2100, e.g., pump 2116 and pressure transducer 2112. In some embodiments, system 2100 may include one or more additional sensors fluidicly coupled to fluid reservoir chamber 2102 and configured to measure an amount of waste matter within fluid reservoir chamber 2102. The one or more additional sensors may generate one or more signals indicative of the level of waste matter within fluid reservoir chamber 2102 for transmission to controller 400.

While various illustrative embodiments of the invention are described above, it will be apparent to one skilled in the art that various changes and modifications may be made therein without departing from the invention. For example, any of the bypass devices described above, e.g., bypass devices 200, 1000, 1100, 1200, 1300, 1400, 1500, 1700, 1800 may incorporate upstream and/or downstream retrieval loops to facilitate removal of the respective anchor from the patient's GI tract, and/or a double anchor as described above. The appended claims are intended to cover all such changes and modifications that fall within the true scope of the invention.

What is claimed:

1. A system for protecting an anastomosis in an intestine, the system comprising:
    an anchor configured to be implanted at a target location in the intestine upstream of the anastomosis, the anchor configured to transition from a compressed state to an expanded state wherein an outer surface of the anchor contacts an inner wall of the intestine at the target location;

a sheath disposed within the anchor and coupled to the anchor to define a negative pressure chamber between an outer surface of the sheath and the inner wall of the intestine;

one or more fluid inlet tubes fluidically coupling the negative pressure chamber to a pump, wherein the outer surface of the sheath comprises a micropattern of microstructures, each microstructure comprising a protrusion configured to inhibit the inner wall of the intestine from sealing against the outer surface of the sheath to maintain a vacuum throughout the negative pressure chamber such that the anchor remains anchored at the target location when negative pressure is applied in the negative pressure chamber by the pump via the one or more fluid inlet tubes.

2. The system of claim 1, wherein the anchor comprises:
an inner mesh anchor comprising a downstream region, an upstream region, and a middle region extending between the downstream and upstream regions, the middle region having an outer diameter less than outer diameters of the downstream and upstream regions; and
an outer mesh anchor disposed over the inner mesh anchor, the outer mesh anchor configured to transition from a cylindrical configuration towards a shape corresponding to a geometry of the inner mesh anchor when negative pressure is applied in the negative pressure chamber.

3. The system of claim 2, wherein the sheath is sealed to upstream and downstream regions of the inner and outer mesh anchors via an upstream seal and a downstream seal, respectively, to thereby define the negative pressure chamber between the outer surface of the sheath, the upstream and downstream seals, and the inner wall of the intestine.

4. The system of claim 2, wherein, prior to application of the negative pressure in the negative pressure chamber, the inner mesh anchor exhibits an hourglass configuration and the outer mesh anchor exhibits the cylindrical configuration, and wherein, upon application of the negative pressure in the negative pressure chamber while at the target location within the intestine, the outer mesh anchor and the inner mesh anchor both exhibit the hourglass configuration.

5. The system of claim 1, wherein each microstructure of the micropattern of microstructures has a shape comprising a circular pillar, rectangle, triangle, square, sinusoid, or semi-spherical shape.

6. The system of claim 1, wherein the micropattern of microstructures extends radially around a full circumference of the outer surface of the sheath and longitudinally along an entire length of the outer surface of the sheath within the negative pressure chamber.

7. The system of claim 1, wherein the sheath is configured to extend downstream from the anchor, across the anastomosis, and out an anus.

8. The system of claim 1, wherein the micropattern of microstructures is only on the outer surface of the sheath within the negative pressure chamber.

9. The system of claim 1, wherein the micropattern of microstructures is configured to inhibit the inner wall of the intestine from sealing against the outer surface of the sheath responsive to the vacuum to thereby encourage 360° fluidic communication within the negative pressure chamber.

10. The system of claim 1, wherein the micropattern of microstructures comprises a plurality of rows and a plurality of columns of microstructures throughout the negative pressure chamber.

11. The system of claim 1, wherein the micropattern of microstructures is arranged in a triangular or rectangular shape on the outer surface of the sheath within the negative pressure chamber.

12. The system of claim 1, wherein the outer surface of the sheath comprises at least one of ribs or channels configured to guide fluid flow within the negative pressure chamber.

13. The system of claim 1, wherein each microstructure of the micropattern of microstructures has a cross-sectional width of between 50 and 500 microns, and a height of between 50 to 1000 microns.

14. The system of claim 13, wherein each microstructure of the micropattern of microstructures has a cross-sectional width of about 300 microns and a height of about 600 microns.

15. The system of claim 1, wherein each protrusion is configured to extend outwardly from the outer surface of the sheath towards the inner wall of the intestine.

16. The system of claim 1, wherein each of the one or more fluid inlet tubes has a downstream end coupled to the pump and an upstream end having one or more pores in fluid communication with the negative pressure chamber.

17. The system of claim 16, wherein upstream ends of the one or more fluid inlet tubes are equally and circumferentially spaced apart within the negative pressure chamber.

18. The system of claim 16, further comprising one or more sensors configured to measure data indicative of pressure within the negative pressure chamber.

19. The system of claim 18, further comprising a controller operatively coupled to the pump and the one or more sensors, the controller programmed with instructions configured to:

actuate the pump at predetermined pump parameters to evacuate fluid from the negative pressure chamber via the one or more fluid inlet tubes to generate the vacuum within the negative pressure chamber having a pressure within a predetermined pressure range, the vacuum sufficient to pull intestinal tissue toward the anchor to maintain the anchor at the target location;

compare the data indicative of the pressure within the negative pressure chamber received from the one or more sensors over time with the predetermined pressure range; and adjust, if the pressure within the negative pressure chamber falls outside the predetermined pressure range, the predetermined pump parameters of the pump, such that the pump applies and maintains the vacuum within the predetermined pressure range within the negative pressure chamber.

20. The system of claim 19, wherein the controller is configured to generate an alert if the pressure within the negative pressure chamber falls outside the predetermined pressure range.

21. The system of claim 19, wherein the controller is configured to:

calculate an actual pump run time of the pump to achieve a predetermined total volume of the system; and determine a presence of an occlusion in the system if the actual pump run time deviates from an expected pump run time.

22. The system of claim 21, wherein the controller is configured to generate an alert upon determination of the presence of the occlusion in the system.

23. A method for protecting an intestinal anastomosis, the method comprising:

positioning an anchor at a target location in the intestine upstream of the anastomosis, the anchor coupled to a sheath disposed within the anchor to define a negative pressure chamber between an outer surface of the sheath and an inner wall of the intestine;

transitioning the anchor from a compressed state to an expanded state wherein an outer surface of the anchor contacts the inner wall of the intestine at the target location; and applying negative pressure in the negative pressure chamber via one or more fluid inlet tubes fluidically coupling the negative pressure chamber to a pump, wherein the outer surface of the sheath comprises a micropattern of microstructures, each microstructure comprising a protrusion configured to inhibit the inner wall of the intestine from sealing against the outer surface of the sheath to maintain a vacuum throughout the negative pressure chamber when negative pressure is applied in the negative pressure chamber, such that the anchor remains anchored at the target location.

24. The method of claim 23, wherein the micropattern of microstructures extends radially around a full circumference of the outer surface of the sheath within the negative pressure chamber.

25. The method of claim 23, wherein the micropattern of microstructures is only on the outer surface of the sheath within the negative pressure chamber.

26. The method of claim 23, wherein the micropattern of microstructures is configured to inhibit the inner wall of the intestine from sealing against the outer surface of the sheath responsive to the vacuum to thereby encourage 360° fluidic communication within the negative pressure chamber.

27. The method of claim 23, wherein each protrusion is configured to extend outwardly from the outer surface of the sheath towards the inner wall of the intestine.

28. The method of claim 23, wherein the anchor comprises:

an inner mesh anchor and an outer mesh anchor disposed over the inner mesh anchor, the inner mesh anchor comprising a downstream region, an upstream region, and a middle region extending between the downstream and upstream regions, the middle region having an outer diameter less than outer diameters of the downstream and upstream regions, and wherein, upon application of negative pressure in the negative pressure chamber, the outer mesh anchor transitions from a cylindrical configuration towards a shape corresponding to a geometry of the inner mesh anchor.

29. The method of claim 28, wherein the sheath is sealed to upstream and downstream regions of the inner and outer mesh anchors via an upstream seal and a downstream seal, respectively, to thereby define the negative pressure chamber between the outer surface of the sheath, the upstream and downstream seals, and the inner wall of the intestine, and wherein the micropattern of microstructures is only on the outer surface of the sheath between the upstream and downstream seals within the negative pressure chamber.

30. The method of claim 28, wherein, prior to application of the negative pressure in the negative pressure chamber, the inner mesh anchor exhibits an hourglass configuration and the outer mesh anchor exhibits the cylindrical configuration, and wherein, upon application of the negative pressure in the negative pressure chamber while at the target location within the intestine, the outer mesh anchor and the inner mesh anchor both exhibit the hourglass configuration.

\* \* \* \* \*